(12) United States Patent
Smith

(10) Patent No.: US 8,308,946 B2
(45) Date of Patent: Nov. 13, 2012

(54) SYSTEMS AND METHODS FOR ANAEROBIC DIGESTION OF BIOMATERIALS

(75) Inventor: Charles Satish Smith, West Chester, PA (US)

(73) Assignee: Epcot Crenshaw Corporation, West Chester, PA (US)

( * ) Notice: Subject to any disclaimer, the term of this patent is extended or adjusted under 35 U.S.C. 154(b) by 0 days.

(21) Appl. No.: 13/360,669

(22) Filed: Jan. 28, 2012

(65) Prior Publication Data

US 2012/0125840 A1 May 24, 2012

(51) Int. Cl.
*C02F 3/28* (2006.01)
*C02F 11/04* (2006.01)

(52) U.S. Cl. ........ 210/603; 210/612; 210/614; 210/103; 210/120; 210/149

(58) Field of Classification Search .................. 210/603, 210/612, 614, 97, 103, 104, 120, 149
See application file for complete search history.

(56) References Cited

U.S. PATENT DOCUMENTS

| | | | |
|---|---|---|---|
| 3,992,268 A | | 11/1976 | Antos |
| 4,722,741 A | | 2/1988 | Hayes et al. |
| 4,824,571 A | * | 4/1989 | Ducellier et al. ............. 210/603 |
| 5,185,079 A | | 2/1993 | Dague |
| 5,989,428 A | * | 11/1999 | Goronszy .................... 210/605 |
| 6,190,554 B1 | | 2/2001 | Mandt |
| 6,342,378 B1 | | 1/2002 | Zhang et al. |
| 6,660,164 B1 | * | 12/2003 | Stover ......................... 210/612 |
| 6,673,243 B2 | | 1/2004 | Srinivasan et al. |
| 6,811,701 B2 | | 11/2004 | Wilkie |
| 7,309,432 B1 | * | 12/2007 | Fabiyi et al. ................. 210/604 |
| 7,556,737 B2 | | 7/2009 | Zhang |
| 2006/0289356 A1 | | 12/2006 | Burnett et al. |
| 2008/0311640 A1 | | 12/2008 | Cox et al. |
| 2009/0261027 A1 | | 10/2009 | Elefritz, Jr. et al. |
| 2010/0018917 A1 | | 1/2010 | Fitch et al. |
| 2010/0032370 A1 | | 2/2010 | Allen et al. |
| 2010/0101464 A1 | | 4/2010 | Leach et al. |
| 2012/0085704 A1 | * | 4/2012 | Jenkins et al. ................ 210/614 |

OTHER PUBLICATIONS

Amon, Thomas, et al., "Biogas production from maize and dairy cattle manure—Influence of biomass composition on the methane yield," ScienceDirect, Agriculture, Ecosystems and Environment, 118:173-182 (2007).

(Continued)

*Primary Examiner* — Fred Prince
(74) *Attorney, Agent, or Firm* — Carter DeLuca Farrell LLP & Schmidt

(57) ABSTRACT

Systems and methods for performing anaerobic digestion of biomaterials using a clarifier, a batch reactor, and/or a digester are disclosed. The clarifier performs pretreatment processing of biomaterial to improve anaerobic digestion. The batch reactor and/or the digester are coupled to the clarifier and are configured to digest the processed biomaterial. A control system for an anaerobic digestion process includes a flow control system, a temperature control system, and a totalization system. The flow control system controls the flow of biomaterial and the delivery of chemical agents to the biomaterial based on conductivity, temperature, pressure, and/or composition of the biomaterial. The temperature control system includes a heat source and heat exchangers that control the temperature of the biomaterial. The totalization system senses the volume of biomaterial in at least one stage of an anaerobic digestion process and a controller controls the flow control system based upon the sensed volume of biomaterial.

16 Claims, 21 Drawing Sheets

OTHER PUBLICATIONS

Wang, Z., et al., "Accelerated hydrolysis and acidification of municipal solid waste (MSW) in a flushing anaerobic bio-reactor using treated leachate recirculation," Waste Manag. Res., 18:215 (2000).

Heaven, S., et al., "Effect of solid and liquid retention times on hydrolysis of maize," Water Science & Technology—WST, 58.7, pp. 1371-1378 (2008).

Puchajda, Bartek, et al., "Thermophilic anaerobic acid digestion of biosolids: hydrolysis, acidification, and optimization of retention time of acid digestion," J. Environ. Eng. Sci., 5:187-195 (2006).

Broughton, Alistair, "Hydrolysis and Acidogenesis of Farm Diary Effluent for Biogas Production at Ambient Temperatures," A thesis presented in partial fulfillment of the requiremenets for the degree of Master of Engineering in Environmental Engineering at Massey University, Palmerston North, New Zealand (2009).

Angenent, Largus, "Methanogenic population dynamics during startup of a full-scale anaerobic sequencing batch reactor treating swine waste," Water Research, 36:4648-4654 (2002).

Walker, Mark, "Use of a Hydraulic Flush Reactor in a Two-Stage Anaerobic Digestion Process for Biodegradable Municipal Waste," Environmental Engineering Science, vol. 26, No. 11, pp. 1599-1606 (2009).

Martin, Jr. Ph.D., John, "An Assessment of the Performance of the Colorado Pork, LLC Anaerobic Digestion and Biogas Utilization System," Eastern Research Group, Inc., pp. 1-43 (2003).

Steffen, R., et al., "Feedstocks for Anaerobic Digestion," Institute for Agrobiotechnology Tulln University of Agricultural Sciences Vienna, pp. 1-29 (1998).

"Anaerobic digestion," Residua Warmer Bulletin, www.residua.com, pp. 1-4.

\* cited by examiner

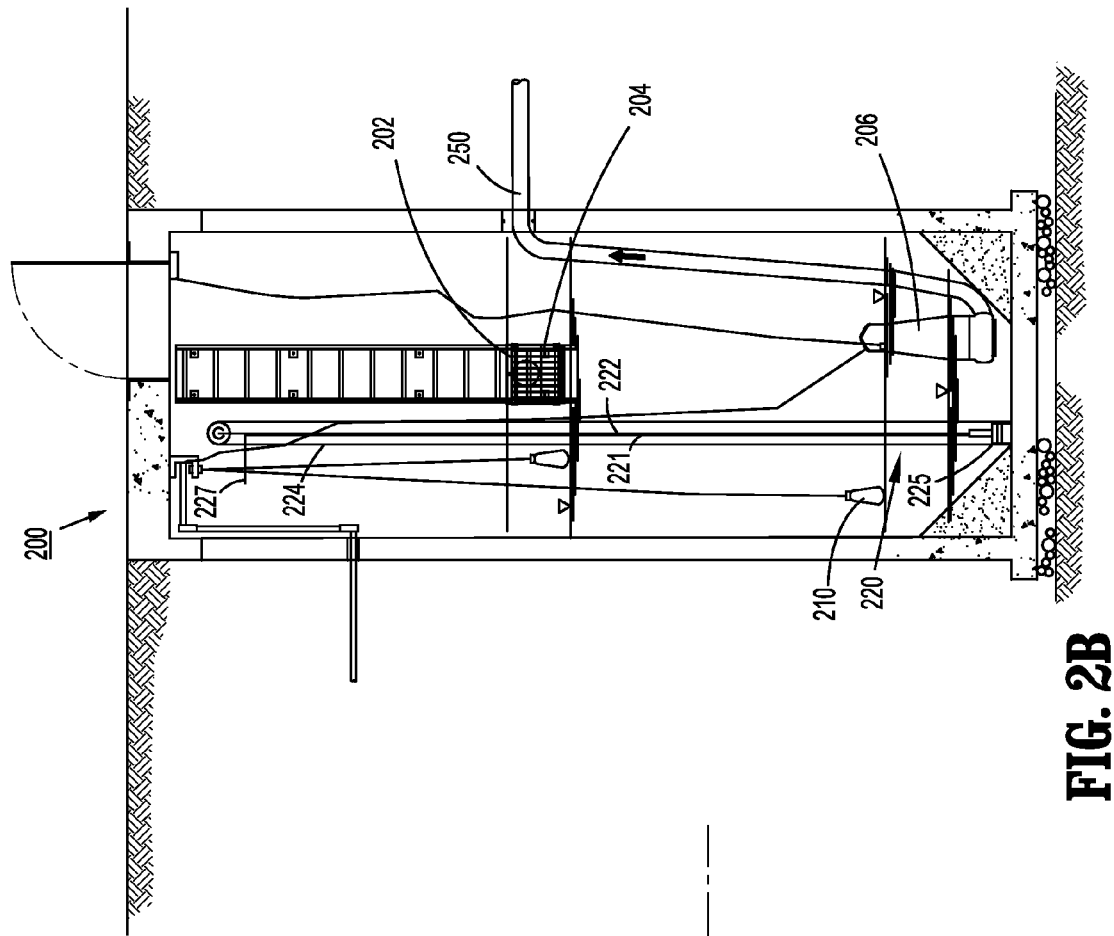
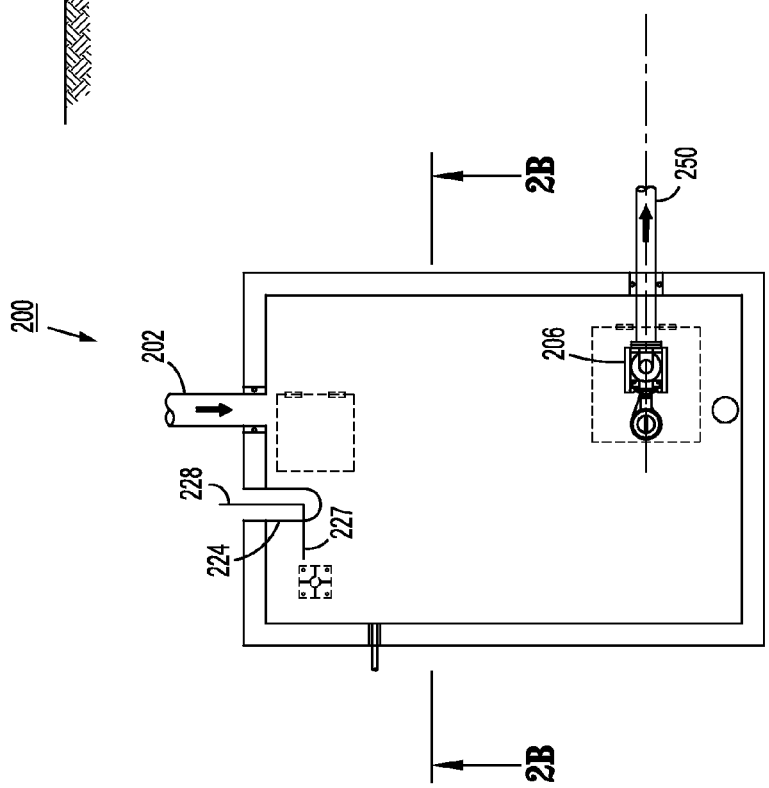
FIG. 2B
FIG. 2A

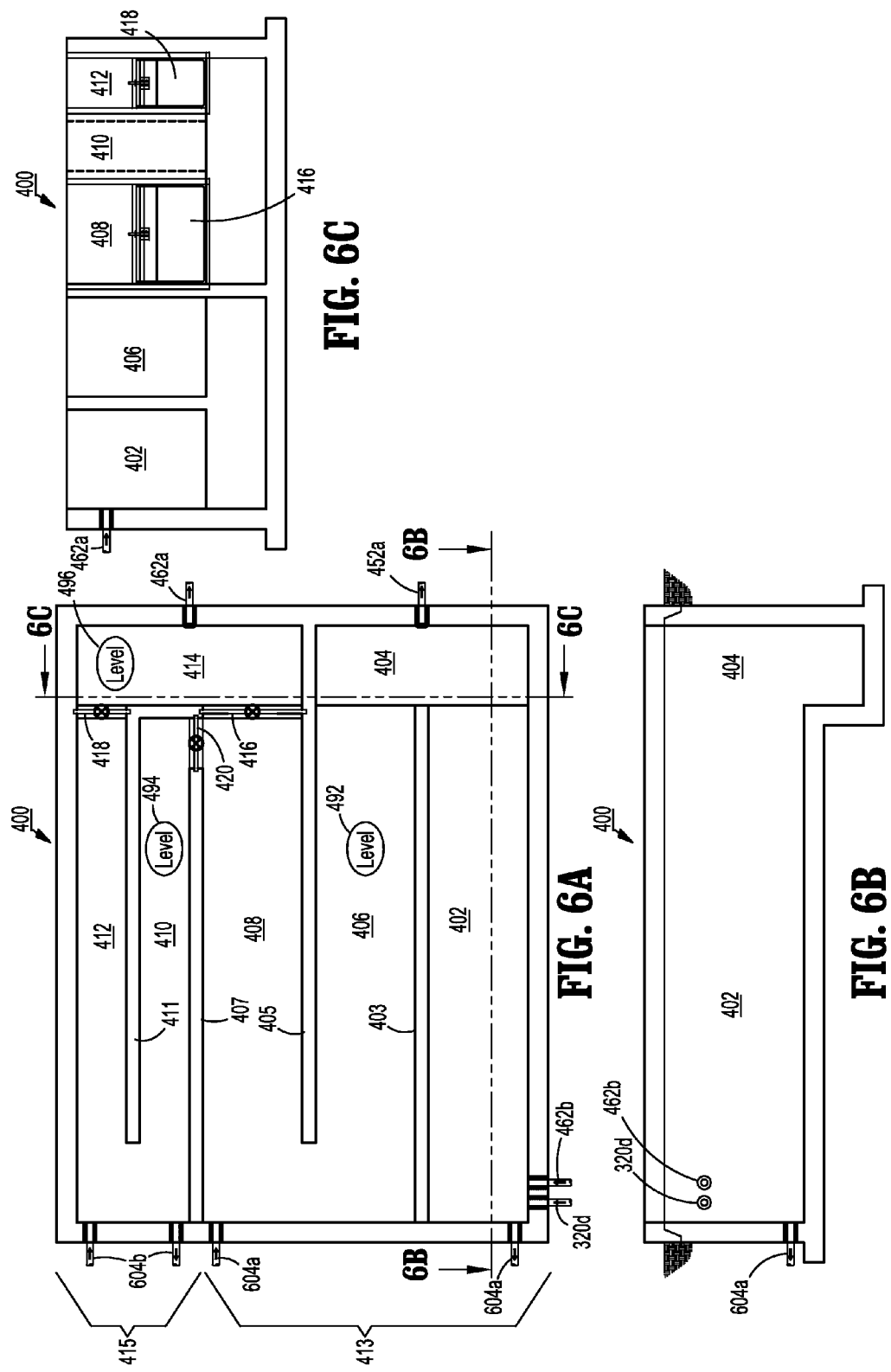

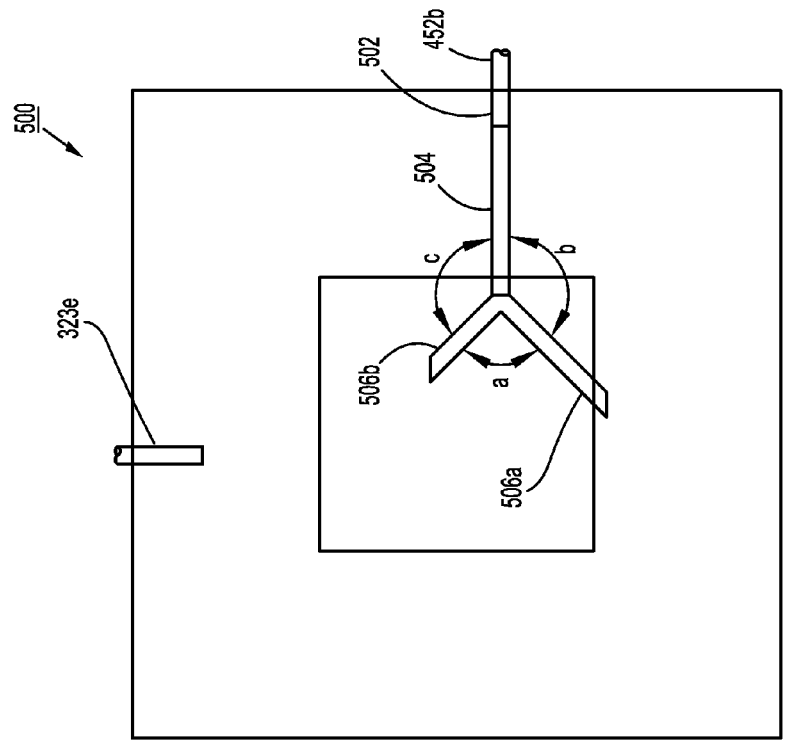
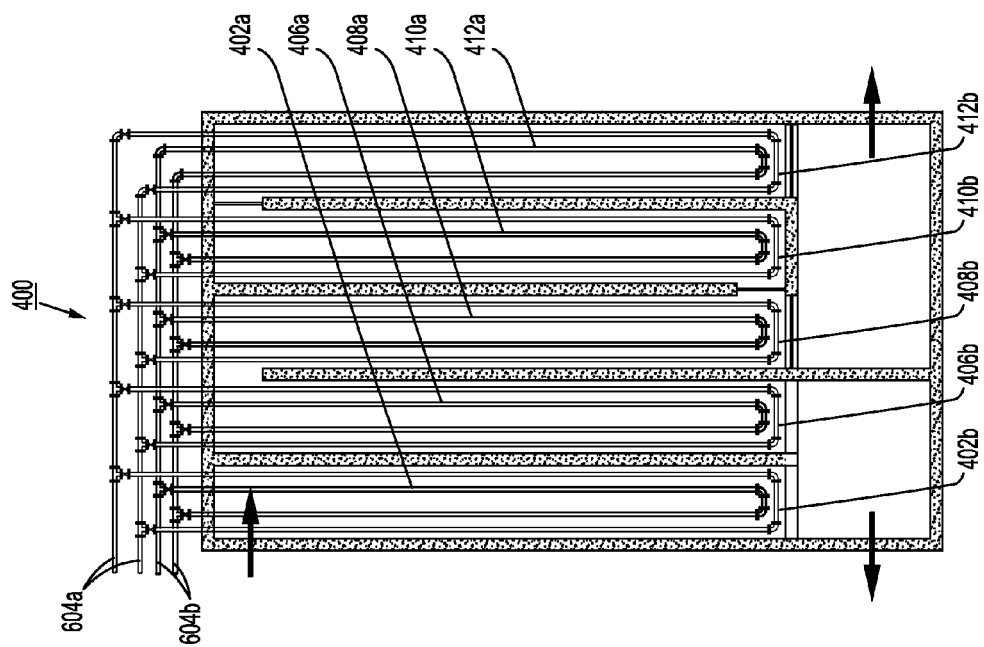

SYSTEMS AND METHODS FOR ANAEROBIC DIGESTION OF BIOMATERIALS

BACKGROUND

1. Technical Field

The present disclosure relates to an anaerobic digestion system including one or more digesters. More specifically, the present disclosure is directed to a clarifier for pretreatment processing of biomaterials to improve anaerobic digestion, a batch reactor for digesting the processed biomaterials, and a digester. The present disclosure also provides for an active monitoring system with dynamic material and gas flow control.

2. Background of Related Art

Anaerobic digestion is the breakdown of organic material by microorganisms in the absence of oxygen and has been used for the processing and treatment of primarily organic waste to produce non-hazardous, and sometimes beneficial, products.

The microbiology of anaerobic digestion can be generally described as comprising three broad trophic groups, which digest organic materials in sequence. The first group, the hydrolytic and fermentative bacteria, contains both obligate and facultative anaerobes, and removes small amounts of oxygen that may be introduced into the digester with the waste influent. By hydrolysis, this group initially breaks down the more complex molecules (e.g., cellulosics, starch, proteins, lipids, etc.) into smaller units (e.g., amino acids, sugars, and fatty acids). Then, by a process of acidification, this group uses these smaller compounds to produce formate, acetate, propionate, butyrate, hydrogen, and carbon dioxide. These acidic products are then available for the next trophic level. In many digesters, the rate-limiting step is the hydrolysis of complex molecules, particularly the polysaccharides.

The second trophic group comprises hydrogen-producing acetogenic bacteria or proton-reducing bacteria. By a process of acetification, this group makes acetate from compounds such as fatty acids, butyrate, formate, and propionate.

The third trophic group comprises the methanogenic bacteria, which convert compounds such as acetate into methane gas and carbon dioxide in a process called methanogenesis.

Conventional anaerobic digestion takes place within one or more digesters as the organic material is processed by the microorganisms described above. There is a continual need to provide for more efficient anaerobic digestion systems.

SUMMARY

In one aspect, the present disclosure features an anaerobic digestion system including a clarifier, a batch reactor, and a digester. The clarifier receives a first biomaterial and a second biomaterial, and undertakes pretreatment processing of the first and second biomaterials to form a digestate. The batch reactor is coupled to the clarifier. The batch reactor includes a plurality of chambers in fluid communication with each other that provide for the flow of the digestate through the batch reactor. The batch reactor also includes a digestion substrate disposed within the plurality of chambers. The digester is coupled to the batch reactor and is configured to receive the digestate from the batch reactor.

Each of the clarifier, the batch reactor, and the digester may include at least one gas sample port configured to withdraw gas from the clarifier, the batch reactor, and the digester. The gas sample ports may be coupled to a gas analyzer configured to analyze gas withdrawn from the clarifier, the batch reactor, the digester, or combinations thereof.

The anaerobic digestion system may further include a gas and mass flow control assembly configured to control a flow of gases and the digestate between the clarifier, the batch reactor, and the digester based on the gas analysis by the gas analyzer.

The first biomaterial may include a chemical oxygen demand per liter from about 1 gram to about 3,000 grams and volatile solids content per liter from about 1 gram to about 200 grams. The second biomaterial includes organic volatile solids, which may be loaded into the clarifier at a rate of from about 0.01 grams of organic volatile solids per liter-day to about 250 grams of organic volatile solids per liter-day.

The anaerobic digestion system may further include a heat source coupled to the clarifier, the batch reactor, the digester, or combinations thereof. The anaerobic digestion system may further include a gas and mass flow control assembly that withdraws at least one gas from the clarifier, the batch reactor, or the digester, and provides at least one gas to the heat source as a source of fuel.

Each of the clarifier, the batch reactor, and the digester may include at least one probe that measures at least one of pH or oxidation-reduction potential. The probes may be coupled to a chemical feed control assembly including at least one chemical supply tank. The chemical feed control assembly controls the release of a chemical agent stored therein.

The anaerobic digestion system may further include one or more biological reactors containing one or more microorganisms. The microorganisms may include a hydrolytic microorganism and an acidogenic microorganism. The one or more biological reactors may supply one or more of the microorganisms to the clarifier.

The batch reactor may contain one or more acetogenic microorganisms and the digester may contain one or more methanogenic microorganisms. The chambers in the batch reactor may be arranged in a serpentine configuration. The digester may be coupled to the clarifier and may recirculate the digestate through the clarifier.

In another aspect, the present disclosure features a method for anaerobic digestion. According to the method, a first biomaterial and a second biomaterial are received into a clarifier, in which pretreatment processing of the first and second biomaterials is selectively undertaken to form a digestate. The digestate is then passed through a batch reactor that includes a digestion substrate disposed in a plurality of chambers that are in fluid communication with each other. After the digestate passes through the batch reactor, the digestate is transferred to a digester. One or more gases generated during anaerobic digestion are removed from the clarifier, the batch reactor, or the digester and are supplied to the digester.

The plurality of chambers in the batch reactor may be arranged in a serpentine configuration. The digestion substrate disposed in the plurality of chambers of the batch reactor may include at least one acetogenic microorganism. Also, the digester may include at least one methanogenic microorganism.

The method for anaerobic digestion may further include pasteurizing the first and second biomaterials. The first biomaterial may be contacted with at least one acidogenic microorganism and the second biomaterial may be contacted with at least one hydrolytic microorganism within the clarifier.

The first biomaterial may include a chemical oxygen demand per liter from about 1 gram to about 3,000 grams and volatile solids content per liter from about 1 gram to about 200 grams. The second biomaterial may allow for a solid organic loading rate from about 0.01 grams of volatile solids per liter-day to about 250 grams of volatile solids per liter-day.

In yet another aspect, the present disclosure features an anaerobic digestion batch reactor. The anaerobic digestion batch reactor includes a plurality of chambers to provide for the flow of a digestate through the plurality of chambers, a digestion substrate disposed within at least one of the plurality of chambers, and one or more flow control mechanisms. The one or more flow control mechanisms may include a control valve or a sluice gate that controls a flow of the digestate between at least two chambers of the plurality of chambers. The digestion substrate includes one or more microorganisms. The one or more microorganisms may be a hydrolytic, saccharolytic, proteolytic, lipolytic, nitrate reducers, nitrite reducers, iron reducers, manganese reducers, sulfate reducers, acidogenic, acetogenic, methanogenic, organic acid fermenters, alcohol fermenters, or any combination of these microorganisms.

The anaerobic digestion batch reactor may further include a heat source coupled to the plurality of chambers. The plurality of chambers may include a first portion comprising a first microorganism that is maintained at a first temperature by the heat source and a second portion comprising a second microorganism that is maintained at a second temperature. The plurality of chambers may include a first portion including at least one hydrolytic microorganism that is maintained at a first temperature by the heat source, a second portion including at least one acidogenic microorganism that is maintained at a second temperature, a third portion including at least one acetogenic microorganism that is maintained at a third temperature, and a fourth portion including at least one methanogenic microorganism that is maintained at a fourth temperature.

The plurality of chambers may include at least one gas sample port from which to withdraw gas. The gas sample ports may be coupled to a gas analyzer that analyzes gas withdrawn from the plurality of chambers. The anaerobic digestion batch reactor may further include a gas and mass flow control assembly that controls the flow of gases and digestate between the plurality of chambers based on the gas analysis of the gas analyzer.

The first biomaterial may include a chemical oxygen demand per liter from about 1 gram to about 3,000 grams and volatile solids content per liter from about 1 gram to about 200 grams. The second biomaterial may include a material that allows for a solid organic loading rate from about 0.01 grams of volatile solids per liter-day to about 250 grams of volatile solids per liter-day.

The plurality of chambers of the anaerobic digestion batch reactor may include at least one probe that measures at least one of pH or oxidation-reduction potential. The probes may be coupled to a chemical feed control assembly including at least one chemical supply tank. The chemical feed control assembly controls release of a chemical agent stored in the chemical feed control assembly. The plurality of chambers may be arranged in a serpentine configuration.

In yet another aspect, the present disclosure features an anaerobic digestion batch reactor. The anaerobic digestion batch reactor includes a plurality of chambers including a first portion and a second portion. The plurality of chambers is in fluid communication with each other and provide for the flow of digestate through the plurality of chambers. The anaerobic digestion batch reactor also includes a digestion substrate disposed within the first and second portions of the plurality of chambers. The first portion of the plurality of chambers includes at least one first microorganism and the second portion of the plurality of chambers includes at least one second microorganism. The anaerobic digestion batch reactor also includes at least one flow control mechanism, such as a control valve or a sluice gate that controls a flow of the digestate between the first and second portions of the plurality of chambers.

The at least one first microorganism and the at least one second microorganism may be different and may include a hydrolytic, saccharolytic, proteolytic, lipolytic, nitrate reducers, nitrite reducers, iron reducers, manganese reducers, sulfate reducers, acidogenic, acetogenic, methanogenic, organic acid fermenters, alcohol fermenters, or any combination of these microorganisms.

The anaerobic digestion batch reactor may further include a heat source coupled to the plurality of chambers. The first portion of the plurality of chambers may be maintained at a first temperature by the heat source and the second portion of the plurality of chambers may be maintained at a second temperature by the heat source. Each of the first and second portions of the plurality of chambers may include at least one gas sample port from which to withdraw gas. The gas sample ports are coupled to a gas analyzer that analyzes gas withdrawn from each of the first and second portions of the plurality of chambers. The anaerobic digestion batch reactor may further include a gas and mass flow control assembly that controls the flow of gases and digestate between the first and second portions of the plurality of chambers based on the gas analysis of the gas analyzer.

Each of the first and second portions of the plurality of chambers may include at least one probe that measures pH, oxidation-reduction potential, or both. The probes may be coupled to a chemical feed control assembly including at least one chemical supply tank. The chemical feed control assembly may control release of a chemical agent stored in the at least one chemical supply tank to maintain at least one of pH or oxidation-reduction potential within the first portion of the plurality of chambers at a first value and the second portion of the plurality of chambers at a second value. The pH within the first and second portions of the plurality of chambers may be maintained from about 3 to about 10. Also, the oxidation-reduction potential within the first and second portions may be maintained from about −500 mV to about +50 mV.

In yet another aspect, the present disclosure features an anaerobic digestion clarifier. The anaerobic digestion clarifier includes a first receptacle and a second receptacle that are in communication with each other and that are interconnected by a first opening. The first receptacle receives a first biomaterial and the second receptacle receives a second biomaterial. The first opening is disposed above a floor of the first receptacle to allow for retention of solid contents within the first receptacle while draining liquid contents into the second receptacle via the first opening.

The first and second receptacles of the anaerobic digestion clarifier may be coupled to a heat source that maintains the first receptacle at a first temperature and the second receptacle at a second temperature to pasteurize the first and second biomaterials. The first and second temperatures may be the same or different and may be from about 25° C. to about 60° C.

The anaerobic digestion clarifier may further include a second opening interconnecting the first and second receptacles and a pump coupled to the second opening. The first and second openings may be opened and the pump may be activated to selectively mix the first and second biomaterials within the first and second receptacles to form a digestate. The anaerobic digestion clarifier may further include a third receptacle in fluid communication with at least one of the first receptacle or second receptacle. The third receptacle may receive the digestate. A floor of the third receptacle may be disposed below the floor of at least one of the first receptacle or second receptacle to enable mixing of digestate as it flows from at least one of the first receptacle or second receptacle to the third receptacle.

The anaerobic digestion clarifier may further include a first biological reactor coupled to the first receptacle and including at least one first microorganism, and a second biological reactor coupled to the second receptacle and including at least one second microorganism. The at least one first organism may be an acidogenic microorganism. The at least one second organism may be a hydrolytic microorganism. The second biological reactor may be coupled to the third receptacle and may be configured to receive the digestate.

In yet another aspect, the present disclosure features a method for anaerobic digestion. According to the method, a first biomaterial is received at a first receptacle of a clarifier and a second biomaterial is received at a second receptacle of the clarifier. The first and second biomaterials are then pasteurized at a temperature from about 40° C. to about 250° C. for about 3 minutes to about 12 hours. Also, the first biomaterial is placed into contact with at least one first microorganism and the second biomaterial is placed into contact with at least one second microorganism within the clarifier. Then, the first and second biomaterials are selectively mixed within the first and second receptacles to form a digestate. The first and second biomaterials may be pasteurized by injecting steam into the first and second biomaterials.

According to the method for anaerobic digestion, at least one first microorganism may be stored within a first biological reactor and the at least one second microorganism may be stored within a second biological reactor. The first biological reactor may be coupled to the first receptacle and the second biological reactor may be coupled to the second receptacle. The first biomaterial may include fats-oils-greases (FOG), slaughterhouse waste, winery waste, municipal waste, animal manures, domestic sludge waste, coffee waste water, chemical waste, and combinations thereof, and may include a chemical oxygen demand per liter from about 1 gram to about 3,000 grams and volatile solids content per liter from about 1 gram to about 200 grams. The at least one first microorganism may be an acidogenic microorganism. The second biomaterial may include energy crops, post-harvest crops, post-consumer waste, non-hazardous laboratory waste, construction and demolition waste, post-consumer waste, animal by-products, food waste, residual waste, forestry waste, municipal solids, and combinations thereof, and may allow for a solid organic loading rate from about 0.01 grams of volatile solids per liter-day to about 250 grams of volatile solids per liter-day. The at least one first microorganism may be a hydrolytic microorganism.

The method for anaerobic digestion may further include transferring the digestate from at least one of the first receptacle or second receptacle to a third receptacle and transferring the digestate from the third receptacle to the second biological reactor.

In yet another aspect, the present disclosure features an anaerobic digester. The anaerobic digester includes an enclosed reactor that collects at least one gas generated during anaerobic digestion of the digestate. The anaerobic digester also includes a flexible inlet that supplies digestate into the enclosed reactor and that floats at least partially on the surface of the digestate within the enclosed reactor. The anaerobic digester further includes at least one gas diffuser disposed within the reactor that recirculates the at least one gas through the enclosed reactor. The enclosed reactor may include a floor, a plurality of walls, and a stretchable cover. The anaerobic digester may further include at least one circulation piping loop coupled to a heat source that maintains a temperature within the enclosed reactor from about 25° C. to about 60° C. The flexible inlet may include a flexible portion coupled to a source of the digestate and a rigid portion including first and second segments disposed in a Y-shaped configuration with respect to the flexible portion. The rigid outlet portion projects the digestate stream in at least two directions.

In yet another aspect, the present disclosure features an anaerobic digester. The anaerobic digester includes an enclosed reactor, a gas take-off in fluid communication with the enclosed reactor, at least one scrubber coupled to the gas take-off, and a flow control mechanism. The at least one scrubber removes at least one undesirable gas including hydrogen sulfide, ammonia, carbon dioxide, nitrogen, and any combinations of these undesirable gases. The flow control mechanism recirculates the gas output from the scrubber into the enclosed reactor.

The gas take-off may provide the at least one gas as a source of fuel to a heat source configured to maintain the reactor at a temperature from about 25° C. to about 60° C. The anaerobic digester may further include at least one methanogenic microorganism.

In yet another aspect, the present disclosure features a method for anaerobic digestion. According to the method, a digestate is supplied into an enclosed reactor and at least one gas collected within the enclosed reactor is withdrawn. Then, the at least one gas is recirculated within the enclosed reactor through at least one diffuser. The enclosed reactor may include at least one methanogenic microorganism.

The method for anaerobic digestion may further include maintaining a temperature within the enclosed reactor from about 25° C. to about 60° C. The method may further include supplying the at least one gas as a source of fuel to a heat source configured to maintain the enclosed reactor at a temperature from about 25° C. to about 60° C. The method may further include passing the at least one gas through at least one scrubber to remove at least one undesirable gas including hydrogen sulfide, ammonia, carbon dioxide, and any combination of these undesirable gases.

The digestate may be supplied to the enclosed reactor by injecting the digestate into the enclosed reactor through a flexible inlet. The flexible inlet may include a flexible portion and a rigid portion. The flexible portion is coupled to a source of the digestate. The rigid portion includes first and second segments in a Y-shaped configuration with respect to the flexible portion. In this configuration, the rigid portion projects the digestate stream in at least two directions.

In yet another aspect, the present disclosure features a control system for a digestion system. The control system includes a flow control system, at least one sensor, and a controller. The flow control system includes a first flow control mechanism that control the flow of material through the digestion system and a second flow control mechanism that controls the flow of at least one chemical agent to the material. The at least one sensor senses at least one property of the material including ORP, pH, temperature, pressure, composition, or any combination of these properties. The controller controls the flow control system based on the at least one property of the material.

The controller may be a logic controller, a programmable logic controller, a logic circuit, a field programmable gate array, or a computer. The flow control system may include a movement control system that control the flow rate of material in the digestion system and a directional control system that control the flow direction of the material in the digestion system.

The control system may further include a temperature control system that controls the temperature of the material. The digestion system may include a collection tank, a clarifier, a batch reactor, a biological reactor, and a digester. The flow control system may include a directional control system that controls the flow of material from the clarifier to both the digester and the batch reactor simultaneously. The clarifier and the batch reactor may each include a level sensor and the flow control system may transfer material from the clarifier to the batch reactor based on a material retention period for the clarifier and the batch reactor and the material levels measured by the level sensors.

The digestion system may further include an influent collection tank having a level sensor, the clarifier and the batch reactor each having a level sensor. The movement control system may transfer biomaterial from the influent collection tank to the clarifier based on a material retention period for the clarifier and/or the batch reactor and material levels measured by the level sensors. The clarifier and the batch reactor may each include a level sensor and the directional control system may control the direction of material flow from the clarifier based on a material retention period for the clarifier and/or the batch reactor and the material levels measured by the level sensors. The digestion system may include a clarifier and a batch reactor.

The first flow control mechanism may be a pump, a blower, a valve, or a gate. The gate may be a fluid-actuated gate and the valve may be a fluid-actuated valve. The flow control system may further include a fluid pump operably coupled to the fluid-actuated gate and the fluid-actuated valve.

The flow control system may recirculate material through at least one portion of the digestion system. The flow control system may also recirculate material between the clarifier and the digester. The flow control system may further continuously cycle between periods of recirculation and non-recirculation. The flow control system may further recirculate material through the batch reactor or recirculate gas through the digester.

The temperature control system may include a temperature sensor that senses the temperature of the material and a temperature sensor that senses a temperature of a fluid flowing through a heat exchanger disposed within the material. The temperature control system may control the temperature of the fluid flowing through the heat exchanger based on the temperatures measured by the temperature sensors.

The material may include gas and the flow control system may transfer the gas from a reactor to another location based on at least one of the composition of the gas and the pressure of the gas. The material may include gas and the flow control system may transfer gas from a reactor to a gas storage vessel, a flare, or an evacuation vent based on at least one of the composition of the gas and the pressure of the gas within the reactor.

The logic controller may control the amount of gas produced by the anaerobic digestion system to meet the heat loads and electrical loads of the anaerobic digestion system or external systems by controlling the flow control system and the temperature control system. The control system may include a totalization system including a gas pressure sensor that measures gas pressure. The flow control system may control the amount of a gas transferred from a reactor of the anaerobic digestion system based on at least one of the gas pressure measured by the gas pressure sensor and the composition of the gas.

The temperature control system may include a material heat exchanger fluidly coupled to an output of a batch reactor and fluidly coupled to an output of the collection tank. The material heat exchanger may enable the transfer of heat from a material output from the batch reactor to a material output from the collection tank.

In yet another embodiment, the present disclosure features a control system for an anaerobic digestion process. The control system includes a totalization system that senses the volume of material in at least one stage of the anaerobic digestion process including hydrolysis, acidogenesis, acetogenesis, and methanogenesis, or any combination of these stages. The control system also includes a processor that determines a total energy potential of the material based on the sensed volume and composition of the material.

The control system may further include a flow control system that controls the flow of material through the digestion system and a controller that controls the flow control system based on the total energy potential of the material. The flow control system may control at least one of the amount of gas transferred between reactors of the anaerobic digestion system, the amount of gas re-circulated within a reactor of the anaerobic digestion system, the amount of gas converted to heat, the amount of gas converted to electricity, or the amount of gas flared.

The totalization system may include a conductivity meter and a pressure sensor coupled to a reactor. The flow control system may retain material within the reactor when the conductivity of the material measured by the conductivity meter has not reached a predetermined conductivity within a retention period. The flow control system may enable transfer of the material to another reactor when the conductivity measured by the conductivity meter reaches the predetermined conductivity. The flow control system may control the flow of a chemical agent into the reactor based on the conductivity of the material measured by the conductivity meter. The conductivity meter may include an ORP meter and a pH meter. The totalization system may further include a total organic carbon analyzer and/or a gas chromatograph.

In yet another aspect, the present disclosure features a control system for an anaerobic digestion system. The control system includes a first flow control mechanism that controls the flow of at least one chemical agent to a material contained within a clarifier to form a digestate. The control system also includes a second flow control mechanism that controls the flow of digestate from the clarifier to a batch reactor. The control system also includes a third flow control mechanism that controls the flow of digestate through the batch reactor, which includes a plurality of chambers that are in fluid communication with each other.

The control system may further include a fourth flow control mechanism that removes at least one gas generated during anaerobic digestion within the clarifier and the batch reactor. The fourth flow control mechanism may further provide the at least one gas to a digester. The control system may further include a fifth flow control mechanism that transfers the digestate from the batch reactor to the digester. The control system may further include a sixth flow control mechanism that transfers the digestate from the digester to the clarifier.

In yet another aspect, the present disclosure features a method of controlling a digestion system. According to the method, one or more properties of a material in the digestion system is sensed. The one or more properties includes ORP, pH, temperature, pressure, composition, and combinations thereof. Then, the flow of one or more chemical agents to the material is controlled. The flow of the material through the digestion system is also controlled based on the one or more properties of the material.

The flow of the material may include the flow rate of the material and the flow direction of the material. The digestion system may be a clarifier, a batch reactor, a digester, and combinations thereof.

The method may further include determining the volume of the material and controlling the flow of the material based on the volume of the material. The method may still further include determining a total energy potential of the material based on the volume of the material and the composition of the material, and controlling the flow of the material through the digestion system based on the total energy potential of the material.

Controlling the flow of the material may include controlling the flow of gas from the digestion system to a gas storage vessel, a flare, or an evacuation vent based on at least one of the composition of the gas and the pressure of the gas within the digestion system. Controlling the flow of the material may alternatively include controlling the amount of gas produced by the digestion system to meet heat loads and electrical loads of the digestion system or external systems. Controlling the flow of the at least one chemical agent may include controlling the flow of one or more chemical agents based on one or more properties of the material including ORP, pH, or both.

BRIEF DESCRIPTION OF THE DRAWINGS

Various embodiments of the present disclosure are described herein with reference to the drawings wherein:

FIG. 2A is a plan, cross-sectional view of an influent collection tank according to the present disclosure;

FIG. 2B is a side, cross-sectional view of the influent collection tank of FIG. 2A as taken along section 2B-2B of FIG. 2A;

FIG. 6A is a plan, cross-sectional view of a batch reactor according to the present disclosure;

FIGS. 6B and 6C are side, cross-sectional views of the batch reactor of FIG. 6A taken along section lines 6B-6B and 6C-6C, respectively;

FIG. 9 is a plan, cross-sectional view of the batch reactor of FIG. 6A including heat exchange piping according to the present disclosure;

FIG. 10 is a plan, cross-sectional view of a digester according to the present disclosure;

DETAILED DESCRIPTION

Particular embodiments of the present disclosure are described hereinbelow with reference to the accompanying drawings. In the following description, well-known functions or constructions, such as piping runs, valves, pumps, fans, and the like are not described in detail to avoid obscuring the present disclosure in unnecessary detail. Further, the process according to the present disclosure may optionally be performed as a serial, continuous, or batch process, and combinations thereof (e.g., sequential or continuous batch processing). The following description and figures illustrate non-limiting embodiments of an anaerobic digestion system that may comprise any number of clarifiers, batch reactors, and digesters, among other aspects.

Figure 1:
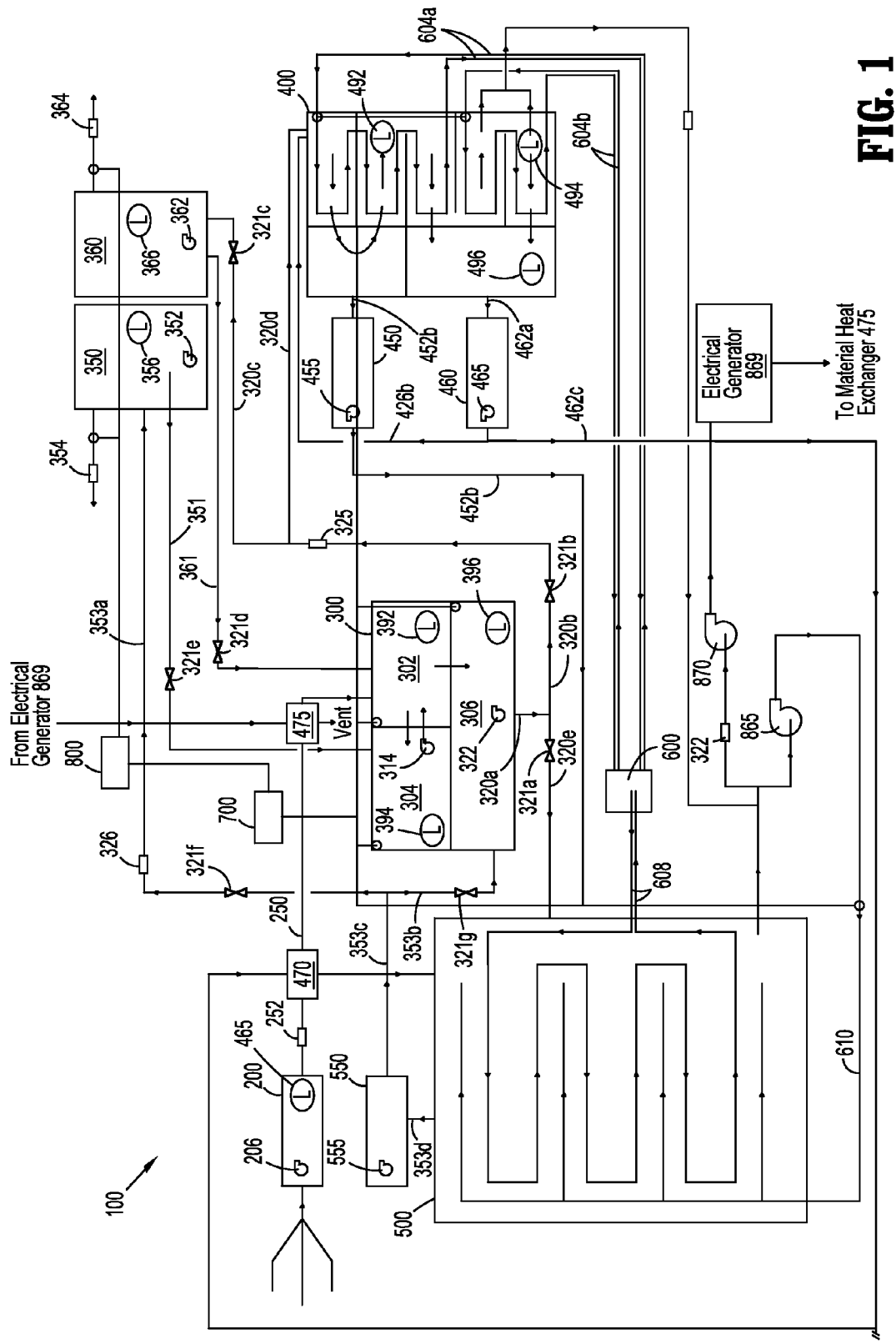
FIG. 1 is a schematic diagram of an anaerobic digestion system according to the present disclosure.

FIG. 1 illustrates an embodiment of an anaerobic digestion system 100 of the present disclosure. As shown in FIG. 1, the system 100 may include an influent collection tank 200, a clarifier 300, a batch reactor 400, and a digester 500. As shown in FIG. 1, in certain embodiments, the anaerobic digestion system 100 may also comprise one or more biological reactors 350 and 360, which may be used for testing purposes. As used herein the term "clarifier" denotes any receptacle in which predigestion or pretreatment processing of at least one biomaterial may occur. Pretreatment processing may include homogenization, hydrolysis, including mechanical or acid treatment, pasteurization, and combinations thereof. As used herein, the term "batch reactor" denotes any receptacle that may also contain a digestion substrate (e.g., fixed and/or fluidized media) in which anaerobic digestion may occur. As used herein, the term "digester" denotes any receptacle in which anaerobic digestion may occur. As used herein the term "biological reactor" denotes any receptacle in which materials for the predigestion processing of at least one biomaterial, processes or partially processed digestate, and/or test samples of the foregoing may be housed for later use or analysis. As used herein, the term "receptacle" denotes any containment vessel system or systems including one or more chambers, containers, compartments, sections, tanks, vessels, reactors, housings, structures, and combinations thereof.

In some embodiments, the batch reactor 400 is a stand-alone anaerobic digestion system that operates without the clarifier 300, the biological reactors 350, 360, or the digester 500. In these embodiments, digestate may be fed to the batch reactor 400 from a digestate storage vessel (not shown) that stores preprocessed biomaterial. In other embodiments, the anaerobic digestion system includes the clarifier 300 and the batch reactor 400 and not the biological reactors 350, 360, or the digester 500. In yet other embodiments, the clarifier 300 includes only two receptacles: a biomaterial receptacle and a digestate receptacle. In these embodiments, the receptacles may be positioned immediately adjacent to each other or positioned apart from each other, but fluidly coupled to each other via a fluid line, such as a pipe. In still other embodiments, the anaerobic digestion system includes the clarifier 300 and the digester 500 and not the biological reactors 350, 360, or the batch reactor 400.

FIGS. 2A and 2B show plan and cross-sectional views of an embodiment of the influent collection tank 200, respectively. The collection tank 200 may be constructed of concrete and may include a floor, walls, and a ceiling. The collection tank 200 includes an inlet 202 for supplying a first biomaterial to be digested by the digestion system 100. The first biomaterial may include biomaterial that is generally in sludge or slurry form, and/or biomaterial having a nonzero chemical oxygen demand. In embodiments, the first biomaterial may include agricultural and industrial waste. In further embodiments, the biomaterial may include fats-oils-greases (FOG), slaughterhouse waste, winery waste, municipal waste, animal manures, domestic sludge waste, coffee waste water, chemical waste, and combinations thereof. In yet further embodiments, the first biomaterial may include any human or animal excrement, for example, livestock manure produced by any domesticated animals including, but not limited to, swine; horses; poultry, such as chickens, ducks, and geese; cattle, such as cows, steer, yaks, goats, and buffalo; and combinations thereof. The biomaterial may have a chemical oxygen demand (COD) per liter from about 1 gram to about 3,000 grams, in embodiments from about 10 grams to about 500 grams, in further embodiments from about 20 grams to about 100 grams. The biomaterial may also have volatile solids (VS) contents per liter from about 1 gram to about 200 grams, in embodiments from about 10 grams to about 150 grams, in further embodiments from about 15 grams to about 60 grams.

The inlet 202 terminates within the collection tank 200 and directs the flow of the first biomaterial (e.g., influent) through a screen filter 204. The screen filter 204 has a three-dimensional mesh structure configured to prevent any inorganic materials (e.g., rocks, catheters, needles, steel flooring particles, steel piping particles, plastics, mortalities, and the like) from entering the system 100. The collection tank 200 also includes a pump 206, which may be a submersible pump that is disposed at the bottom of the collection tank 200. The pump 206 is configured to remove the influent from the collection tank 202 and supply the influent to the clarifier 300. The pump 206 is coupled to piping 250 for pumping out the influent stored in the collection tank 200. The pump 206 may be operated automatically or manually (e.g., by a user).

The collection tank 200 may also include a float sensor 210, which provides fill level measurements to the system 100 including low and high fill level warnings. The low fill level warning may be used to prevent operation of the pump 206 and the high fill level may be used to prevent further addition of the influent into the collection tank 200. Automatic operation of the pump 206 may also be based on a variety of sensor readings regarding the state of the system 100 as described in further detail below, including but not limited to, the operational state (e.g., fill level) of the clarifier 300, the batch reactor 400, and the digester 500. The load of the pump 206 is also measured by one or more sensors and is provided to the system 100. The load may be calculated by measuring the voltage and the current of the supplied electrical energy to determine input power.

In some embodiments, a single sensor is used to obtain multiple different data points. For example, the pressure transducer 225 shown in FIG. 2 generates pressure sensor data that may be used to determine both the volume of the gas within the headspace of the influent collection tank 200 and the volume of liquid biomaterial within the influent collection tank 200.

The pressure sensor assembly 220 includes a pipe 224 that extends from the floor of the influent collection tank 200 to the headspace of the influent collection tank 200, where the pipe 224 bends at a right angle and couples to an aperture in a side wall of the influent collection tank 200. The pressure sensor assembly 220 includes a first conduit 221 having one end that is coupled to an air chamber on a first side of a pressure sensing diaphragm within the pressure transducer 225. The other end of the first conduit 221 is coupled to a first breather tube 227 that passes through an aperture in the pipe 224 into the headspace of the influent collection tank 200. The pressure sensor assembly 220 also includes a second conduit 222 having one end that is coupled to an air chamber on a second side of the pressure sensing diaphragm (opposite the first side). The other end of the second conduit 222 is coupled to a second breather tube 228 that passes through the aperture in the side wall of the influent collection tank 200 and is vented to atmosphere.

Before normal operation, the pressure sensor assembly 220 is calibrated by acquiring pressure sensor signals from the pressure transducer 225 and determining the signal-to-noise ratio of the pressure sensor signals when the influent collection tank 200 is empty and when the influent collection tank 200 is full. During normal operation, a logic controller 802 (described below) acquires pressure sensor signals from the pressure transducer 225 and determines the signal-to-noise ratio of the pressure sensor signals. The logic controller 802 then uses the signal-to-noise ratio information to determine both the volume of the gas and the volume of the liquid within the influent collection tank 200. The pressure sensor assembly 220 may be disposed in other reactors of the digestion system 100 to obtain volume data.

The collection tank 200 is in fluid communication with the clarifier 300 via piping 250. A flow meter 252 (in FIG. 1) is coupled to the piping 250, which is adapted to measure the flow rate of the influent therethrough. The flow rate measurement provides for a total volume of the influent. The system 100 may then determine the solid contents of the influent supplied to the clarifier 300 based on the flow rate and the load of the pump 206.

With reference to FIG. 1, in embodiments, the clarifier 300 may include a first biomaterial (e.g., influent) intake receptacle 302, a second biomaterial (e.g., biomass) intake receptacle 304, and a digestate receptacle 306. The clarifier 300 may be constructed as an in-ground, explosion-proof tank from concrete and/or other suitable materials. The clarifier 300 may include a floor, walls, and a ceiling. The clarifier 300 includes a wall 305 partitioning the clarifier into two portions, the receptacles 302, 304 and the receptacle 306, and a wall 303 partitioning the receptacles 302 and 304. The receptacles 302, 304, and 306 are in fluid communication with each other to allow for influent to pass therebetween as described in further detail below. In embodiments, the receptacles 302, 304, 306 may be constructed as stand-alone structures interconnected by piping. In further embodiments, the clarifier 300 may include a single receptacle for predigestion processing.

The receptacles 302 and 306 may have a reactor volume from about 1 gallon to about 5,000,000 gallons, in embodiments, from about 1,000 gallons to about 1,000,000 gallons, in further embodiments from about 5,000 gallons to about 20,000 gallons. The receptacle 304 may have a reactor volume from about 1 gallon to about 5,000,000 gallons, in embodiments, from about 1,000 gallons to about 1,000,000 gallons, in further embodiments from about 5,000 gallons to about 10,000 gallons.

Figure 3C:
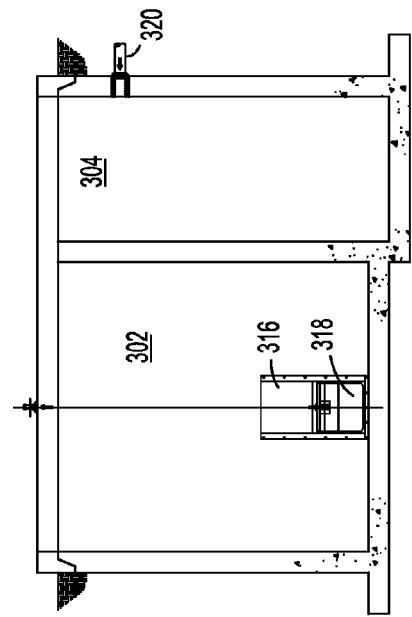
FIGS. 3B and 3C are side, cross-sectional views of the clarifier of FIG. 3A taken along section lines 3B-3B and 3C-3C, respectively.
Figure 3A:
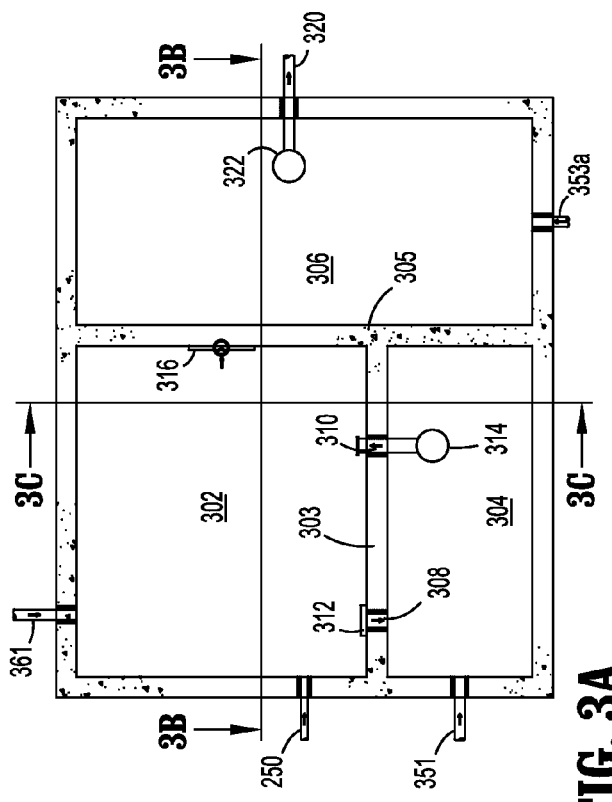
FIG. 3A is a plan, cross-sectional view of a clarifier according to the present disclosure.
Figure 3B:
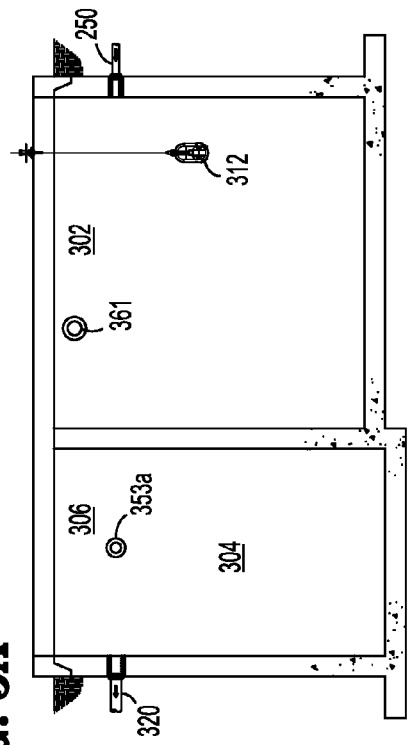

FIGS. 3A, 3B, and 3C show plan and cross-sectional views of an embodiment of the clarifier 300 taken along section lines 3B-3B and 3C-3C, respectively. In embodiments, the piping 250 is coupled to the receptacle 302 to provide for the flow of the influent. The receptacle 302 operates as a raw influent slurry acceptance stage, and is used for, but is not limited to, pasteurization, solid particle size reduction, calibration of volatile solids and chemical oxygen demand, and combinations thereof.

In embodiments, the second biomaterial, e.g., biomass, is also added to the intake receptacle 304. As used herein, the term "biomass" denotes any organic material including, but not limited to, silage, such as foliage, grasses, hay, straw, grains, legumes, and the like; compost; animal waste products, such as human waste and livestock manure having a desired amount of solids content. The amount of biomass added may be based on the amount of solid contents of the influent in the receptacle 302. Solid organic loading rate of the biomass may be from about 0.01 grams of volatile solids per liter-day ($g*VS/L*D^{-1}$) to about 250 $g*VS/L*D^{-1}$, in embodiments from about 0.05 $g*VS/L*D^{-1}$ to about 100 $g*VS/L*D^{-1}$, in further embodiments from about 0.1 $g*VS/L*D^{-1}$ to about 5 $g*VS/L*D^{-1}$.

In embodiments, the second biomaterial may include biomaterial that is in solid, semi-solid, or slurry form, and/or biomaterial that contains volatile solids. The second biomaterial may include energy crops, post-harvest crops, post-consumer waste, non-hazardous laboratory waste, construction and demolition waste, post-consumer waste, animal by-products, food waste, residual waste, forestry waste, municipal solids, and combinations thereof.

The receptacle 304 may include a recirculation chopper pump 314 configured to chop the biomass thereby reducing the particle size of the biomass. The pump 314 may be activated to circulate and process the biomass as the biomass is subjected to various treatment processes described below. The receptacle 304 operates an anaerobic hydraulic flush reactor (AHFR) as part of a two-stage process in series with the batch reactor 400, which operates as a stationary bed anaerobic fixed film reactor (AFFR) as described in further detail below.

Once the receptacles 302 and 304 are loaded with the influent and biomass, respectively, the influent and the biomass are pasteurized. Pasteurization of the influent and the biomass removes microorganisms found therein, such as enteric species found in the digestive tract of animals. This provides for optimal inoculation of the influent and the biomass with desired microorganisms suitable for anaerobic digestion as described in further detail below.

The digestion system 100 includes a heat source 600, which may be any suitable boiler, and multiple heat exchangers (e.g., the heat exchangers 632a-c, 634a-b, 636a-b, 608a-d of FIG. 6) configured to heat the material being processed to a desired temperature. A variety of different heat exchanger configurations may be used, including, but not limited to, a sleeve heater, in-line heater or a heater provided within the walls, floor, and/or ceiling of the clarifier 300, the batch reactor 400, and the digester 500. The heating elements may be designed to heat specific zones or regions of the system 100.

In some embodiments, the heat source 600 may be coupled to a steam generator (e.g., the steam generator 1727 of FIG. 17), which, in turn, may be coupled to one or more steam injectors that inject steam into the clarifier 300. A plurality of temperature sensors (e.g., the temperature sensors 642a-c, 644a-b, 646a-b, 648, 652a-c, 654a-b, 656a-b, 658 of FIG. 6) may be dispersed throughout the digestion system 100. The logic controller 802 may be coupled to the temperature sensors and heat exchangers to provide continuous, regulated heating of the clarifier 300, the batch reactor 400, and the digester 500 by regulating the output of the heat source 600.

Figure 4:
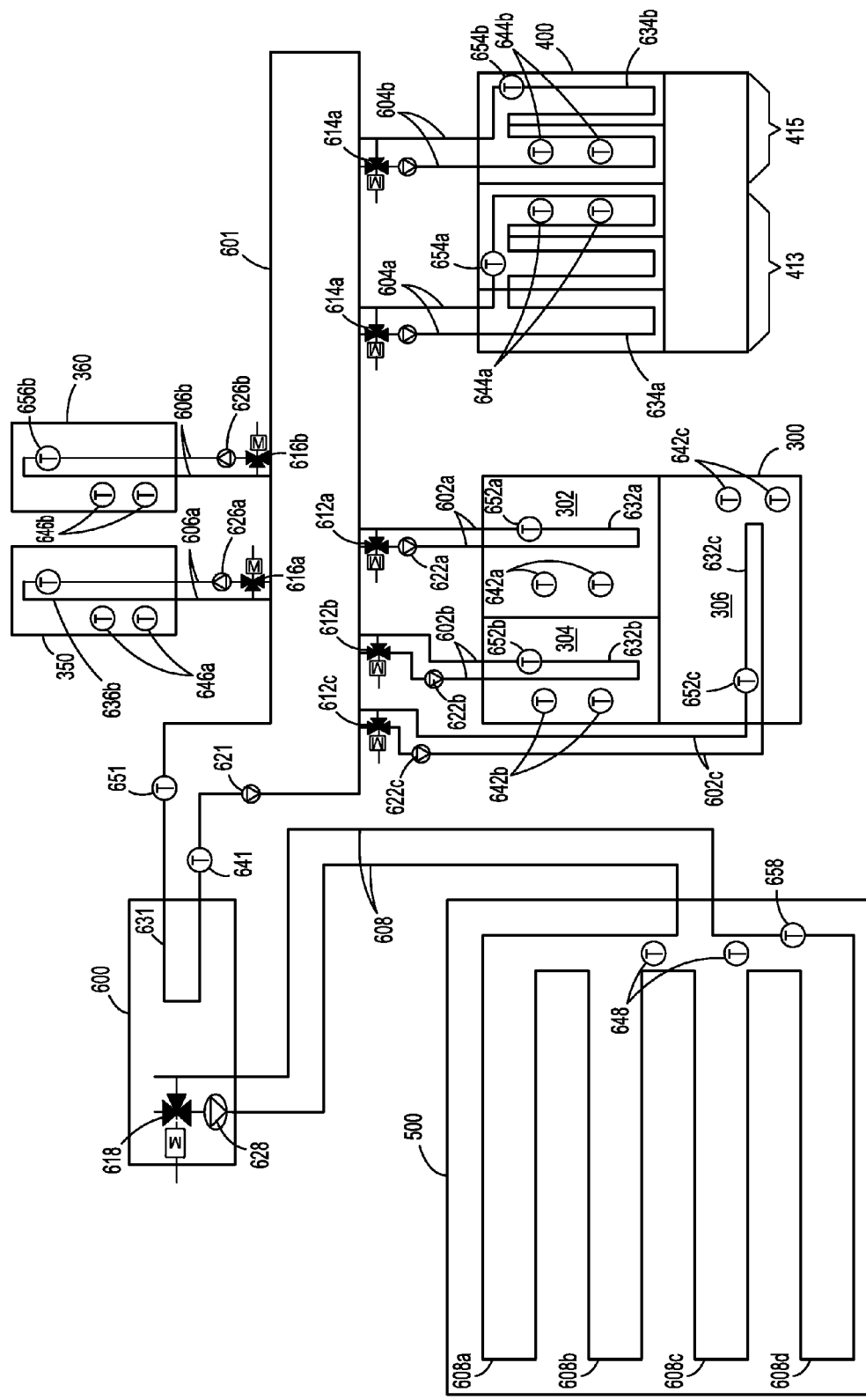
FIG. 4 is a schematic diagram of a heat source system according to the present disclosure.

With reference to FIG. 4, the heat source 600 includes a plurality of closed-loop pipe runs configured to circulate a heating medium, such as water, vapor, oil, and the like. The heat source 600 is coupled to heat exchange piping that is disposed within the clarifier 300. In embodiments, the heat exchange piping may include a plurality of zones 602a, 602b, 602c disposed within the walls of the receptacles 302, 304, 306, respectively. Each of the zones 602a, 602b, 602c may be heated to a desired temperature to provide optimal conditions within each of the receptacles 302, 304, 306.

Pasteurization may occur by heating the influent and the biomass within the receptacles 302 and 304, respectively, to a temperature from about 40° C. to about 250° C., in embodiments from about 45° C. to about 100° C., and in further embodiments from about 50° C. to about 80° C. via the zones 602a and 602b for a time period from about 3 minutes to about 12 hours, in embodiments from about 30 minutes to about 4 hours, in further embodiments from about 1 hour to about 3 hours until pasteurization is achieved. The dwell time and temperature may be varied to achieve optimal pasteurization. After pasteurization, the receptacles 302 and 304 may be maintained at a temperature from about 25° C. to about 50° C., in embodiments from about 30° C. to about 40° C., and in further embodiments from about 35° C. to about 38° C.

With reference to FIG. 1, in addition to the temperature within the receptacles 302 and 304, the pH and oxidation reduction potential (ORP) of the contents thereof is also measured and maintained at a desired level. The system 100 includes a chemical feed control assembly 700 which is configured to measure and adjust pH and ORP of the material being processed by the system 100. The system 100 may include a plurality of pH and ORP sensors and a plurality of chemical feed inlets dispersed throughout various components of the digestion system 100, e.g., the clarifier 300, the batch reactor 400, etc. The plurality of chemical inlets are coupled to the chemical feed control assembly 700 that is configured to introduce acidic or basic compounds to the suspension of solid waste to control the pH and ORP.

Figure 5:
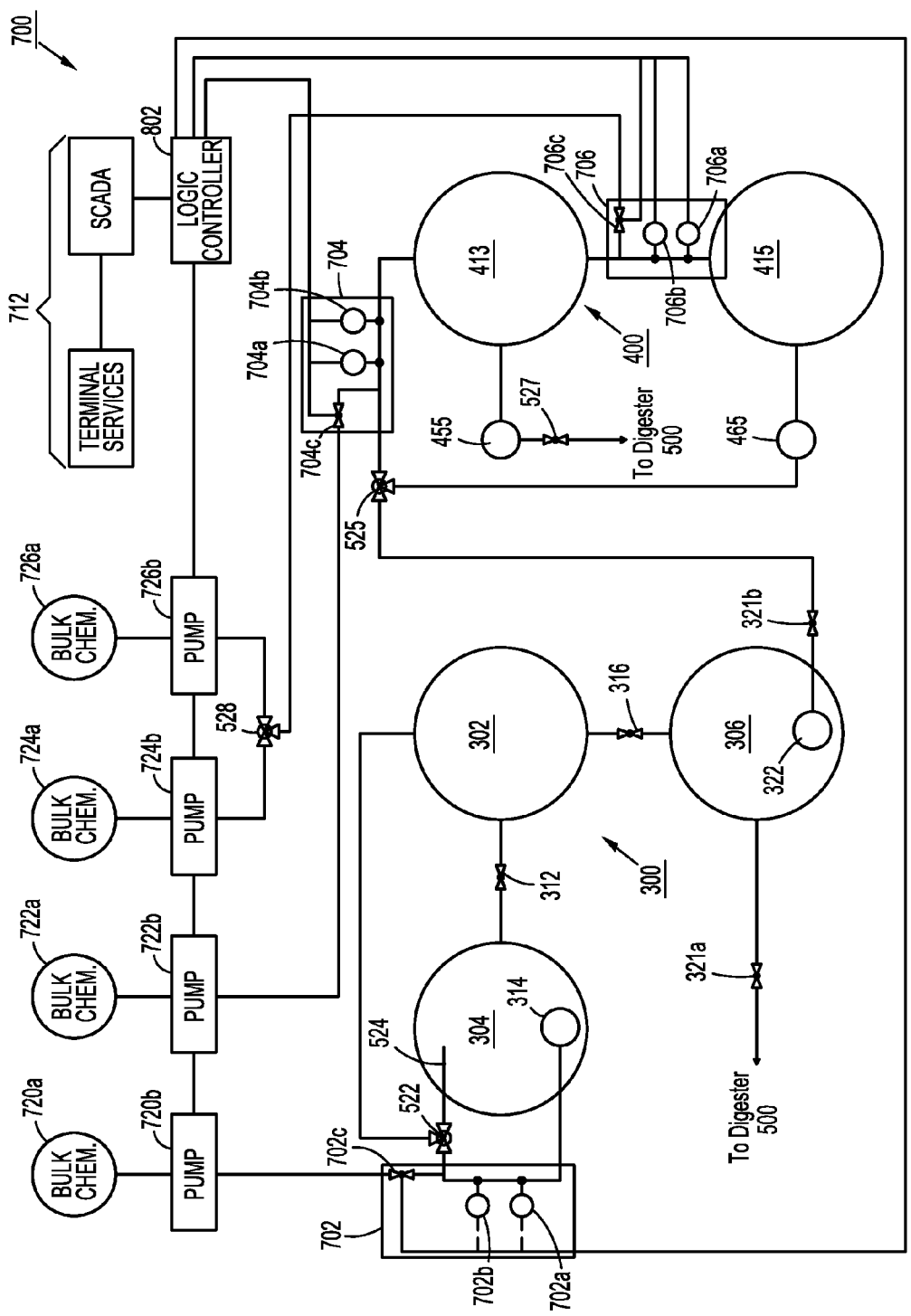
FIG. 5 is a schematic diagram of a chemical feed controller according to the present disclosure.

With reference to FIG. 5, the chemical feed control assembly 700 includes a plurality of probes 702, 704, 706 configured to measure pH and/or ORP of the contents stored within the clarifier 300 and the batch reactor 400. Each of the probes 702, 704, 706 includes a pH sensor 702a, 704a, 706a, an ORP sensor 702b, 704b, 706b, and a control valve 702c, 704c, 706c. The chemical feed control assembly 700 also includes a plurality of chemical supply tanks 720a, 722a, 724a, 726a which store specific compounds suitable for adjusting pH and ORP of the material being processed by the system 100. Each of the chemical supply tanks 720a, 722a, 724a, 726a is coupled to a corresponding pump 720b, 722b, 724b, 726b. The chemical feed control assembly 700 includes the logic controller 802, which may be any suitable logical processing unit embodied as hardware, including but limited to, a processor, a field programmable gate array, a logic circuit, a programmable logic controller (PLC), and the like, or software, such as a virtual processing environment. The logic controller 802 is coupled to the pumps 720b, 722b, 724b, 726b and the probes 702, 704, 706.

The chemical supply tanks 720a, 722a, 724a, 726a may include any suitable strong mineral acid, including, but not limited to, sulfuric acid, nitric acid, hydrochloric acid, hydrofluoric acid, perchloric acid, and combinations thereof, and any suitable strong mineral base, including, but not limited to, sodium hydroxide, calcium carbonate, potassium hydroxide, calcium hydroxide, magnesium hydroxide, and combinations thereof.

The logic controller 802 may also be coupled to a computerized control interface 712. In embodiments, the control interface 712 may include terminal services, industrial control and data acquisition interfaces, and other industrial control systems. The control interface 712 provides for local and/or remote (e.g., off site) user input and output. The logic controller 802 determines one or more suitable compounds to be added to system 100 based on the measurements by the probes 702, 704, 706. The logic controller 802 may interrogate the probes 702, 704, 706 at regular intervals and/or when specifically requested by a user via the control interface 712. In embodiments, the sampling may be controlled using a proportional integral derivative (PID) control loop based on a desired sampling rate, previously sampled pH and ORP values, set point pH and ORP values, and combinations thereof.

The logic controller 802 also calculates a desired rate of addition of the compounds to the system 100 to ensure that the compounds are added in a controlled manner. In embodiments, the rate of addition may be calculated based on the circulation rate of the pumps (e.g., pump 314). Based on the measurement by the probes 702, 704, 706, the logic controller 802 signals corresponding pumps 720b, 722b, 724b, 726b to release a desired amount of chemical feedstock at a desired rate. The logic controller 802 also controls operation of control valves 702c, 704c, 706c to allow for the flow of the chemical agents to a desired location within the system 100.

With reference to FIGS. 1 and 5, once the biomass is pasteurized, the pH and ORP of the biomass within the receptacle 304 is measured. The probe 702 is coupled to the pump 314, which provides a sample of the biomass within the receptacle 304 to the probe 702 for measuring pH and ORP of the biomass contained therein. The logic controller 802 signals the pump 720b to release a desired amount of chemicals from the tank 720a at a desired rate based on the measured pH and ORP values. In embodiments, the tank 720a may include, any strong mineral acid, including, but not limited to, sulfuric acid, hydrochloric acid, and any of the other acidic compounds described above including any combinations thereof. The pH of the biomass is adjusted to a value of from 2 to about 6, in embodiments from about 3 to about 5 by the chemical feed control assembly 700.

Once the pH is adjusted, hydrolysis of the biomass is commenced by introducing hydrolytic microorganisms into the receptacle 302 from a first biological reactor 350. The biological reactor 350 may have a reactor volume from about 1 gallon to about 5,000,000 gallons, in embodiments, from about 1,000 gallons to about 1,000,000 gallons, in further embodiments from about 5,000 gallons to about 10,000 gallons. The biological reactor 350 operates as a fermentation stage and a source of microorganisms, micronutrients, and inoculants for the processing of biomass within the receptacle 304. Hydrolytic microorganisms may be stored along with processed product, e.g., processed digestate, within the first biological reactor 350.

The biological reactor 350 is in fluid communication with the receptacle 304 via piping 351. The biological reactor 350 includes a recirculation pump 352 that is used to transport the contents of the biological reactor 350 to the receptacle 304. The pump 352 may also be activated periodically to cycle between periods of circulation and stationary storage.

With reference to FIG. 4, the biological reactor 350 also includes heat exchange piping 606a coupled to the heat source 600. The piping 606a may be disposed within or about the biological reactor 350 and is configured to maintain a desired temperature within the biological reactor 350 to provide optimum conditions for the hydrolytic (e.g., liquid contents) microorganisms disposed therein. The biological reactor 350 may be maintained at a temperature from about 10° C. to about 100° C., in embodiments from about 25° C. to about 50° C., in further embodiments from about 30° C. to about 40° C., in yet further embodiments from about 35° C. to about 38° C.

The first biological reactor 350 may include previously processed digestate which is used as nourishment to maintain desired levels of microorganisms within the biological reactor 350. In embodiments, the biological reactor 350 may be refilled from outside sources to maintain required levels of microorganisms. Suitable hydrolytic microorganisms include, but are not limited to, *Clostridium* species, such as *C. thermolacticum*, *C. thermohydrosulfuricum*, *C. thermosuccinogene*, *C. butyricum*, *C. pasteurianum*, and *C. beijirincki*; *Lactobacillus* species, such as *Lactobacillus paracasel*; and *Eubacteria* species, such as *E. aerogenes*; and combinations thereof. The solids and hydraulic retention time within the biological reactor 350 may be from about 30 minutes to about 40 days, in embodiments from about 1 hour to about 20 days, in further embodiments from about 4 hours to about 10 days, in yet further embodiments from about 6 hours to about 12 hours.

With reference to FIG. 1, after the influent is pasteurized within the receptacle 304, acidogenic microorganisms are introduced into the receptacle 302 to commence acidogenesis of the influent. The biological reactor 360 may also have a reactor volume from about 1 gallon to about 5,000,000 gallons, in embodiments, from about 1,000 gallons to about 1,000,000 gallons, in further embodiments from about 5,000 gallons to about 10,000 gallons. Similarly to the biological reactor 350, the biological reactor 360 operates as a fermentation stage and a source of microorganisms, micronutrients, and inoculants for the processing of the influent within the receptacle 302. The biological reactor 360 also operates as a quality control stage for inter-reactor transfers and effluent discharge as described in further detail below. Acidogenic microorganisms may be stored along with processed product, e.g., processed digestate, within the second biological reactor 360.

The biological reactor 360 is in fluid communication with the receptacle 304 via piping 361. The biological reactor 360 includes a pump 362 that is used to transport the contents of the biological reactor 360 to the receptacle 304. The pump 362 may also be activated periodically to cycle between periods of recirculation and stationary storage.

With reference to FIG. 4, the biological reactor 360 also includes heat exchange piping 606b coupled to the heat source 600. The piping 606b may be disposed within or about the biological reactor 360 and is configured to maintain a desired temperature within the biological reactor 360 to provide optimum conditions for the acidogenic microorganisms disposed therein. The biological reactor 360 may be maintained at a temperature from about 10° C. to about 100° C., in embodiments from about 30° C. to about 80° C., in further embodiments from about 35° C. to about 75° C., in yet further embodiments from about 40° C. to about 60° C.

The biological reactor 360 also includes a pump 362, which may be activated periodically to cycle between periods of circulation and stationary storage. The second biological reactor 350 may also include previously processed digestate. In embodiments, the biological reactor 360 may be refilled from outside sources. Suitable acidogenic microorganisms include, but are not limited to, *Syntrophobacter* species, such as *S. fumaroxidans, S. pfennigii, S. sulfatireducens, S. wolinii*, and combinations thereof. The solids and hydraulic retention time within the biological reactor 360 may be from about 30 minutes to about 40 days, in embodiments from about 1 hour to about 20 days, in further embodiments from about 4 hours to about 10 days, in yet further embodiments from about 6 hours to about 12 hours. The recycling of the digestate is described in further detail below.

With reference to FIGS. 3A-3C, the receptacles 302 and 304 are in fluid communication therewith via first and second openings 308 and 310. The first opening 308 is controlled by a flow control mechanism 312, such as a control valve or a hydraulically actuated sluice gate, and the second opening 310 is in fluid communication with the recirculation chopper pump 314. The first opening 308 is disposed at a predetermined distance from the floor of the receptacle 304 to allow for separation of liquid and settled solid contents within the receptacle 304, thereby uncoupling solids retention time and hydraulic retention time of the biomass within the receptacle 304. The distance may be at any level designed to retain the solid contents of the biomass that settles to the floor of the receptacle 304 therein while decanting (e.g., draining) the liquid contents into the receptacle 302. Separation of liquid and solids may be accomplished by actuating the flow control mechanism 312 (e.g., lifting the sluice gate) and allowing the liquid contents of the biomass to flow into the receptacle 302 until the liquid level drops below the opening 308 or the flow control mechanism 312 is closed.

The solids and hydraulic retention time within the receptacle 302 may be from about 3 minutes to about 48 hours, in embodiments from about 2 hours to about 36 hours, in further embodiments from about 4 hours to about 24 hours. The solids retention time within the receptacle 304 may be from about 30 minutes to about 40 days, in embodiments from about 1 hour to about 20 days, in further embodiments from about 4 hours to about 10 days, in yet further embodiments from about 3 days to about 4 days, and in still further embodiments from about 6 hours to about 12 hours. The hydraulic retention time within the receptacle 304 may be from about 1 hour to about 24 hours, in embodiments, from about 2 hours to about 12 hours, in further embodiments from about 3 hours to about 8 hours. During the retention period, the temperature, pH, and ORP values within the receptacles 302 and 304 are maintained as described above.

Influent may be treated within the receptacle 302 for the duration of the retention periods described above and/or until a desired pH and/or ORP level is achieved. Treated influent may have a pH from about 3 to about 10, in embodiments from about 3.5 to about 9, in further embodiments from about 7 to about 8.5 and ORP from about −500 millivolts (mV) to about +50 mV, in embodiments about −400 mV to about 0 mV, in further embodiments from about −200 mV to about −100 mV. Biomass may be treated within the receptacle 304 for the duration of the retention periods described above and/or until a desired pH and/or ORP level is achieved. The treated biomass may have a pH from about 3 to about 7, in embodiments from about 4 to about 6 and ORP from about −250 mV to about −50 mV, in embodiments about −100 mV to about −200 mV.

Once the influent and the biomass within the receptacles 302 and 304, respectively, has been sufficiently treated the contents of the receptacles 302 and 304 are mixed. To mix the liquid and solid contents of the receptacles 302 and 304, the flow control mechanism 312 is opened and the pump 314 is activated. The pump 314 chops the solid contents of the biomass thereby reducing the particle size thereof and pushes the contents of the receptacle 304 into the receptacle 302 through the opening 310. Mechanical processing of the biomass, e.g., chopping, provides for an increased surface area of the material that may be processed by the microorganisms.

Hydrolytic microorganisms digest the biomass and the influent within the clarifier 300, which may include various proteins, fats, lignin, cellulosic species, and the like into corresponding monomers. During hydrolysis water content may be monitored and water may be added to the clarifier 300 to maintain hydrolysis. As a result of the depolymerization of the biomass by the hydrolytic microorganisms, the gases, including, but not limited to, hydrogen sulfide, hydrogen, ammonia, and combinations thereof, are generated within the clarifier 300. Acidogenic microorganisms breakdown the resulting monomers into volatile organic acids, including, but not limited to, formic, acetic, propionic, lactic, butyric, and valeric acids, and the like; alcohols, such as methanol, ethanol, propanol, and the like; and gases, such as carbon dioxide and combinations thereof are generated within the clarifier 300.

The circulation of the mixture of the biomass and the influent by the pump 314 also forces the contents of the receptacle 302 to pass through the opening 308 back into the receptacle 304. The recirculation of the contents of the receptacles 302 and 304 mixes the pasteurized influent and hydrolyzed biomass. The mixing may continue for a period of time from about 1 minute to about 12 hours, in embodiments from about 1 hour to about 8 hours, in further embodiments from about 2 hours to about 4 hours.

In embodiments, the microorganisms from the biological reactors 350 and 360 may be added to the receptacles 302 and 304 after the mixing has commenced. In further embodiments, the pH and ORP of the combined contents of the receptacles 302 and 304 may be measured by the probe 702 as the pump 314 provides samples of the combined mixture to the probe 702. The chemical feed control assembly 700 may then adjust the pH and the ORP of the mixture during the mixing process based on the measurements of the probe 702 as described above with respect to FIG. 5.

With reference to FIG. 1, once the biomass and the influent have been sufficiently mixed with the microorganisms from the biological reactors 350 and 360, the mixture is transferred to the receptacle 306. The receptacle 306 operates as an equilibration and integration point between the receptacles 302 and 304 and the downstream reactors (e.g., batch reactor 400 and digester 500). With respect to FIG. 3A and FIG. 3C, a second flow control mechanism 316, which may also be a flow control valve or a hydraulically actuated sluice gate, provides access between the receptacles 302 and 306. In embodiments, the receptacle 304 or both of the receptacles 302 and 304 may be directly coupled to the receptacle 306. The floor of the receptacle 302 may be sloped toward an opening 318 to provide for the flow of the contents from the receptacle 302. Gravitational flow of the mixture allows for additional mixing of the pasteurized influent and hydrolyzed biomass. The clarifier 300 may be configured so that the floor of the receptacle 306 is disposed at a lower level than the floor of the receptacles 302 and 304 to achieve vigorous mixing of the digestate when the digestate flows from the first biomaterial receptacle 302 to the digestate receptacle 306. It is understood that the material pumps described herein may be replaced with gravitational mechanisms for transporting or mixing digestate or biomaterials.

The solids and hydraulic retention time of the digestate within the receptacle 306 may be from about 1 hour to about 48 hours, about 3 hours to about 36 hours, in further embodiments from about 4 hours to about 24 hours and/or until a desired pH and/or ORP level is achieved. In some embodiments, the treated digestate may have a pH from about 4 to about 9. In other embodiments, the treated digestate may have a pH from about 5 to about 8. In other embodiments, the treated digestate may have a pH from about 6.5 to about 7.5. In some embodiments, the treated digestate may have an ORP from about −300 mV to about −100 mV. In other embodiments, the treated digestate may have an ORP from about −250 mV to about −150 mV.

The digestate, which is a liquid suspension of solid matter, is transferred to the batch reactor 400 for further processing. In embodiments, a portion of digestate is transferred to the batch reactor 400, while a remaining portion may be transferred to the biological reactors 350 and 360 to provide nourishment for the hydrolytic and acidogenic organisms stored therein, respectively. Amount of the digestate that may be transferred to the batch reactor 400 from the clarifier 300 may be from about 1% to about 100%, in embodiments from about 40% to about 90%, in further embodiments from about 50% to about 75%. Amount of the digestate that may be transferred to the biological reactors 350 and 360 from the clarifier 300 may be from about 0.5% to about 25%, in embodiments from about 1% to about 20%, in further embodiments from about 5% to about 15%.

As shown in FIG. 1, the biological reactor 350 is in fluid communication with the receptacle 306 via piping 353a, which is coupled to the piping 353b and 353c. Piping 353c interconnects the biological reactor 350 and the digester 500, and the piping 353b interconnects the biological reactor 350 and the receptacle 306 of the clarifier 300. The biological reactor 360 is also in fluid communication with the receptacle 306 via piping 320a, 320b, and 320c. A flow meter 322 is coupled to the portion 320b, which is adapted to measure the flow rate of the digestate therethrough. To avoid unnecessary detail, various piping runs and control valves interconnecting the components (e.g., clarifier 300, batch reactor 400, biological reactors 350 and 360, digester 500, etc.) of the system 100 are omitted. It would be readily apparent to a person of ordinary skill in the art the type and the location of the control valves that may be used to achieve desired flow control through the system 100.

The biological reactor 360 may be used as a temporary storage for the digestate prior to transferring of the digestate to subsequent treatment stages. The biological reactor 360 may also be used to increase retention time for the microorganisms to hydrolyze the digestate. In embodiments, the biological reactor 360 may also be used to determine whether the digestate has been sufficiently hydrolyzed. If it is determined that additional hydrolysis is required, the digestate may be transferred back to the clarifier 300 via piping 361 which interconnects the biological reactor 360 and the receptacle 302 as shown in FIGS. 1, 3A and 3B. The digestate may then be combined with additional hydrolyzed biomass from the receptacle 304 and moved to the receptacle 306 after mixing as described above with respect to FIGS. 3A-3C. In further embodiments, the biological reactors 350 and 360 may be interconnected via piping (not shown) to provide for addition of microorganisms directly into the biological reactor 360.

As shown in FIG. 1, the digestate from the clarifier 300 is fed to the batch reactor 400 through the piping 320a, 320b, 320d. In some embodiments, solids and inoculums from the digestate receptacle 306 of the clarifier 300 may be step fed to the batch reactor 400.

Figure 7:
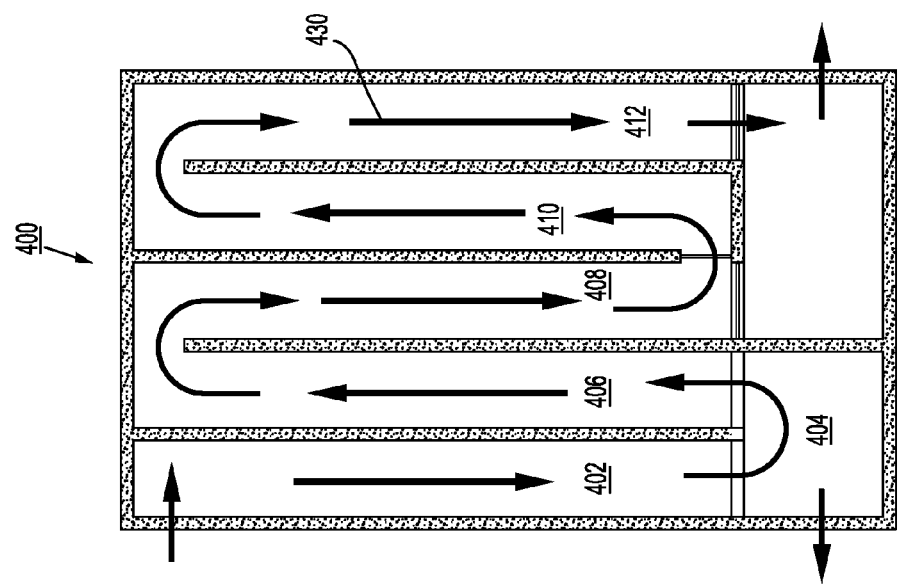
FIG. 7 is a plan, cross-sectional view of the batch reactor of FIG. 6A illustrating digestate flow according to the present disclosure.

FIGS. 6A, 6B, and 6C show plan and cross-sectional views of the batch reactor 400 taken through lines 6B-6B and 6C-6C, respectively. The batch reactor 400 may be constructed of concrete and may include a floor, walls, and a ceiling. With reference to FIG. 1, an embodiment of the batch reactor 400 is shown as a multi-chamber reactor providing a serpentine flow path for the digestate supplied thereto as represented by arrows 430 in FIG. 7. In particular, the batch reactor 400 may include a plurality of longitudinal flow chambers 402, 406, 408, 410, 412 arranged in a serpentine configuration and separated by partition walls 403, 405, 407, 411, respectively. In embodiments, the chambers 402, 406, 408, 410, 412 may be arranged in any configuration providing for fluid communication between the chambers 402, 406, 408, 410, 412. In embodiments, the chambers 402, 406, 408, 410, 412 may be arranged in a linear configuration (e.g., serially interconnecting the flow chambers 402, 406, 408, 410, 412).

The batch reactor 400 also includes drainage chambers 404, 414 for collecting settled solids and recirculating unprocessed digestate. The drainage chamber 404 is in direct fluid communication with the chambers 402, 406, such that the digestate flows from the chamber 402 through the chamber 404 and into the chamber 406. The drainage chamber 414 is in direct fluid communication with the chambers 408 and 412, which are separated by third and fourth flow control mechanisms 416 and 418, respectively. The flow chambers 408 and 410 are also separated by a flow control mechanism 420. Similarly to the first and second flow control mechanisms 312, 316, the flow control mechanisms 416, 418, 420 may also be flow control valves or hydraulically actuated sluice gates. The flow control mechanism 420 separates the chambers 402, 406, 408 into a first portion 413 and the chambers 410 and 412 into a second portion 415.

The batch reactor 400 may have a reactor volume from about 1 gallon to about 5,000,000 gallons, in embodiments, from about 1,000 gallons to about 1,000,000 gallons, in further embodiments from about 5,000 gallons to about 20,000 gallons. The first portion 413 may have a reactor volume from about 10% to about 90% of the total volume of the batch reactor 400, in embodiments from about 25% to about 75% of the total volume of the batch reactor 400. The second portion 415 may have a reactor volume from about 10% to about 90% of the total volume of the batch reactor 400, in embodiments from about 25% to about 75% of the total volume of the batch reactor 400.

The solids retention time within the first portion 413 of the batch reactor 400 may be from about 30 minutes to about 40 days, in embodiments from about 1 hour to about 20 days, in further embodiments from about 4 hours to about 10 days, in yet further embodiments from about 3 days to about 6 days, and in still further embodiments from about 6 hours to about 12 hours. The hydraulic retention time within the first portion 413 of the batch reactor 400 may be from about 1 hour to about 48 hours, in embodiments from about 2 hours to about 36 hours, in further embodiments from about 3 hours to about 8 hours.

The solids retention time within the second portion 415 of the batch reactor 400 may be from about 30 minutes to about 40 days, in embodiments from about 1 hour to about 20 days, in further embodiments from about 4 hours to about 10 days, in yet further embodiments from about 3 days to about 6 days, and in still further embodiments from about 6 hours to about 12 hours. The hydraulic retention time within the second portion 415 of the batch reactor 400 may be from about 1 hour to about 48 hours, in embodiments from about 2 hours to about 36 hours, in further embodiments from about 3 hours to about 24 hours, in yet further embodiments from about 4 hours to about 8 hours.

The floor of the chambers 402, 406, 408, 410, 412 may be sloped downward in the direction indicated by the arrows 430 to provide for gravitational flow of the digestate through the batch reactor 400. In addition, circulation of the digestate through the batch reactor 400 is also accomplished by circulation pumps 450 and 460 which are coupled via piping 452a and 462a to the drainage chambers 404 and 414, respectively. The pump 450 is also coupled to the digester 500 via piping 452b and provides processed digestate thereto. The pump 460 is coupled to the piping 462b which feeds back into the flow chamber 402 to provide for recirculation of the digestate through the batch reactor 400. The pump 460 is also coupled to the piping 462c allowing the withdrawal of solid effluent for disposal.

Figure 8:
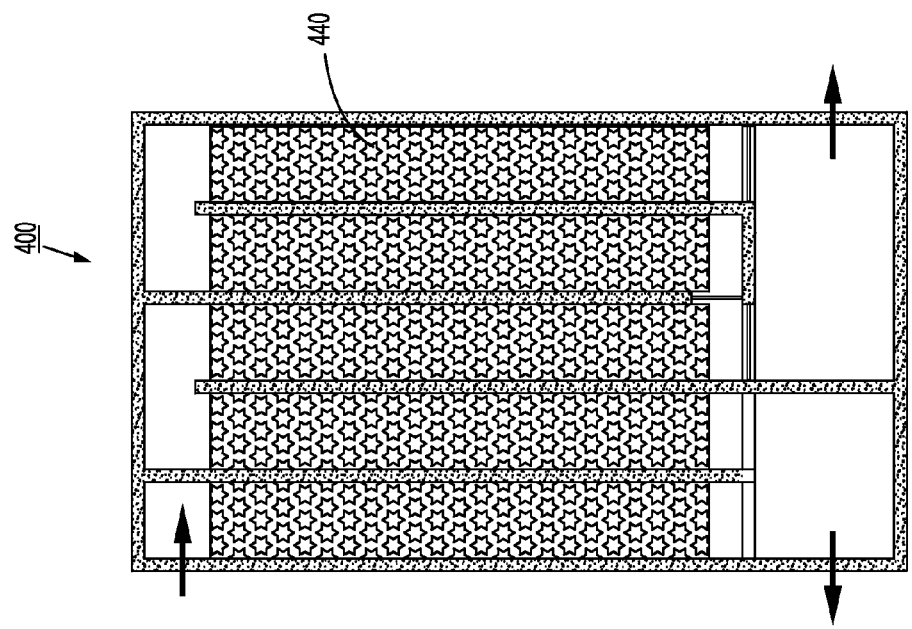
FIG. 8 is a plan, cross-sectional view of the batch reactor of FIG. 6A including digestion substrate piping according to the present disclosure.

As shown in FIG. 8, each of flow chambers 402, 406, 408, 410, 412 is filled with a digestion substrate 440 on which a consortium of suitable microorganisms are disposed. The digestion substrate 440 may be any suitable substrate including media that may be formed from any suitable material, including, but not limited to, plastics, ceramics, glass, or combinations thereof. The digestion substrate 440 may include particles of any suitable shape, including, but not limited to, toroidal, polygonal, granular, spherical, cylindrical, and combinations thereof having a diameter, cross-sectional width or height of from about 1 micron to about 30 centimeters, in embodiments from about 10 microns to about 1 centimeter. The particles may be solid, porous or combinations thereof. The digestion substrate 440 may have a surface area of from about 5 square feet (sq. ft.) per cubic foot to about 5,000 sq. ft/cu. ft., in embodiments from about 30 sq. ft/cu. ft. to about 1,000 sq. ft/cu. ft. The digestion substrate 440 may be loaded with acetogenic microorganisms. Suitable acetogenic microorganisms include, but are not limited to, *Clostridium* species, such as *C. acetobutylicum, C. perfringens, C. novyi, C. septicum, C. aciditolerans, C. frigidicarnis, C. acetireducens*, and combinations thereof. In embodiments, digestion substrate 440 may be loaded with any suitable microorganisms including but not limited to: hydrolytic, saccharolytic, proteolytic, lipolytic, nitrate reducers, nitrite reducers, iron reducers, manganese reducers, sulfate reducers, acidogenic, acetogenic, methanogenic, organic acid fermenters, alcohol fermenters, and combinations thereof.

As the digestate flows through the batch reactor 400, the digestate comes in contact with the film media 440. The acetogenic microorganisms breakdown the volatile organic acids and alcohols found in the digestate into constituent volatile organic acids, such as formic and acetic acids using the water found in the digestate. Water may be continuously supplied to the batch reactor 400 to maintain the acetogenesis. Acetogenesis also generates hydrogen and carbon dioxide gases. In embodiments, the digestion substrate 440 may be loaded with any type of microorganisms suitable for digestion of organic matter allowing the batch reactor 400 to run the entire digestion process as described in further detail below.

With reference to FIGS. 4, 6A, and 9, the batch reactor 400 also includes heat exchange piping, namely, first and second zones 604a and 604b, coupled to the heat source 600. The zones 604a and 604b may be disposed within or about the batch reactor 400 and are configured to maintain a desired temperature within the first and second portions 413 and 415 of the batch reactor 400 to provide optimum conditions for the microorganisms disposed therein.

Each of the zones 604a, 604b includes circulation loops 402a, 406a, 408a, 410a, 412a, and 402b, 406b, 408b, 410b, 412b disposed within the flow chambers 402, 406, 408, 410, 412, respectively. Each of the zones 604a, 604b may be heated to a desired temperature. In embodiments, the zone 604a may be heated to a first temperature whereas the zone 604b may be heated to a second temperature, which may be the same as or different from the first temperature. The first temperature may be suitable for mesophilic microorganisms and may be from about 25° C. to about 40° C., in embodiments from about 35° C. to about 38° C. The second temperature may be suitable for thermophilic microorganisms and may be from about 45° C. to about 100° C., in embodiments from about 50° C. to about 60° C.

Each of the circulation loops 402a, 406a, 408a, 410a, 412a, and 402b, 406b, 408b, 410b, 412b may be selectively isolated via isolation valves (not shown) to maintain each of the flow chambers 402, 406, 408, 410, 412 at a desired temperature. In embodiments, circulation loops 402a, 406a, 408a of the first zone 604a and 410b, 412b of the second zone 604b may be activated such that the flow chambers 402, 406, 408 are heated to the first temperature and the flow chambers 410 and 412 are heated to the second temperature. This configuration tailors the temperature to each of the flow chambers 402, 406, 408, 410, 412 to provide optimum conditions for the microorganisms disposed therein.

The digestate from the clarifier 300 enters the batch reactor 400 into the flow chamber 402. As the digestate is pumped through the piping 320d, the pH and ORP of the digestate is sampled by the probe 704, which is coupled thereto as shown in FIG. 5. The pH and ORP of the digestate within the first portion 413 of the batch reactor 400, which includes the chambers 402, 406, 408, is adjusted by the chemical feed control assembly 700. The pH may be adjusted to a value of from about 3 to about 10, in embodiments from about 5 to about 9, in further embodiments from about 6 to about 6.5 and the ORP may be adjusted to a value of from about −500 mV to about +50 mV, in embodiments from about −400 mV to about 0 mV, in further embodiments from about −250 mV to about −150 mV. The logic controller 802 signals the pump 722b to release a desired amount of chemicals from the tank 722a at a desired rate based on the measured pH and ORP values.

The chemical feed control assembly 700 also measures the pH and ORP of the digestate as it passes through the chambers 410 and 412 using the probe 706. The pH and ORP of the digestate within a second portion 415 of batch reactor 400, which includes the chambers 410 and 412, is also adjusted by the chemical feed control assembly 700. The pH may be adjusted to a value of from about 3 to about 10, in embodiments from about 5 to about 9, in further embodiments from about 6.5 to about 7 and the ORP may be adjusted to a value of from about −500 mV to about +50 mV, in embodiments from about −400 mV to about 0 mV, in further embodiments from about −250 mV to about −150 mV. The logic controller 802 signals the pumps 724b and 726b to release a desired amount of chemicals from the tanks 724a and 726a, respectively, at a desired rate based on the measured pH and ORP values.

In embodiments, the chemicals stored within the tank 722a that are fed into the flow chambers 402, 406, 408 may be different from the chemicals stored within the tanks 724a and 726a that are fed into the flow chambers 410 and 412 to tailor the pH and ORP within these chambers 402, 406, 408, 410, 412. This configuration in combination with the first and second zones 604a, 604b allows the system 100 to tailor the temperature as well as pH and ORP within the flow chambers 402, 406, 408, 410, 412 to obtain suitable growth conditions for various microorganisms.

A chelating agent may be added to the digestate to remove or coagulate metals found therein. Influent collected from the livestock and farm animals may contain undesirable levels of metals typically found in the feed. Metals may include, but are not limited to, iron, lead, aluminum, silver, nickel, and ions, micro and nanoparticles, molecules, and combinations thereof. In embodiments, suitable chelating agents include, for example, aluminum sulfate, hydrated potassium aluminum sulfate (alum), organic acids such as ethylene diamine tetra acetic acid (EDTA), GLDA (commercially available L-glutamic acid N,N diacetic acid), humic and fulvic acids, peta-acetic and tetra-acetic acids; salts of organic acids including salts of methylglycine diacetic acid (MGDA), and salts of ethylenediamine disuccinic acid (EDDS); esters of organic acids including sodium gluconate, magnesium gluconate, potassium gluconate, potassium and sodium citrate, nitrotriacetate (NTA) salt; substituted pyranones including maltol and ethyl-maltol; water soluble polymers including polyelectrolytes that contain both carboxylic acid (COOH) and hydroxyl (OH) functionalities; and combinations thereof. In embodiments, EDTA, a salt of methylglycine diacetic acid (MGDA), or a salt of ethylenediamine disuccinic acid (EDDS), may be utilized as a chelating agent. The chelating agent may be added in an amount from about 0.001% to about 1% by weight of the digestate, in embodiments from about 0.01% to about 0.05%, in further embodiments from about 0.015% to about 0.02%. The chelating agent complexes or chelates with the coagulant metals, thereby extracting the metals from the digestate.

The resulting metal complexes settle to the bottom of the batch reactor 400, namely, the drainage chamber 404, from where the complexes are removed by the pump 450 into the digester 500 where they settle to the bottom thereof. The floor of the drainage chamber 404 is at a lower level than the floor of the flow chambers 402 and 406, allowing the heavier metal complex particles to sink to the bottom for subsequent removal.

The flow of the digestate through the batch reactor 400 may also be controlled by actuating the flow control mechanisms 416, 418, 420 in any desired sequence and/or for any desired duration. In embodiments, the flow control mechanisms 416 and 418 may remain closed to increase digestate dwell time within the batch reactor 400. During that time, the flow control mechanism 420 may be closed to ensure that the digestate stays only within the first portion 413 (e.g., mesophilic reactor maintained at the first temperature). The digestate may be treated within the first portion 413 for a period of time from about 30 minutes to about 40 days, in embodiments from about 4 hours to about 10 days and/or until a desired pH and/or ORP level is achieved. Treated digestate may have a pH from about 3 to about 10, in embodiments from about 5 to about 9, in further embodiments from about 6 to about 7 and an ORP from about −500 mV to about +50 mV, in embodiments about −400 mV to about 0 mV, in further embodiments from about −150 mV to about −250 mV.

As described above, the pH, ORP and temperature may be individually controlled for each specific chamber 402, 406, 408, 410, 412. Controlling the flow of the digestate via flow control mechanisms 416, 418, 420 allows for control of the length of time that the digestate is exposed to the varying conditions within the batch reactor 400. In further embodiments, the flow control mechanism 420 may be opened to allow the digestate to flow into the second portion 415 (e.g., thermophilic reactor maintained at the second temperature). The chambers 410 and 412 may be at a different pH, ORP and temperature than the first portion 413. The flow control mechanisms 416 and 418 may be opened to allow the digestate to be recirculated by the pump 460 through the piping 462b. The digestate may be treated within the second portion 415 for a period of time from about 30 minutes to about 40 days, in embodiments from about 4 hours to about 10 days and/or until a desired pH and/or ORP level is achieved. Treated digestate may have a pH from about 3 to about 10, in embodiments from about 5 to about 9, in further embodiments from about 6 to about 7 and ORP from about −500 mV to about +50 mV, in embodiments about −400 mV to about 0 mV, in further embodiments from about −150 mV to about −250 mV.

The digestate may be continuously pumped off via the pump 450 from the drainage chamber 404 into the digester 500 for further processing. In embodiments, the pumps 450 and 460 may be operated in tandem to provide for continual recirculation and removal of the digestate or in sequence, to ensure that removal of the digestate occurs only after the digestate has undergone acetogenesis to a desired degree.

In some embodiments, the batch reactor 400 may be a stand-alone digestion system that receives digestate from a digestate source other than the clarifier 300 and continuously recirculates the digestate until the digestion process is complete. When a digestion cycle is complete, all or a portion of the processed digestate may be wasted as effluent. The digestate source may include a storage receptacle containing digestate or a mixing receptacle in which digestate solids are mixed with a liquid.

Figure 11:
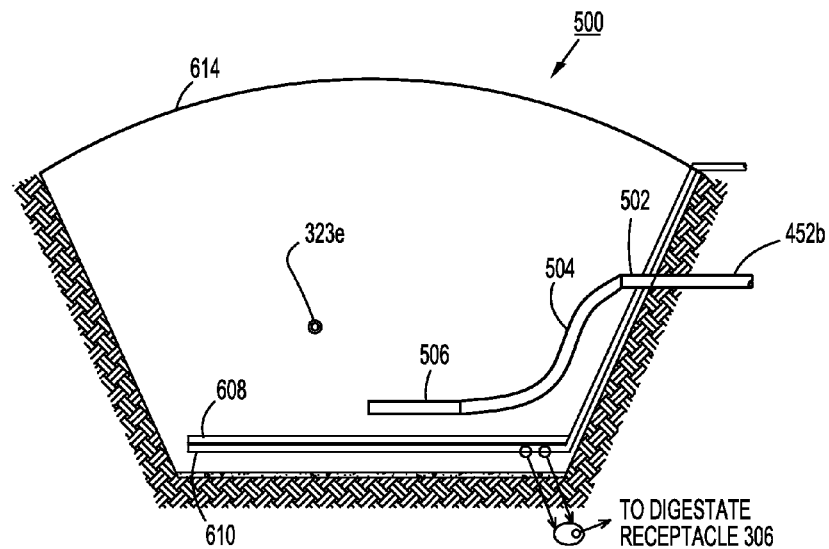
FIG. 11 is a side, cross-sectional view of the digester of FIG. 10.
Figure 12:
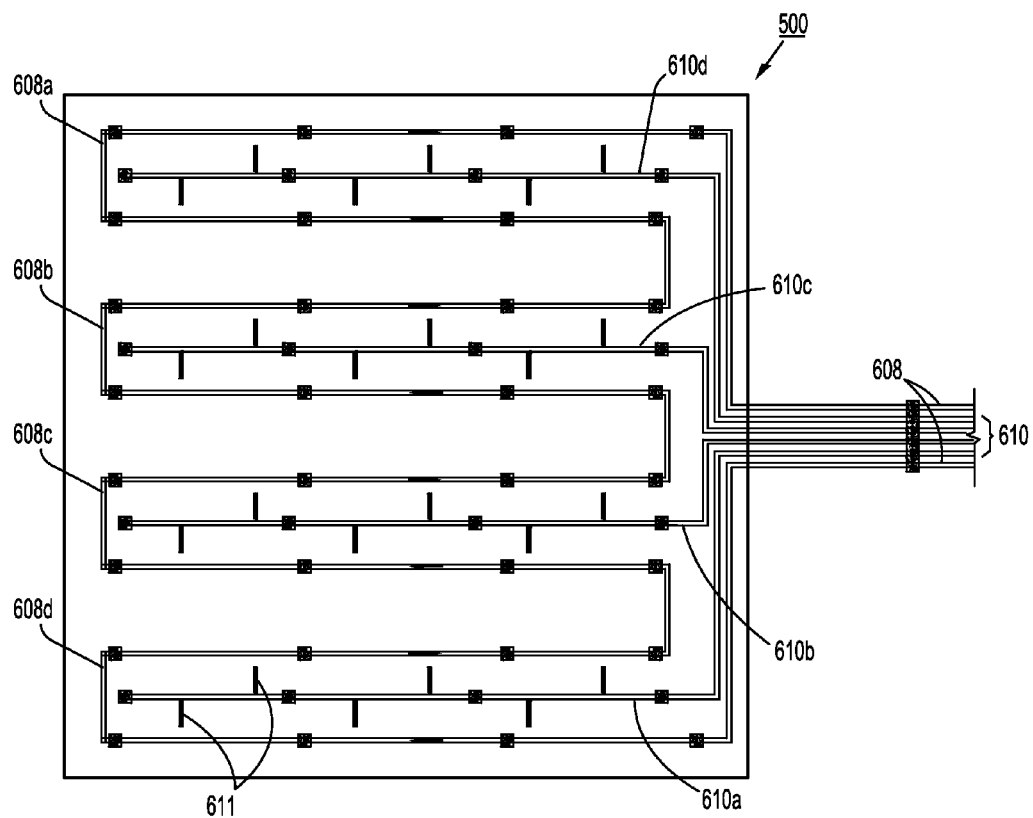
FIG. 12 is a plan, cross-sectional view of the digester of FIG. 10 including heat exchange piping according to the present disclosure.

As shown in FIGS. 10, 11, and 12, the digester 500 may be a leach bed reactor configured to operate as a modified mix, settle, and decant system. The digester 500 may have a reactor volume from about 1 gallon to about 5,000,000 gallons, in embodiments, from about 1,000 gallons to about 4,000,000 gallons, in further embodiments from about 500,000 gallons to about 1,000,000 gallons. The digester 500 may be constructed as an in-ground pit with concrete floor and walls or any other suitable material. The surface of the digester 500 may be lined with any suitable material, including, but not limited to, high-density polyethylene, glass, polytetrafluoroethylene, and the like. The hydraulic retention time within the digester 500 may be from about 1 day to about 60 days, in embodiments from about 10 days to about 50 days, in further embodiments from about 20 days to about 30 days. The solid retention time within the digester 500 may be from about 1 day to about 90 days, in embodiments from about 20 days to about 90 days, in further embodiments from about 30 days to about 40 days.

The piping 452b from the batch reactor 400 is connected to a flexible inlet 502 as shown in FIGS. 10 and 11. The inlet 502 includes a flexible portion 504 coupled to the piping 452b at one end and to a rigid outlet portion 506 at the other end. In embodiments, the rigid portion 506 may be Y-shaped with respect to the flexible portion 504 having a first segment 506a and a second segment 506b. The angle between the first and second segments 506a and 506b, a, may be less than the angle between each of the first and second segments 506a and 506b and the flexible portion 504, b and c, respectively. The first and second segments 506a and 506b may be of same or different lengths as shown in FIG. 10. The angular configuration and the Y-shape of the portion 506 project the digestate stream in two different directions. The streaming generates vortices, which mix the contents of the digester 500. The flexible portion 504 may be formed from any suitable material that would allow the inlet 502 to float up along with the contents of the digester 500 at least partially on the surface thereof as it is continuously filled. Suitable materials include, but are not limited to, semi-crystalline thermoplastics, amorphous thermoplastics, and combinations thereof. The digestate within the digester 500 may have a ratio of liquid to solid contents from about 0.1% to about 25%, in embodiments from about 5% to about 20%, in further embodiments from about 10% to about 15%.

With respect to FIGS. 4, 11 and 12, the digester 500 also includes heat exchange piping 608 disposed within, in embodiments at the bottom of the digester 500 as shown in FIG. 11 or about the digester 500. The heat exchange piping 608 is configured to maintain the temperature within the digester 500 to provide optimum conditions for the microorganisms disposed therein from about 25° C. to about 60° C., in embodiments from about 30° C. to about 40° C., in further embodiments from about 35° C. to about 38° C. The heat exchange piping 608 may include one or more circulation loops 608a, 608b, 608c, 608d, which may be disposed in a serpentine fashion throughout the digester 500 to maximize the surface area of the heat exchange piping 608.

The digester 500 includes methanogenic microorganisms. Suitable methanogenic microorganisms include, but are not limited to, *Methanothermobacter* species, *Methanobacterium oinelianskii*, *Mb. formicium*, *Mb. sohngenii*, *Methanosarcina barkeri*, *Ms. Methanica*, *Mc. mazei*, *Methanobacteriaceae*, *Methanosarcinaceae*, *Methanosaetaceae*, *Methanocorpusculaceae*, *Methanomicrobiaceae*, and combinations thereof. The methanogenic microorganisms breakdown the volatile organic acids and alcohols found in the digestate into methane, hydrogen, and carbon dioxide gases. In addition, various gases, including, but not limited to, carbon dioxide and hydrogen, are reacted to form methane and water.

The digester 500 is also coupled via the piping 353d to a digester pump station 550 having a pump 555, which is configured to remove and/or recirculate the digestate contained within the digester 500. The digester pump station 550 is coupled to the piping 353c which is connected to the biological reactor 350 via the piping 353a and the receptacle 306 via the piping 353b. The digester pump station 550 removes the digestate from the digester 500 and recirculates it through the biological reactor 350 and/or the receptacle 306. The pump 322 supplies the digestate back to the digester 500 through the piping 323e. Recirculated digestate from the digester 500 may be further processed and/or mixed with unprocessed biomass and influent within the clarifier 300 and processed within the batch reactor 400 as described above prior to being added back into the digester 500.

Figure 13:
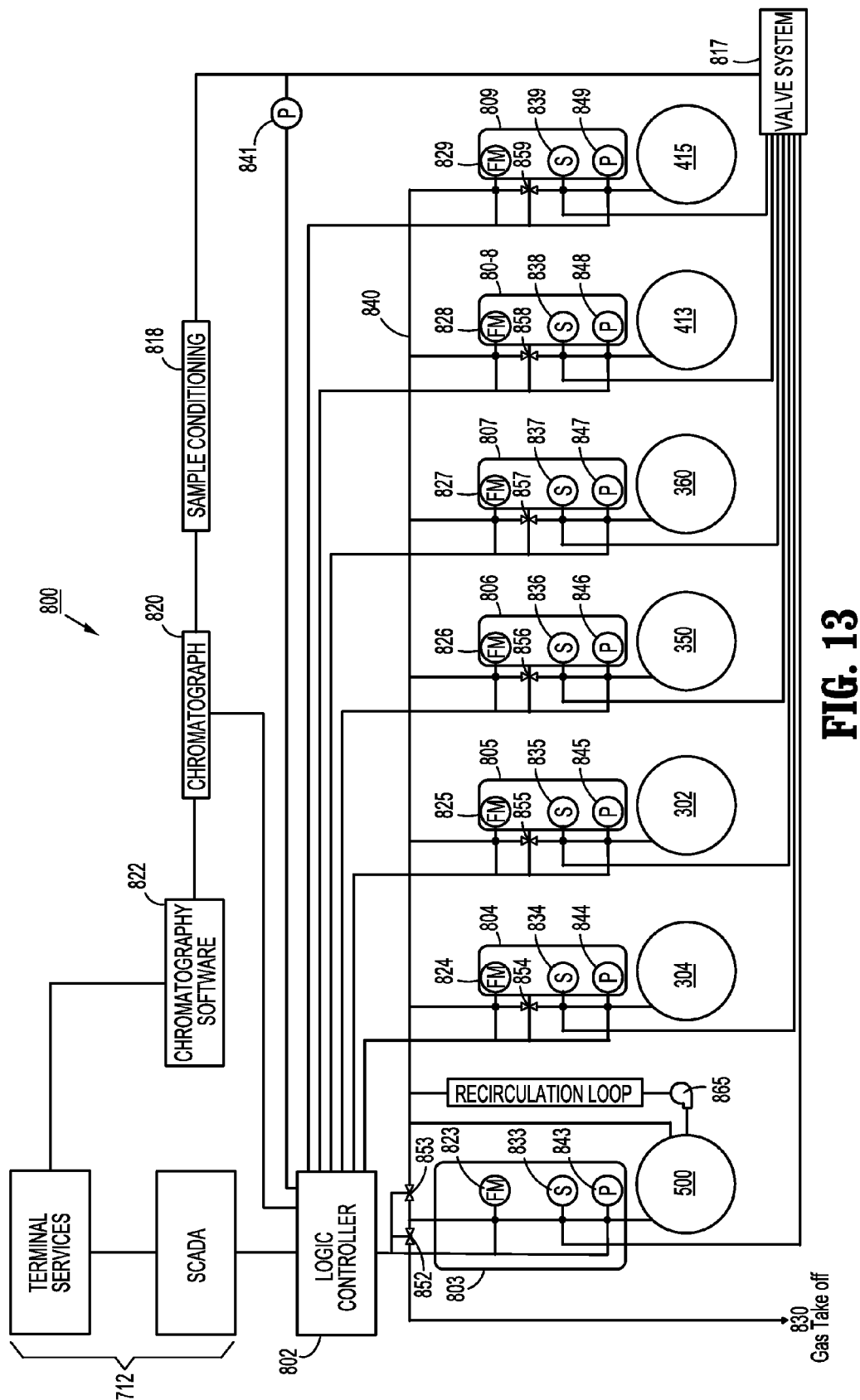
FIG. 13 is a schematic diagram of a gas and mass flow control system according to the present disclosure.
Figure 14:
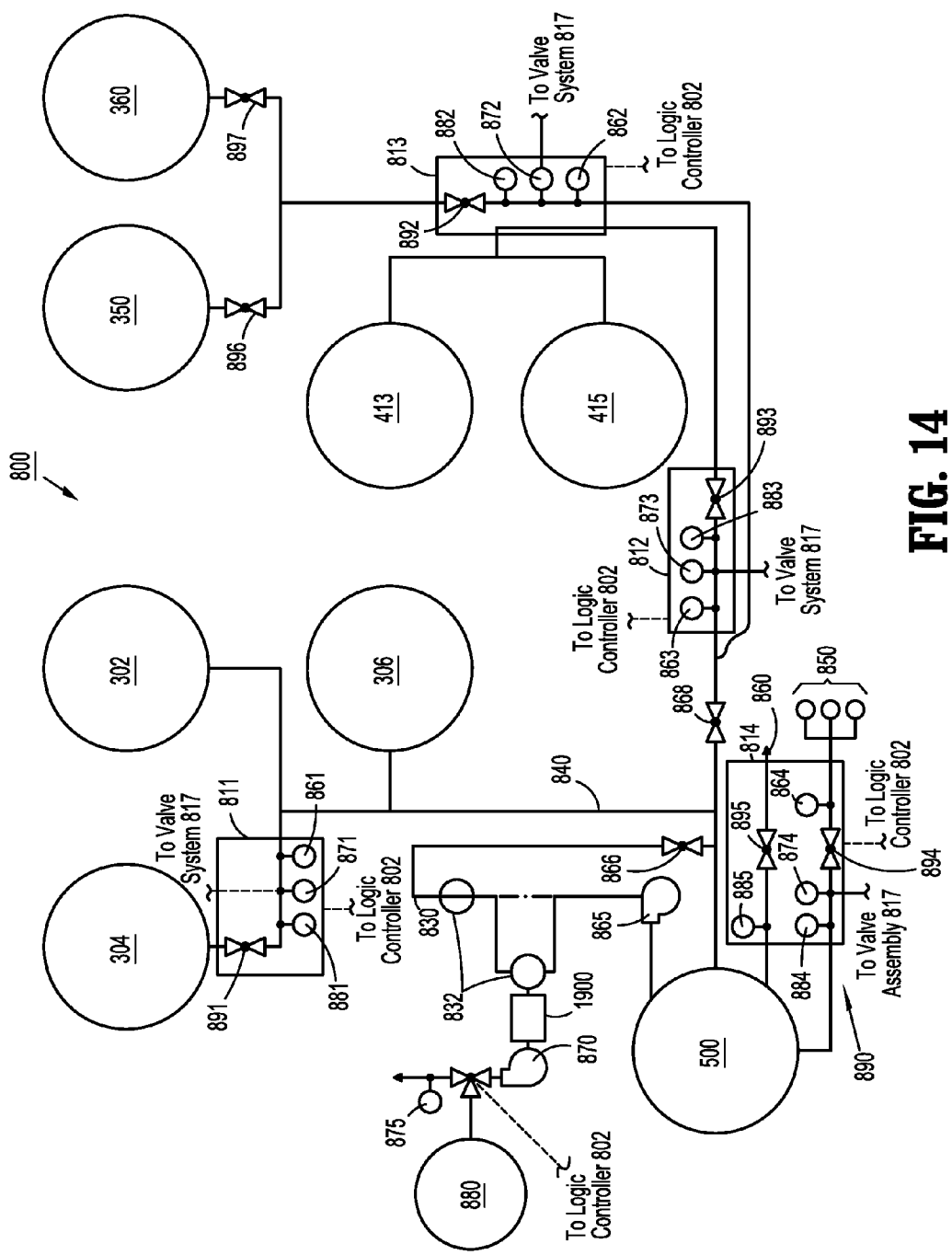
FIG. 14 is a schematic diagram of a regenerative gas and vacuum control system according to the present disclosure.

With respect to FIGS. 13 and 14, the system 100 also includes a gas and mass flow control assembly 800. The flow control assembly 800 is configured to sample gases generated within the clarifier 300, the biological reactors 350 and 360, the batch reactor 400, and the digester 500. The gas and mass flow control assembly 800 is also configured to provide the measurements to a logic controller 802, which then outputs the data to a user and/or automatically controls the flow of the digestate and/or gases through the system 100. The logic controller 812 may also be coupled to the computerized control interface 712, which is described above with respect to FIG. 5. The logic controller 802 may be any suitable logical processing unit embodied as hardware, including but limited to, a processor, a field programmable gate array, and the like or software, such as a virtual processing environment.

FIG. 13 illustrates a gas and mass flow control assembly 800 that controls flow of gases from the digester 500, the clarifiers, and the reactors to the digester 500 or the gas take off 830. As shown in FIG. 13, the logic controller 802 is coupled to a plurality of flow meters 823-829, a plurality of pressure sensors 843-849, and a plurality of gas flow control valves 853-859, which are in fluid communication with the digester 500, the receptacles 304 and 302 of the clarifier 300, the biological reactors 350 and 360, and the first and second portions 413 and 415 of the batch reactor 400, respectively. In some embodiments, the plurality of pressure sensors 843-849 may be replaced with a single pressure sensor 841 that is fluidly coupled to the output of the valve assembly 817. In this configuration, the logic controller 802 operates the valve system 817 to selectively couple each of the sample ports 833-839 to the pressure sensor 841 so that the pressure sensor 841 can measure the pressure within the digester 500, the receptacles 304 and 302 of the clarifier 300, the biological reactors 350 and 360, and the first and second portions 413 and 415 of the batch reactor 400.

The gas and mass flow control assembly 800 also includes a gas flow control valve 852 that is fluidly coupled between the gas take off 830 and the digester 500, the receptacles 304 and 302 of the clarifier 300, the biological reactors 350 and 360, and the first and second portions 413 and 415 of the batch reactor 400. The logic controller 802 controls the actuation of the gas flow control valves 852-859 based on the data generated by the gas flow meters 823-829 and the pressure sensors 843-849. In this configuration, the logic controller 802 controls the flow of gases between any of the receptacles 304, 302 of the clarifier 300 or reactors 350, 360, 400 and the digester 500 or the gas take off 830.

The digester 500, the receptacles 304 and 302 of the clarifier 300, the biological reactors 350 and 360, and the first and second portions 413 and 415 of the batch reactor 400 are also in fluid communication with gas sample ports 833-839, respectively. The gas sample ports 833-839 are configured to provide a desired amount of gas to the gas analyzer 820. The gas pressure sensors 843-849 provide continual gas pressure readings within the digester 500, the receptacles 304 and 302 of the clarifier 300, the biological reactors 350 and 360, and the first and second portions 413 and 415 of the batch reactor 400.

Each of the sample ports 833-839 is fluidly coupled to a valve system 817, which controls the flow of gas samples to a sample conditioner 818. The valve system 817 is configured to allow only a single gas sample to pass to the sample conditioner 818 to prevent mixing of the gas samples. The sample conditioner 818 prepares the gas samples prior to passing the gas samples to a gas analyzer (e.g., a chromatograph 820), which analyzes the gas samples and provides the concentration of constituent gases of each of the gas samples to the logic controller 802. The chromatograph 820 is also coupled to the control interface 712 via chromatography software 822 that may output gas analysis results to the user.

The gas pressure and concentration values as determined by the mass flow control assembly 800 may be used in conjunction with the pH and ORP values as determined by the chemical control assembly 700 to determine when the digestate may be transported between the clarifier 300, the batch reactor 400, the biological reactors 350 and 360, and the digester 500. The chemical and flow controllers 700 and 800 may be coupled directly to any of the flow control mechanisms, valves, pumps, fans, and other components described in the present disclosure to allow for remote operation thereof. In embodiments, the pH, ORP, gas pressure, and concentration may be outputted via control interface 712 allowing for manual control over the system 100. In further embodiments, the system 100 may be automated, such that the chemical and flow control assembly 700 and 800 automatically operate the components of the system 100 to provide for automatic transport of the digestate between the clarifier 300, the batch reactor 400, the biological reactors 350 and 360, and the digester 500.

The logic controller 802 also controls the flow of gaseous byproducts from the digestion processes between the clarifier 300, the batch reactor 400, the biological reactors 350 and 360, and the digester 500. This is accomplished by actuating the valves 853-859. The logic controller 802 may operate the valves of each of the gas samplers 804-816 at regular intervals, based on automatic commands from the logic controller 802, user requests via the control interface 712, and combinations thereof. In embodiments, the valves 853-859 may be controlled using PID control loops 803-809, respectively, based on a desired sampling rate, gas pressure measured by the pressure sensors 843-849, gas concentrations determined by the chromatograph 820 and chromatography software 822, gas pressure setpoint values, and gas concentration setpoint values.

The valves 852-859 are opened to collect gaseous byproducts generated during digestion within the clarifier 300, the biological reactors 350 and 360, the batch reactor 400, and the digester 500. The gas flow meters 823-829 provide the gas flow measurements to the logic controller 802 allowing for the determination of when a desired amount of gas has been withdrawn. The withdrawn gas may be either transported to the clarifier 300, the batch reactor 400, the biological reactors 350 and 360, the digester 500, or gas take-off 830 as described in further detail below.

The logic controller 802 may actuate the valves 852-859 concurrently to allow for the flow of the gases between the receptacles 302 and 304 of the clarifier 300, the biological reactors 350 and 360, and the first and second portions 413 and 415 of the batch reactor 400, and the digester 500. As shown in FIG. 14, the logic controller 802 is also coupled to a second plurality of gas sample ports 871-874.

FIG. 14 illustrates a regenerative gas and vacuum control system that may be used together with the gas and mass flow control assembly of FIG. 13. The valve system 817 is in fluid communication with the sample ports 833-839 of the digester, clarifiers, and batch reactors. The valve system 817 is configured to selectively withdraw a desired amount of gas from the sample ports 871-874 of the digester 500, clarifier 300, and reactors 350, 360, 400 and provide the sampled gas to the gas analyzer 820 (e.g., a chromatograph). The gas sample ports 871-874 are used in substantially the same manner as the gas sample ports 833-839 of FIG. 13, namely, the gas sample ports 871-874 provide gas samples to the gas analyzer 820. The logic controller 802 operates the gas flow control valves 891-894 based on the gas pressure measured by the pressure sensors 881-884, the gas flow measured by the gas flow meters 861-864, and the concentration values determined by the gas analyzer 820. The PID control loops 811-814 monitor and control gas flow through gas piping 840, which interconnects the clarifier 300, the biological reactors 350 and 360, the batch reactor 400, and the digester 500.

Transportation of gases between the clarifier 300, the biological reactors 350 and 360, the batch reactor 400, and the digester 500 allows for removing gases that are generated in one portion of the system 100 to another portion of the system 100 where such gases are used as reactants. In embodiments, the clarifier 300 and the batch reactor 400 generate hydrogen gas during hydrolysis, acidogenesis, and acetogenesis reactions that occur therein and the hydrogen gas is used during methanogenesis process within the digester 500 as described above. Thus, supplying the hydrogen gas to the digester 500 from the clarifier 300 and the batch reactor 400 provides for more efficient utilization of the reaction byproducts.

With reference to FIGS. 11, 12, and 14, a gas diffuser 610 is disposed at the bottom of the digester 500. The gas diffuser 610 is coupled to the gas piping 840 and includes a plurality of branches 610a, 610b, 610c, 610d. The gas diffuser 610 also includes a plurality of gas diffusers 611 coupled to the branches 610a, 610b, 610c, 610d. The gas diffusers 611 may be constructed as a longitudinal, substantially cylindrical pipe termination with a plurality of openings of varying or similar diameter. The gas collected by the flow control assembly 800 is passed through the piping 840 and into the gas diffuser 610 from which the gas is bubbled through the contents of the digester 500. The diffused gas agitates the digestate of the digester 500 as it is diffused therethrough. As described above, the gas is also used in the methanogenesis occurring within the digester 500. Any remaining gas exits the digestate and is collected by a stretchable cover 514 disposed over the digester 500 as shown in FIG. 11.

The cover 514 may be formed from any elastic material that may be inflated under the pressure from the gases generated by the digester 500. The gases may be withdrawn from the volume enclosed by the cover 514 to the gas take-off 830, a flare burners 850, an emergency vent 860, and combinations thereof. The flare burners 850 and the emergency vent 860 are coupled to the pressure sensors 884 and 885, respectively, which provide gas pressure measurements to the logic controller 802. The logic controller 802 uses these gas pressure measurements to control gas flow from the digester 500 to the emergency evacuation vent 860 and/or the flare burners 850. The flare burners 850 and the emergency vent 860 are used to relieve the gas pressure within the digester 500 if an insufficient amount of gas is being removed by the gas take-off 830.

The gas take-off 830 is coupled to the piping 840 and removes the gas from the clarifier 300, the biological reactors 350 and 360, the batch reactor 400, and the digester 500 for processing, for transport, or for further use at the heat source 600 or other heat and/or power generators. The gas take-off 830 is coupled to one or more scrubbers 832 that remove undesirable gases, including, but not limited to, hydrogen sulfide, ammonia, carbon dioxide, and combinations thereof, prior to transporting purified methane to the heat source 600. The heat source 600 utilizes the methane extracted from the system 100 to maintain the temperature within the clarifier 300, the biological reactors 350 and 360, the batch reactor 400, and the digester 500 as described above. Additional methane may be utilized by other types of generators to generate electricity and the like.

Figure 15A:
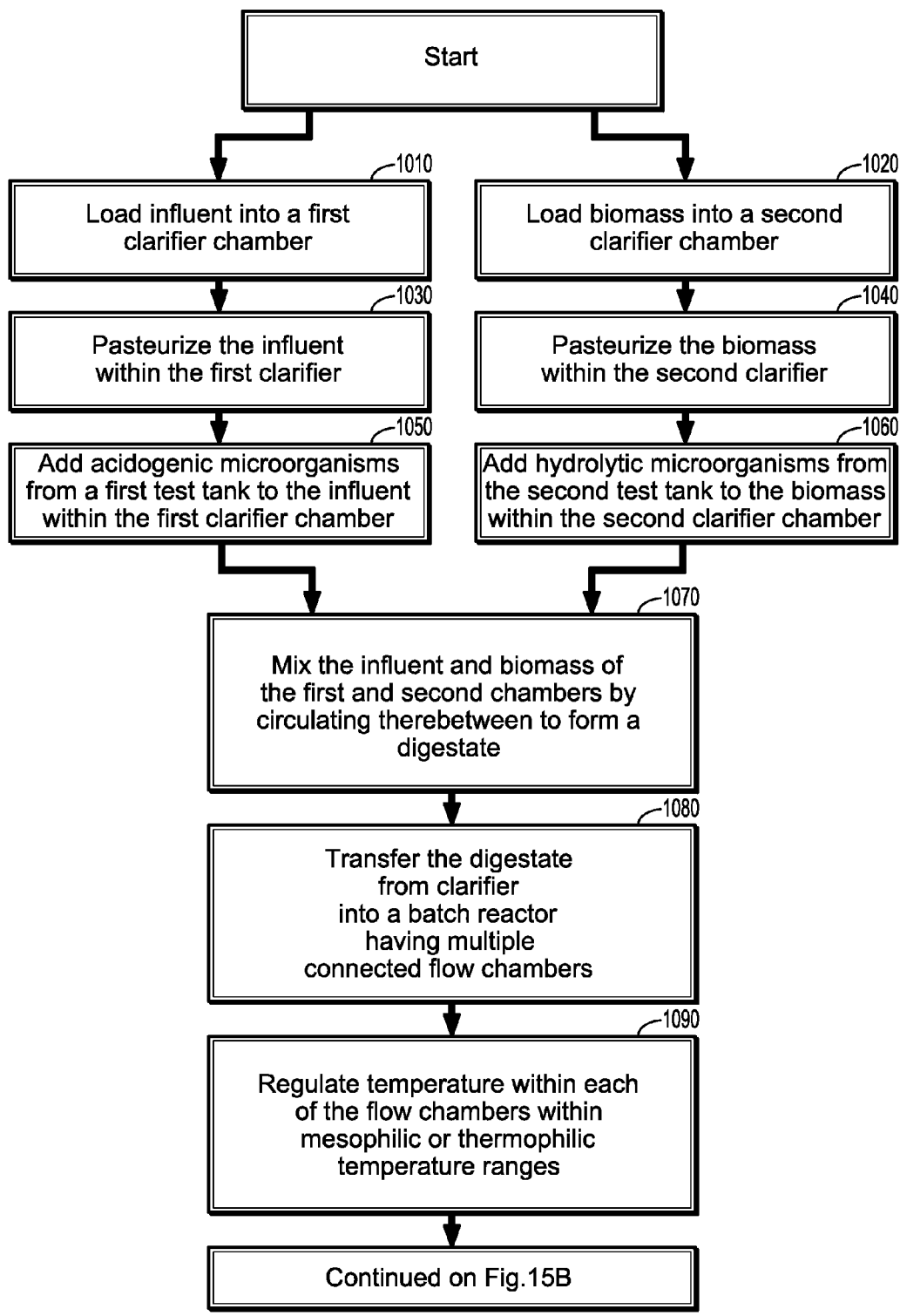
FIGS. 15A and 15B illustrate a flow chart of a method according to the present disclosure.
Figure 15B:
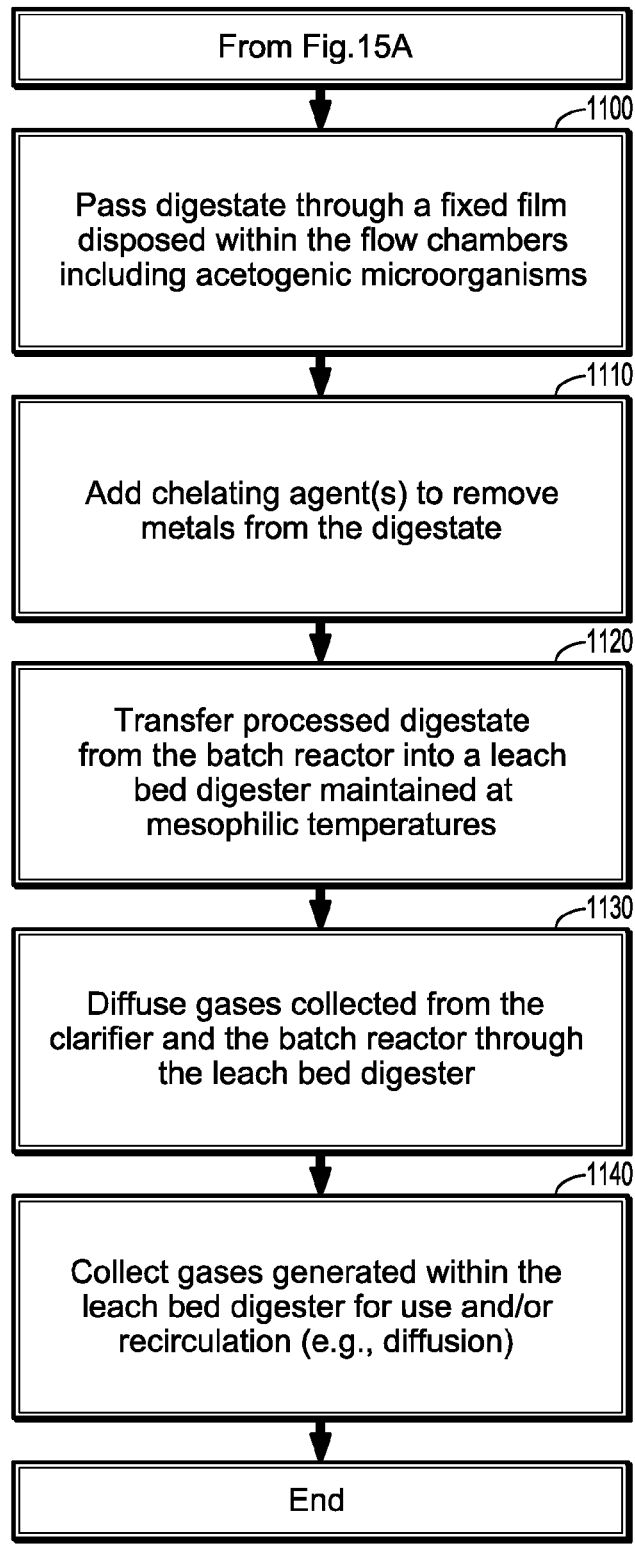

FIGS. 15A and 15B illustrate a method of the present disclosure. The method includes loading the influent and the biomass into the receptacles 302 and 304 of the clarifier in steps 1010 and 1020, respectively. The influent and the biomass are then pasteurized in steps 1030 and 1040. After pasteurization and balancing pH and ORP values within the clarifier 300, acidogenic and hydrolytic microorganisms are added to the clarifier 300 from the biological reactors 350 and 360 in steps 1050 and 1060, respectively. In step 1070, the contents of the receptacles 302 and 304, namely, the influent and the biomass, are mixed to form a digestate and are transferred to the receptacle 306. In step 1080, the digestate from the clarifier 300 is transferred to the batch reactor 400. In step 1090, the temperature within each of the first and second portions 413 and 415 of the batch reactor 400 is regulated to a desired level. In step 1100, the digestate is passed through the digestion substrate 440 disposed within multiple flow chambers 402, 406, 408, 410, 412 of the batch reactor 400. In step 1110, a chelating agent may be added to remove metals from the digestate before further processing. After passing through the batch reactor 400, the digestate is transferred to the digester 500 in step 1120. In step 1130, gases are collected from the clarifier 300, the biological reactors 350 and 360, the batch reactor 400, and the digester 500 and are diffused through the digester 500 allowing for agitation of the contents of the digester 500 and further processing of the gases. In step 1140, the gases from the digester 500 are collected and are used in powering the heat source 600 or other generators and/or recirculated through the digester 500.

Figure 16:
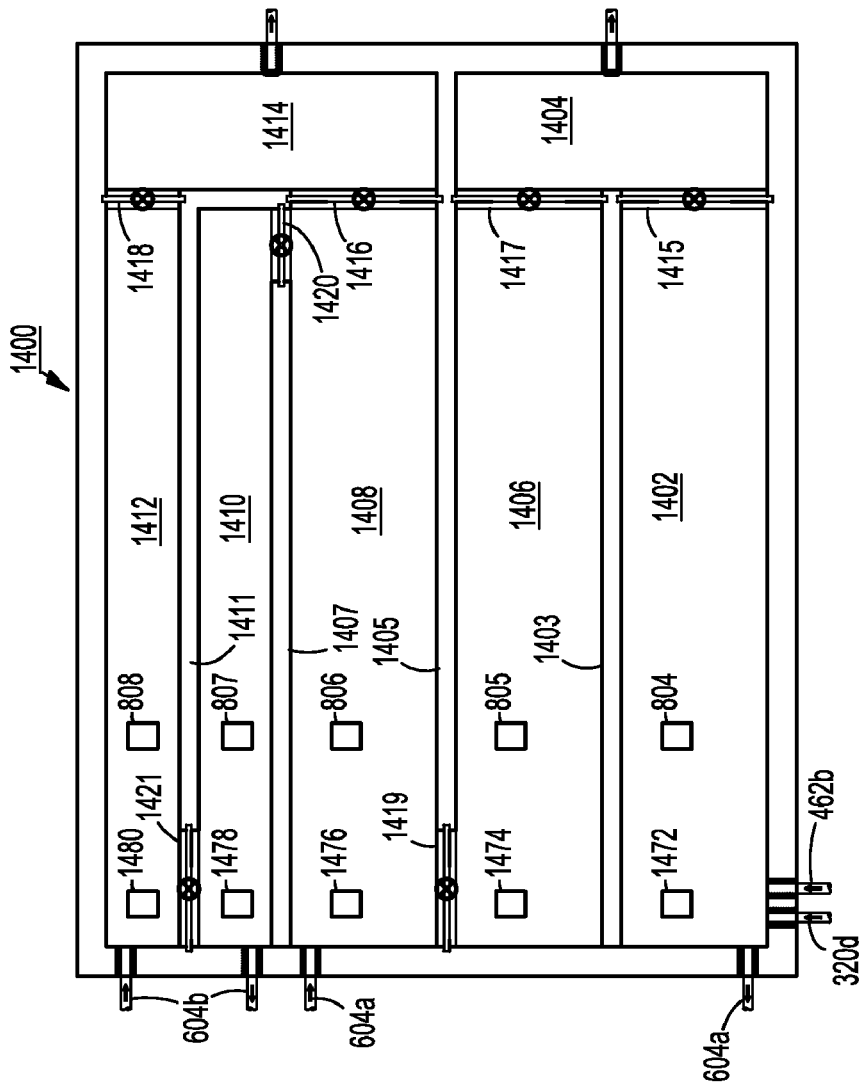
FIG. 16 is a plan, cross-sectional view of a batch reactor according to the present disclosure.

With respect to FIG. 16, another embodiment of a batch reactor 1400 is shown. The reactor 1400 is similar to the batch reactor 400 of FIGS. 6A-9. As shown in FIG. 16, the reactor 1400 also may be a multi-chamber reactor providing a serpentine flow path for the digestate supplied thereto similarly to the batch reactor 400 as represented by arrows 430 in FIG. 7. In particular, the reactor 1400 includes a plurality of longitudinal flow chambers 1402, 1406, 1408, 1410, 1412 arranged in a serpentine configuration and separated by partition walls 1413, 1415, 1407, 1411, respectively. In embodiments, the chambers 1402, 1406, 1408, 1410, 1412 may be arranged in any configuration providing for fluid communication therebetween (e.g., serially interconnecting the flow chambers 1402, 1406, 1408, 1410, 1412).

The reactor 1400 may include drainage chambers 1404 and 1414 for collecting settled solids and recirculating unprocessed digestate. The drainage tank 1404 is in direct fluid communication with the chambers 1402 and 1406, such that the digestate flows form the tank 1402 through the tank 1404 and into the tank 1406. The chambers 1402 and 1406 are separated from the chamber 1404 by flow control mechanisms 1415 and 1417, respectively. The flow chambers 1406 and 1408 are separated by a flow control mechanism 1419. The drainage tank 1414 is in direct fluid communication with the chambers 1408 and 1412, which are separated by flow control mechanisms 1416 and 1418, respectively. The flow chambers 1408, 1410, 1412 are also separated by flow control mechanisms 1420 and 1421, respectively. Similarly to the first and second flow control mechanisms 312 and 316, the flow control mechanisms 1415, 1417, 1416, 1418, 1419, 1420, 1421 may also be flow control valves or hydraulically actuated sluice gates.

Although the present disclosure described various stages of anaerobic digestion taking place within various components of the system 100, namely, the clarifier 300, the batch reactor 400, and the digester 500, in embodiments, the reactor 1400 may be configured to carry out multiple digestion processes therein. In particular, the reactor 1400 may include multiple microorganisms within one or more of the flow chambers 1402, 1406, 1408, 1410, 1412, each of which is equipped with the flow control mechanisms 1415, 1417, 1416, 1418, 1419, 1420, 1421 and circulation loops 402a, 406a, 408a, 410a, 412a, and 402b, 406b, 408b, 410b, 412b allowing for regulation of temperature.

In embodiments, pH and ORP conditions within each chamber 1402, 1406, 1408, 1410, 1412 may also be regulated. With respect to FIG. 16, a plurality of pH and ORP probes 1472, 1474, 1476, 1478, 1480 are disposed within each of the flow chambers 1402, 1406, 1408, 1410, 1412. The pH and ORP probes 1472, 1474, 1476, 1478, 1480 are substantially similar to the probes 702, 704, 706 described above with respect to FIG. 5 and are coupled to the logic controller 802 and the chemical supply tanks 720a, 722a, 724a, 726a. The probes 1472, 1474, 1476, 1478, 1480 measure the pH and ORP within the chambers 1402, 1406, 1408, 1410, 1412 and the logic controller 802 adjusts the pH and ORP within each of the chambers 1402, 1406, 1408, 1410, 1412 to a desired level as described above.

Any number of the chambers 1402, 1406, 1408, 1410, 1412 may include one or more of the microorganisms utilized in the system 100. In embodiments, the flow chamber 1402 may include hydrolytic microorganisms, the flow chamber 1406 may include acidogenic microorganisms as described above with respect to the clarifier 300. The flow chamber 1408 may include acetogenic microorganisms as described above with respect the batch reactor 400. The chambers 1410 and 1412 may include methanogenic microorganisms as described above with respect to the digester 500. In further embodiments, the chambers 1402, 1406, 1408 may include acetogenic microorganisms and the chambers 1410 and 1412 may include methanogenic microorganisms. Various microorganisms may be deposited on the digestion substrate 440 as described above with respect to the batch reactor 400 as shown in FIG. 8.

The temperature, pH and ORP within the chambers 1402, 1406, 1408, 1410, 1412 may be substantially the same as within the clarifier 300 (e.g., receptacles 302, 304, 306), the batch reactor 400, and the digester 500 based on the type of microorganisms and/or digestion stage occurring therein. In embodiments, where hydrolytic microorganisms are utilized within any of the chambers 1402, 1406, 1408, 1410, 1412, the temperature may be from about 25° C. to about 50° C., in embodiments from about 30° C. to about 40° C., and in further embodiments from about 35° C. to about 38° C.; the pH may be from about 3 to about 10, in further embodiments from about 5 to about 9, and in yet further embodiments from about 6 to about 8; and the ORP may be from about −50 mV to about +50 mV, in further embodiments from about −400 mV to about 0 mV, and in yet further embodiments from about −200 mV to about −100 mV.

In embodiments, where acidogenic microorganisms are utilized within any of the chambers 1402, 1406, 1408, 1410, 1412, the temperature may be from about 10° C. to about 100° C., in embodiments from about 30° C. to about 80° C., in further embodiments from about 35° C. to about 75° C., in yet further embodiments from about 40° C. to about 60° C.; the pH may be from about 3 to about 10, in embodiments from about 5 to about 9, in further embodiments from about 6 to about 8; and the ORP may be from about −50 mV to about +50 mV, in embodiments about −400 mV to about 0 mV, in further embodiments from about −200 mV to about −100 mV.

In embodiments, where acetogenic microorganisms are utilized within the chambers 1402, 1406, 1408, 1410, 1412 the temperature may be from about 25° C. to about 50° C., in embodiments from about 30° C. to about 40° C., and in further embodiments from about 35° C. to about 38° C. The pH from about 3 to about 10, in embodiments from about 5 to about 9, in further embodiments from about 6 to about 8 and ORP from about −50 mV to about +50 mV, in embodiments about −400 mV to about 0 mV, in further embodiments from about −200 mV to about −100 mV. In embodiments, where methanogenic microorganisms are utilized within the chambers 1402, 1406, 1408, 1410, 1412 the temperature may be from about 25° C. to about 60° C., in embodiments from about 30° C. to about 40° C., in further embodiments from about 35° C. to about 38° C. The pH from about 3 to about 10, in embodiments from about 5 to about 9, in further embodiments from about 6 to about 8 and ORP from about −50 mV to about +50 mV, in embodiments about −400 mV to about 0 mV, and in further embodiments from about −200 mV to about −100 mV.

The flow control assembly 800 of FIGS. 13 and 14 may also be configured to operate with the reactor 1400. As shown in FIG. 16, one or more of the first plurality of gas ports 804-808 and the like may be coupled to the chambers 1402, 1406, 1408, 1410, 1412 to sample gases generated therein. The sampling measurements are transmitted to the logic controller 802, which then outputs the data to a user and/or automatically controls the flow of the digestate and/or gases through the reactor 1400. In embodiments, the controller 802 may be coupled to the flow control mechanisms 1415, 1417, 1416, 1418, 1419, 1420, 1421 to control the flow of the digestate. The controller 802 also periodically samples gases as described with respect to the system 100, and transport the gases between the chambers 1402, 1406, 1408, 1410, 1412, which may be interconnected via various gas piping (not shown).

Transportation of gases between chambers 1402, 1406, 1408, 1410, 1412 allows for removing gases that are generated in one portion of the reactor 1400 to another portion of the reactor 1400 where such gases are used as reactants. In embodiments, the chambers 1402, 1406, 1408 may generate hydrogen gas during hydrolysis, acidogenesis, and acetogenesis reactions that occur therein and the hydrogen gas is used during methanogenesis process within the chambers 1410 and 1412 as described above. Thus, supplying the hydrogen gas to the chambers 1410 and 1412 from the chambers 1402, 1406, 1408 provides for more efficient utilization of the reaction byproducts. The reactor 1400 may also be coupled to the emergency vent 860, the flare burners 850, and the gas take-off 830 for further use at the heat source 600 and other uses as described above with respect to FIGS. 13 and 14.

Figure 17:
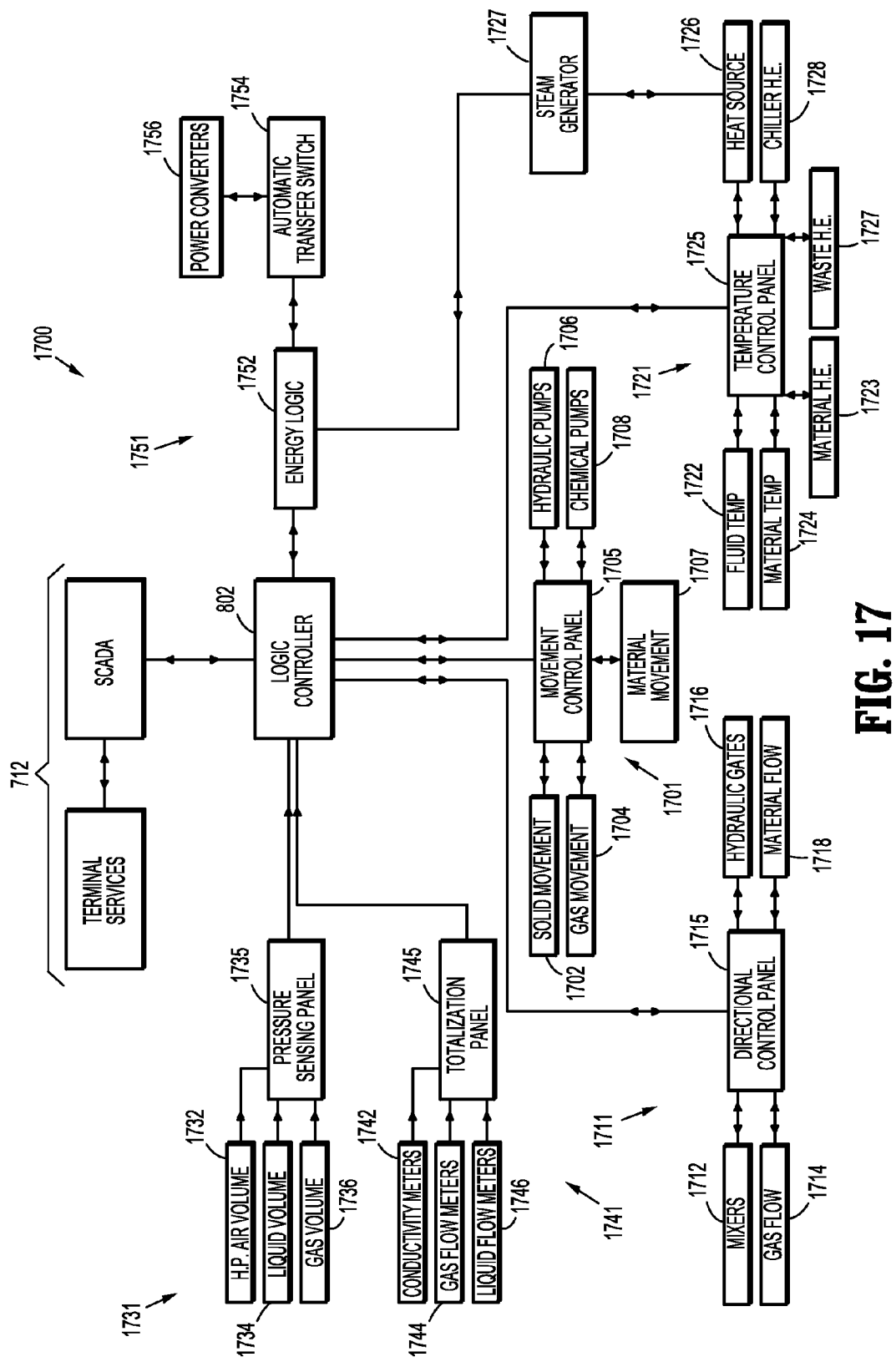
FIG. 17 is a schematic diagram of a anaerobic digestion control system according to the present disclosure.

FIG. 17 illustrates an anaerobic digestion control system 1700 that controls a multi-stage batch or semi-continuous batch process for converting biomaterial into gas. The anaerobic digestion control system 1700 includes the logic controller 802, e.g., a programmable logic controller (PLC), which is electrically coupled to various flow control mechanisms and sensors distributed throughout the digestion system 100.

The digestion control system 1700 also includes the control interface 712 described above, which is in communication with the logic controller 802. The computer system 712 may communicate with the logic controller 802 using any known communications protocol, such as Ethernet TCP/IP, Modbus, or Fieldbus. The control interface 712 may include a server (e.g., the server 1801 of FIG. 18A) and a monitor (e.g., the user interface 1802 of FIG. 18A) connected to the server through which a user can monitor and control the digestion control system 1700. The server may be configured as a terminal services machine that allows for concurrent client sessions and remote access via a wired or wireless connection. In this configuration, an operator may remotely access the server through any device connected to the Internet to view and control the processes described above as well as troubleshoot or make modifications to the digestion control system 1700.

The digestion control system 1700 includes multiple systems that are controlled by the logic controller 802. These systems include a flow control system, which includes a movement control system 1701 and a directional control system 1711, a temperature control system 1721, a pressure sensing system 1731, a totalization system 1741, and an energy control system 1751. In general, the flow control system includes a first flow control mechanism that controls the flow of material through the digestion system 100 and a second flow control mechanism that controls the flow of at least one chemical agent to the material.

As described in more detail below, the pressure sensing system 1731, the totalization system 1741, and the temperature control system 1721 include sensors that sense one or more properties of the material, e.g., biomaterials and gases, flowing through the digestion system 100. The one or more properties of the material may include ORP, pH, temperature, pressure, composition, and combinations thereof. The logic controller 820 may control the flow control system based on the one or more properties of the material. The movement control system 1701 and/or the directional control system 1711 operate to move and direct biomaterials and gases through the digestion system 100 based on feedback from the pressure sensing system 1731 and the totalization system 1741. The temperature control system 1721 ensures that the biomaterials are maintained at optimal temperatures for the production of gases.

The movement control system 1701 and the directional control system 1711 include flow control mechanisms that vary the flow and direction of biomaterials and/or gases through the digestion system 100, which may include the influent collection tank 200, the first and second biomaterial intake receptacles 302, 304, the biological reactors 350, 360, the batch reactor 400, the digester 500, or any combinations thereof.

As shown in FIG. 17, the movement control system 1701 includes a solid movement control subsystem 1702, a gas movement control subsystem 1704, a material movement control subsystem 1707, hydraulic pump control subsystem 1706, and chemical pump control subsystem 1708. The control subsystems 1702, 1704, 1706, 1707, 1708 are controlled by the logic controller 802 via the movement control panel 1705. The movement control panel 1705 may include relays, switches, communication lines, and other interfaces through which the logic controller 802 controls the control subsystems 1702, 1704, 1706, 1707, 1708.

Figure 18A:
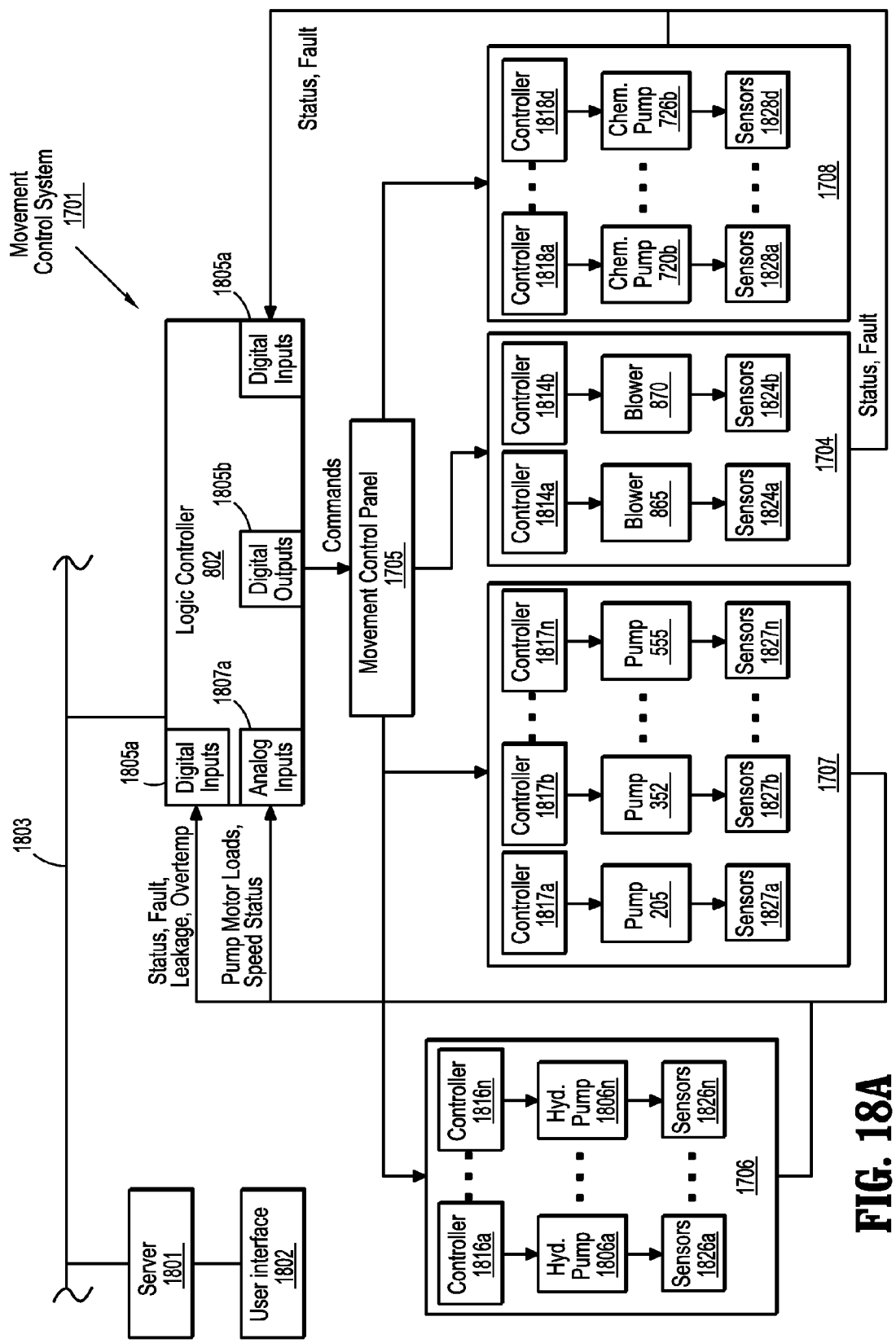
FIG. 18A is a schematic diagram of the movement control system of FIG. 17.

FIG. 18A illustrates an embodiment of the movement control system 1701 of FIG. 17. The logic controller 802 is coupled to a server 1801 via a network connection 1803. A user interface 1802 is coupled to the server to allow an operator to access the server 1801 and the logic controller 802. The movement control panel 1705 is coupled to the digital outputs 1805*b* of the logic controller 802 to receive commands from the logic controller 802. The movement control panel 1705 distributes these commands to the control subsystems 1702, 1704, 1706, 1707, 1708.

The gas movement control subsystem 1704 may include controllers 1814*a-b*, the blowers 865, 870 of FIG. 1, which are controlled by the controllers 1814*a-b*, and sensors 1824*a-b*, which sense operation information about the blowers 865, 870 and transmit the sensed operation information to digital inputs 1805*a* of the logic controller 802. The sensed blower operation information may include status and fault information. The material movement control subsystem 1707 may include controllers 1817*a-n*, the pumps 205, 352, . . . , 555 of FIG. 1, which are controlled by the controllers 1817*a-n*, and sensors 1827*a-n*, which sense operation information about the pumps 205, 352, . . . , 555 and transmit the sensed operation information to the analog inputs 1807*a* of the logic controller 802. The sensed pump operation information may include motor load (e.g., current load), status (e.g., actual speed and over-speed fault), leakage (e.g., when the oil case seal breaks), and temperature (e.g., actual temperature and over-temperature fault).

The hydraulic pump subsystem 1704 may include controllers 1816*a-n*, hydraulic pumps 1806*a-n*, which are controlled by the controllers 1816*a-n*, and sensors 1826*a-n*, which sense operation information about the hydraulic pumps 1806*a-n* and transmit the sensed operation information to digital inputs 1805a of the logic controller 802. The sensed hydraulic pump operation information may include status, fault, leakage, and over-temperature information. The chemical pump subsystem 1704 may include controllers 1818a-d, the chemical pumps 720a-d of FIG. 5, which are controlled by the controllers 1818a-d, and sensors 1828a-n, which sense operation information about the chemical pumps 720a-d and transmit the sensed operation information to digital inputs 1805a of the logic controller 802. The sensed chemical pump operation information may include motor load (e.g., current load), status (e.g., actual speed and over-speed fault), leakage (e.g., of a manifold or a line), and temperature (e.g., actual temperature and over-temperature fault).

Referring again to FIG. 17, the directional control system 1711 includes a mixer control subsystem 1712, a gas flow control system 1714, a hydraulic gate control subsystem 1716, and a material flow control system 1718. The control subsystems 1712, 1714, 1716, 1718 are controlled by the logic controller 802 via the directional control panel 1715. The directional control panel 1705 may include relays, switches, communication lines, and other interfaces through which the logic controller 802 controls the control subsystems 1712, 1714, 1716, 1718.

Figure 18B:
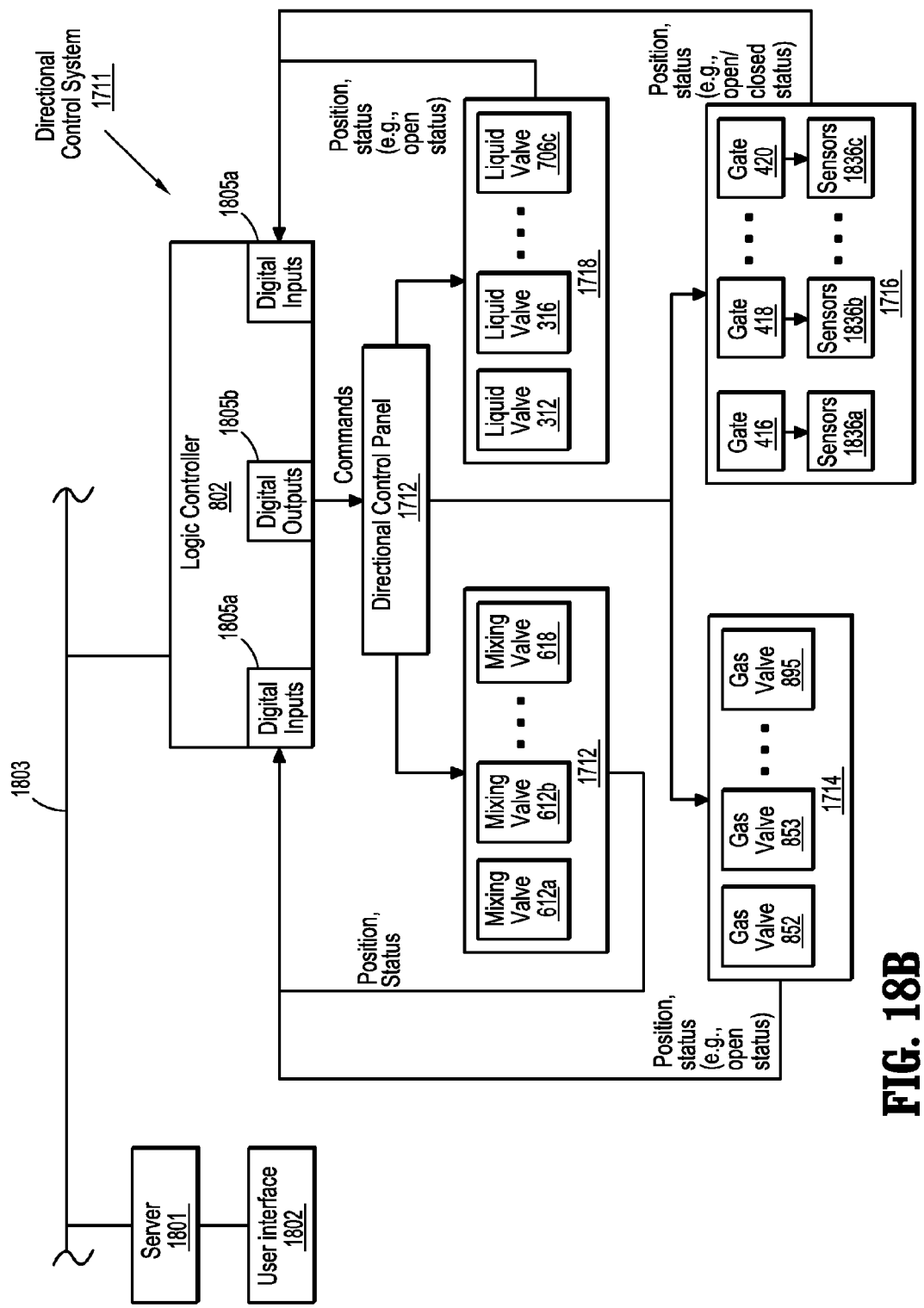
FIG. 18B is a schematic diagram of the directional control system of FIG. 17.

FIG. 18B illustrates an embodiment of the directional control system 1711 of FIG. 17. The logic controller 802 is coupled to a server 1801 via a network connection 1803. A user interface 1802 is coupled to the server to allow an operator to access the server and the logic controller 802. The directional control panel 1715 is coupled to the digital outputs 1805b of the logic controller 802 to receive commands from the logic controller 802. The directional control panel 1715 distributes these commands to the control subsystems 1712, 1714, 1716, 1718.

The mixer control subsystem 1712 may include the mixing valves 612a, 612b, ..., 618 of FIG. 4, which are controlled by the logic controller 802 via the directional control panel 1712. The mixer control subsystem 1712 may provide feedback, such as position and status information, to the digital inputs 1805a of the logic controller 802. The gas flow control system 1714 may include the gas valves 852, 853, ..., 895 of FIGS. 13 and 14, which are also controlled by the logic controller 802 via directional control panel 1712. The gas flow control system 1714 may also provide feedback, such as position and status information, to the digital inputs 1805a of the logic controller 802.

The hydraulic gate control subsystem 1716 may include the hydraulic gates 416, 418, 418 of FIG. 4, which are controlled by the logic controller 802 via the directional control panel 1712, and sensors 1836a-c, which sense operation information about the hydraulic gates 416, 418, 418 and transmit the sensed operation information to digital inputs 1805a of the logic controller 802. The sensed hydraulic gate operation information may include position and status information (e.g., open/closed status). The material flow control system 1718 may include the liquid valves 312, 316, 321a-b, 522, 525-527, 702c, 704c, 706c of FIG. 5, which are also controlled by the logic controller 802 via directional control panel 1712. The material flow control system 1718 may also provide feedback, such as position and status information, to the digital inputs 1805a of the logic controller 802.

In some embodiments, the controllers 1814a-b, 1816a-d, 1817a-n, 1818a-d of the movement control system 1701 include variable frequency drives (VFDs). The controllers 1817a-n control the rate of material flow based on level sensor data (e.g., data from the level sensors 492, 494, 496 of FIG. 4) and/or based on valve and/or gate modulation data (e.g., percent that the liquid valves 312, 316, 321a-b, 522, 525-527, 702c, 704c, 706c of FIG. 5 and/or the hydraulic gates 416, 418, 418 of FIG. 4 are opened or closed). In other embodiments, the controllers 1814a-b, 1816a-d, 1817a-n, 1818a-d include an electromechanical limit switch that limits the speed of the pumps or blowers to a speed that gives the most efficiency.

The controllers 1816a, ..., 1816n control hydraulic pumps 1806a-n, which, in turn, drive gates, such as the hydraulic gates 416, 418, 420, to control the flow of material between reactors or to control the recirculation of material. The controllers 1817a-n may control the rate of material flow based on the pump speed (e.g., measured in RPM) and/or the percent of maximum pump speed over a specified time period.

The gas flow control system 1714 may include controllers (not shown), such as VFDs, which drive the gas valves 852, 853, ..., 895 to modulate or vary the rate of gas flow between reactors. The controllers 1814a-b drive the blowers 865, 870 to vary the rate of gas flow between reactors based on pressure and temperature, which, in turn, are based on the position of the gas valves, e.g., the gas valves 852-859 of FIG. 13.

In general, the hydraulic gate control subsystem 1716 and the material flow control subsystem 1718 include flow control mechanisms that restrict or allow the flow of material to and from reactors, and between reactors. The logic controller 802 controls the modulation, the complete opening, and the complete closing of these flow control mechanisms to control the flow of biomaterial. Biomaterial is retained within a reactor when the flow control mechanism is closed. Depending on the size and shape of the flow control mechanism between reactors and the size and shape of the each reactor, vigorous mixing of biomaterial can be achieved by partially or fully opening flow control mechanisms. In embodiments, the flow control mechanisms include valves and gates.

The orientation of two reactors and the slope and void levels of the reactors may be designed to direct digestate material towards or away from a pump while the opening of the valves or gates achieves homogeneity of digestate material within a reactor or between reactors.

The valves or gates can remain open or closed to achieve a volume setpoint within a reactor that is greater than a volume in another reactor or a differential volume setpoint between reactors so that biomaterial may be exchanged between reactors more vigorously during a period between the opening and closing of the valves or gates without the operation of the material pumps. The material pumps may initiate both before and after the period between the opening and closing of the valves or gates so that the material pumps can contribute to the recirculation of a particular fraction of the digestate.

In general, the directional control system 1711 may control the following processes: opening valves to facilitate the outflow of material from a reactor, opening valves or gates to facilitate inflow of material from another reactor, closing valves to restrict the outflow of material from a reactor, closing valves to restrict the inflow of material from a another reactor, initiating start-stop signals for the material pumps, and modulating speed signals for the material pumps.

Material is retained within a reactor when a valve or gate is closed. The rate of material transfer from one reactor to another, the rate of complete evacuation of material from one reactor to another, or the rate of complete evacuation of material from the digestion system can be modified by changing the size and shape of the valves, gates, and/or piping between two reactors and the size and shape of each reactor.

In embodiments, two reactors that exchange biomaterial may be designed with slopes and may be disposed at different elevations so that specific volumes of digestate within a reactor can be transferred to another reactor without the operation of a pump. The slopes and/or elevation differences between reactors and the orientation of the material pump with respect to the reactor can modify the direction of material flow towards or away from a pump so that the rate of digestate movement (including any fractions of the digestate within a reactor) can be modified.

Specific volumes re-circulated within a receptacle and transferred to or from a receptacle can be achieved through flow meter monitoring. Specific volumes of digestate can be moved over a specific period of time by modulating pump speeds during periods of material movement. The logic controller 802 may control the flow of material and gas between reactors based on retention time and a change in volume, e.g., as determined by a difference in level sensor measurements.

The logic controller 802 and the flow control system, which includes the movement control system 1701 and the directional control system 1711, control the processes described above for preparing biomaterial for the digester 500 and/or the batch reactor 400 (where it is prepared to exit the digestion system 100) and for moving digestate through the digester 500 and/or the batch reactor 400. In embodiments, the logic controller 802 and the flow control system may control processes described above as follows.

With reference to FIG. 1, in a loading mode, biomaterial (e.g., agricultural waste) may be gravity fed into the influent collection tank 200. This may occur each day in the normal course of a farm operation. The loading mode may operate automatically as biomaterial is added to the influent collection tank 200. An operator may also toggle a loading mode button in the control interface 712 to start and stop the loading mode. In embodiments, when the operator turns off the loading mode, the pump 206 may not turn on regardless of the status of the level sensor 465, unless the pump 206 is controlled manually. As used herein, the term "level sensor" refers to any sensor that provides information as to the volume of gas or biomaterial within a receptacle. As described herein, the level sensor may include a pressure sensor or a conductivity sensor positioned within a receptacle to indicate when material or liquid reaches the level of the conductivity sensor.

When the loading mode is enabled and the level sensor 465 senses a high level of biomaterial within the influent collection tank 200, the logic controller 802 starts pump 206 to pump the biomaterial from the influent collection tank 200 into the first biomaterial intake receptacle 302. The logic controller 802 may run the pump 206 until the level sensor 465 senses a low level of biomaterial in the influent collection tank 200. A liquid flow meter 252 may be coupled to the pump 260 to track the total volume of biomaterial introduced into the digestion system 100. The logic controller 802 may be configured to automatically stop the operation of the pump 206 if the second flow control mechanism 316 is open or if the level sensor 465 indicates that the first biomaterial intake receptacle 302 is already at full capacity. The operator may change pump 206 to manual mode at any time and turn off pump 206 during operation of the clarifier 300 when additional influent is not desired. The operator can also turn off the loading mode via the control interface 712.

As described above, before the flow control system transfers the first biomaterial to the digester 500 or the batch reactor 400, the raw biomaterial is processed to achieve a desired consistency in the first and second biomaterial intake receptacles 302, 304. The flow control system pumps the first biomaterial into the first biomaterial intake receptacle 302 and/or deposits the second biomaterial, e.g., silage, in the second biomaterial intake receptacle 304 via a biomaterial processing system 2000, which is illustrated in FIG. 20. The flow control system can achieve the desired consistency by mixing the first biomaterial with previously processed first biomaterial from the digester 500 and/or by processing the first biomaterial with the recirculation chopper pump 314.

In embodiments, the flow control system pumps previously processed first biomaterial from a biological reactor, e.g., biological reactor 360, to the first biomaterial intake receptacle 302. The biomaterial processing system 2000 performs a screening and grinding process on the second biomaterial before it is deposited into the second biomaterial intake receptacle 304. An operator may view the status of and control the biomaterial processing system 2000 via the control interface 712.

The biomaterial processing system 2000 includes a hopper 2001, a mixer 2012, a mixer gate 2014, an auger 2016, and an auger gate 2018. The biomaterial processing system 2000 also includes a hydraulic pump 2024, a variable frequency drive 2032, and a scale 2034 coupled to the logic controller 802. The scale 2034 measures the weight of biomaterial added to the hopper 2001 and provides the weight measurements to the logic controller 802. The hydraulic pump 2024 drives the mixer gate 2014, the auger 2016, and the auger gate 2018 according to commands received from the logic controller 802. The variable frequency drive 2032 controls the motor 2022 based on commands received from the logic controller 802.

The biomaterial processing system 2000 includes multiple rollers 2002*a-g* that are rotatably coupled to two opposing walls of the hopper 2001. The biomaterial processing system 2000 also includes a chain 2005 that is operably coupled to the rollers 2002*a-g* to rotate the rollers 2002*a-g*. Before the biomaterial processing system 2000 starts, an operator provides a weight setpoint to the logic controller 802 to set the amount of second biomaterial to add to the second biomaterial intake receptacle 304. In some embodiments, the operator may enter a stop weight setpoint via the control interface 712 to set the amount of second biomaterial that should remain in the hopper after second biomaterial is added to the second biomaterial intake receptacle 304. For example, if the hopper 2001 contains 1500 lbs. of the second biomaterial and the operator wants to add 1200 lbs. of the second biomaterial to the second biomaterial intake receptacle 304, the operator would need to enter a stop weight setpoint of 300 lbs via the control interface 712.

When the logic controller 802 receives a start command, the logic controller 802 provides a command signal to the VFD 2032, which drives a motor 2022. The motor 2022, in turn, drives a mixer or auger 2012 and the motion of the chain 2005. The mixer 2012 mixes and circulates silage that is input to the hopper 2001 via the input port 2003.

After a predetermined period (e.g., one second) the logic controller 802 issues a command to the hydraulic pump 2024 to open the mixer gate 2014 and to start the auger 2016. After another predetermined period (e.g., one second), the logic controller 802 issues a command to open the auger gate 2018 so that the processed silage can be deposited into the second biomaterial receptacle 304. As the hopper 2001 empties, the weight of the second biomaterial within the hopper 2001 decreases.

When the weight of the second biomaterial measured by the scale 2034 reaches a weight set point (or the operator presses a stop button via the control interface 712), the logic controller 802 initiates the following stop sequence: (1) the logic controller 802 closes the auger gate 2018; (2) when it is confirmed the auger gate 2018 is closed, the logic controller 802 stops the auger 2016; (3) after a predetermined period (e.g., one second), the logic controller 802 issues a command to close the mixer gate 2014; and (4) after another predetermined period, the logic controller 802 issues a command to the controller 2032 to stop the mixer 2012.

Referring again to FIG. 1, when it is necessary to add digestate to the biological reactor 360, the logic controller 802 opens liquid valves 321b, 321c and closes liquid valve 321a so that digestate can flow from the digestate receptacle 306, through the liquid valves 321b, 321c and the liquid flow meter 322, and into the biological reactor 360. In embodiments, the liquid valves 321a, 321b, or any two valves in a "T" configuration, may be replaced with a three-way valve.

If the liquid level within the biological reactor 360 as measured by the level sensor 366 reaches a high-level setpoint, the logic controller 802 closes the liquid valve 321b to prevent overfill of the biological reactor 360. When the logic controller 802 determines that the volume of digestate provided to the biological reactor 360 has reached a predetermined volume setpoint based on liquid flow data from the liquid flow meter 322, the logic controller 802 closes liquid valves 321b, 321c and opens liquid valve 321a.

After digestate has been provided to the biological reactor 360, the logic controller 802 may enable recirculation of the product in the biological reactor 360 either automatically or in response to the operator selecting a button on the control interface 712. When recirculation is enabled, the logic controller 802 issues a command to start the recirculation pump 362, which pumps product out of and back into the biological reactor 360. When a recirculation cycle is complete, the logical controller 802 issues a command to stop the recirculation pump 362.

When recirculation is enabled, the logic controller 802 may continuously cycle between periods of recirculation and non-recirculation. The duration of the recirculation and non-recirculation periods may be set via the control interface 712. In embodiments, the periods may be set to result in eight ten-minute periods of recirculation per day. If the liquid valves 321c-d are open before a recirculation period, the logic controller 802 may pause recirculation. If the liquid valves 321c-d are open during a recirculation period, the logic controller 802 may stop recirculation.

When it is necessary to transfer processed product from the second biological reactor 360 to the first biomaterial receptacle 302, the logic controller 802 opens the liquid valve 321d and starts the pump 362. When the logic controller 802 determines that the level of processed product within the second biological reactor 360 falls below a predetermined low-level setpoint based on data from the level sensor 366, the liquid valve 321d is closed. An operator can initiate transfer from the second biological reactor 360 to the second biomaterial intake receptacle 304 via a button on the control interface 712.

With reference to FIG. 5, when biomaterial is ready to be transferred from the second biomaterial intake receptacle 304 to the first biomaterial intake receptacle 302, the logic controller 802 starts the pump 314 and runs it at a speed determined by a pump speed setpoint. The logic controller 802 also moves liquid valve 522, which is a three-way valve, to a first position. The logic controller 802 runs the pump 314 until a predetermined period set by the operator elapses.

Biomaterial, especially solids, that is deposited into the second biomaterial receptacle 304 can be processed using the chopper pump 314. The operator can manually start processing biomaterial within the second biomaterial intake receptacle 304 by selecting a suitable button via the control interface 712. Alternatively, the logic controller 802 can automatically start processing biomaterial. In either manual mode or automatic mode, the logic controller 802 starts pump 314 and runs it at a speed determined by a pump speed setpoint programmed into the logic controller 802. The logic controller 802 also moves liquid valve 522 to a second position to allow biomaterial within the second biomaterial receptacle to recirculate via fluid line 521. This process runs for a predetermined period set by the operator. When the process is complete, pump 314 shuts down and liquid valve 522 reverts back to the first position, which allows the chopper pump 314 to pump biomaterial into the first biomaterial receptacle 302.

As described above, during normal operation, digestate continuously flows from the digester 500, through the digester pump station 550, through the digestate receptacle 306, and back to the digester 500 in a digester circulation mode. The control interface 712 may include a circulate button that may be toggled to start and stop the digester circulation process.

Referring again to FIG. 1, when the digester circulation process starts, the logic controller 802 opens liquid valve 321a, closes liquid valve 321b, starts and ramps the speed of the digestate receptacle pump 322 to a desired speed setpoint (e.g., 75.5%). The logic controller 802 also starts pump 555 and automatically adjusts its speed based on a PID control algorithm that maintains the digestate level in the digestate receptacle 306 at a predetermined operating level setpoint (e.g., a 20% level) based on feedback from the level sensor 396. When the level of digestate in the digestate receptacle 306 reaches or exceeds a predetermined high level, the logic controller 802 causes the pump 555 to slow down. Conversely, when the level of digestate in the digestate receptacle 306 falls below a predetermined low level, the logic controller 802 causes the digester pump 555 to speed up to maintain the predetermined operating level setpoint.

In some embodiments, if the level of digestate in the digestate receptacle 306 reaches or exceeds a high-level setpoint, the logic controller 802 shuts down the digester pump 555. If the level of digestate falls below a low-level setpoint, the logic controller 802 shut down the digestate receptacle pump 322. When an operator manually deselects the digester circulation mode via the control interface 712, the logic controller 802 closes the liquid valve 321a, opens the liquid valve 321b, and shuts down the digester pump 555 and the digestate receptacle pump 322.

After biomaterials are processed within the first and second biomaterial receptacles 302, 304, e.g., recirculated within the second biomaterial receptacle 304, transferred between the first and second biomaterial receptacles 302, 304, and/or transferred from the second biological reactor 360 to the second biomaterial receptacle 304, the flow control system transfers all of the processed first and second biomaterials, e.g., the processed influent and silage, from the second biomaterial receptacle 304 into the first biomaterial receptacle 302.

Referring again to FIG. 5, in some embodiments, the logic controller 802 closes the gate or valve 312, moves the valve 522 to a first position to allow the processed first and second biomaterials to flow into the first biomaterial receptacle 302, starts the chopper pump 314, and ramps the speed of the chopper pump 314 up to a desired speed setpoint. When the level sensor 394 senses that the biomaterial level within the second biomaterial receptacle 304 has reached a predetermined low level, the logical controller 802 stops the chopper pump 314, maintains the gate 312 in the closed position, and maintains the valve 522 at the first position.

Referring again to FIG. 1, once the second biomaterial receptacle 304 has been emptied, the logic controller 802 initiates the transfer of the biomaterials contained in the first biomaterial receptacle 302 to the digestate receptacle 306 by starting the pump 322 and ramping up its speed to a desired speed setpoint (e.g., 100%). When the level sensor 396 senses that the digestate level within the digestate receptacle 306 has reached a low-level setpoint, the logic controller 802 opens the gate or valve 316 between the first biomaterial receptacle 302 and the digestate receptacle 306, which allows the biomaterial in the first biomaterial receptacle 302 to immediately flow through the gate 316 and into the digestate receptacle 306.

In embodiments, the floor of the digestate receptacle 306 may be disposed below the floor of the first biomaterial receptacle 302 to form a step between the receptacles 302, 306. Thus, when the logic controller 802 opens the gate or valve 316, biomaterial flows from the first biomaterial receptacle 302, down the step, and into digestate receptacle 306 to achieve mixing of the biomaterial without using pumps. When the level sensors 392, 396 both sense a material level that is at a low-level setpoint, the logic controller 802 closes the gate 316 and stops the pump 322.

In some embodiments, the logic controller 802 simultaneously controls the transfer of biomaterial from the first biomaterial receptacle 302 to the digestate receptacle 306 and the circulation of digestate through digester 500. In these embodiments, the logic controller 802 runs the pump 555 at a minimum speed and runs the pump 322 at a greater speed (e.g., 75.5%). As a result, digestate is transferred from the digestate receptacle 306 to the digester 500 at a slow rate, but when the transfer of biomaterial from the first biomaterial receptacle 302 to the digestate receptacle 306 is complete, the normal process of circulating digestate through the digester 500 automatically resumes, allowing the speed of the pump 555 to vary based on the digestate level measured by the level sensor 396 disposed within the digestate receptacle 306.

As described above, the first biological reactor 350 may be a continuous fermentation reactor used to grow and store microbes that are used by the digester 500. At times, a portion of the digestate in the digestate receptacle 306 is transferred to the first biological reactor 350 to sustain the microbes. Also, the first biological reactor 350 provides doses of microbes to the second biomaterial receptacle 304 depending on the demand for microbes.

When it is necessary to add digestate to the first biological reactor 350, the logic controller 802 opens liquid valve 321*f* and closes liquid valve 321*g* during the digester circulation process so that digestate can flow from the digester 500, through the pump station 550, liquid valve 321*f*, and liquid flow meter 326, to the first biological reactor 350. If the liquid level measured by the level sensor 356 within the first biological reactor reaches a high-level setpoint, the logic controller 802 closes the liquid valve 321*f* to prevent overfill of the first biological reactor 350. When the logic controller 802 determines that the volume of digestate provided to the biological reactor 360 has reached a predetermined volume setpoint based, for example, on liquid flow data from the liquid flow meter 326, the logic controller 802 closes liquid valve 321*f* and opens liquid valve 321*g*.

After digestate has been provided to the biological reactor 350, the logic controller 802 may enable recirculation of the product in the biological reactor 350 either automatically or in response to the operator selecting a button on the control interface 712. When recirculation is enabled, the logic controller 802 issues a command to start the recirculation pump 352, which continuously pumps product out of and back into the biological reactor 360. When a recirculation cycle is complete, the logical controller 802 issues a command to stop the recirculation pump 352.

When recirculation is enabled, the logic controller 802 may continuously cycle between periods of recirculation and non-recirculation. The duration of the recirculation and non-recirculation periods may be set via the control interface 712. In embodiments, the periods of recirculation and non-recirculation may be set to result in eight ten-minute periods of recirculation per day. If the liquid valve 321*e* is open before a recirculation period, the logic controller 802 may pause recirculation. If the liquid valve 321*e* is open during a recirculation period, the logic controller 802 may stop recirculation.

When it is necessary to transfer processed product from the first biological reactor 350 to the second biomaterial receptacle 302, the logic controller 802 opens the liquid valve 321*e* and starts the pump 352. When the logic controller 802 determines that the level of processed product within the first biological reactor 350 falls below a predetermined low-level setpoint based on data from the level sensor 356, the liquid valve 321*e* is closed. An operator can initiate transfer from the first biological reactor 350 to the second biomaterial intake receptacle 304 via a button on the control interface 712.

Referring again to FIG. 5, when the logic controller 802 determines that the biomaterial in the digestate receptacle 306 has finished processing, the logic controller opens liquid valves 321*b*, 525 allowing digestate to flow to the batch reactor 400. A volume set point is set in the logic controller 802 for the volume of digestate to be transferred from the digestate receptacle 306 to the batch reactor 400. When the digestate flows from the digestate receptacle 306 to the batch reactor 400, it flows through a liquid flow meter 322.

If the digestate level measured by the level sensors 492, 494, 496 within the batch reactor 400 reaches a high-level set point, the directional control system 1711 issues a high-level alarm and closes the valves 321*b*, 525 to prevent overfill of the batch reactor 400. If the digestate level within the batch reactor 400 reaches the high-level set point, an operator can readjust the volume setpoint to a value below the actual totalized flow as measured by the flow meter 322 or increase the high-level setpoint and reset the high-level alarm to allow digestate flow to proceed to completion.

When the flow meter 322 determines that the volume of digestate has reached a predetermined volume setpoint, the logic controller 802 closes valves 321*b*, 525. The digestate may remain in the batch reactor until the operator provides further input via the control interface 712.

An operator may manually start or stop recirculation of the biomaterial in the batch reactor 400 via a button on the control interface 712. When recirculation starts, the valve 525 is opened and the pump 465 is started. When recirculation is complete, the valve 525 is closed and the speed of the pump 465 returns to the previous setpoint speed.

In some embodiments, the flow control system will continuously cycle between periods of recirculation and non-recirculation. The duration of the recirculation and non-recirculation periods may be programmed via a user interface. The recirculation cycles may be programmed to occur multiple times each day. For example, recirculation may occur in eight ten-minute periods distributed throughout each day. The flow control system may pause recirculation if the valves 321*b*, 525 are opened before recirculation begins. The movement control system 1701 may stop recirculation if the valves 321*b*, 525 are opened during a recirculation period.

In the batch reactor load mode, a predetermined volume of digestate flows into the batch reactor 400. The batch reactor load mode may automatically start after all or a portion of the digestate in the batch reactor 400 is transferred to the digester 500 or elsewhere. Alternatively, the operator can start the batch reactor load mode by selecting an appropriate button via the control interface 712.

In the batch reactor load mode, the two-way valve 521 is opened and the two-way valve 523 is closed to stop the flow of digestate from the digestate receptacle 306 to the digester 500. Then three-way valve 525 is opened, which allows digestate to flow from the digestate receptacle 306 to the batch reactor 400. When the liquid flow meter 325 fluidly coupled between the digestate receptacle 306 and the batch reactor 400 indicates that the predetermined volume of digestate has been reached, the logic controller 802 stops the loading process by closing valve 521, opening valve 523, and closing valve 525.

The flow control system may prevent the batch reactor loading process from starting if a level sensor 492, 494, 496 indicates a high digestate level within the batch reactor 400 or if the control valve 704c is open. Once the batch reactor loading process is started, the control valve 704c is maintained closed until the loading process is complete. The logic controller 802 may pause the batch reactor loading process by closing the valves 521 and 525 and opening the valve 523 if the level sensor indicates a high digestate level. The batch reactor loading process may resume when the digestate level drops below the high digestate level.

In the batch reactor recirculation process, digestate is pumped by pump 524 from the second portion 415 of the batch reactor 400, through valve 525, to the second portion 413 of the batch reactor 400. In some embodiments, the digestate is also pumped through a dry pit pump station. The batch reactor 400 is filled with plastic media described above that could become clogged. The control system may be configured to detect clogged media when there is a large difference between the fluid level within the first portion 413 of the batch reactor 400 and the fluid level within a drainage chamber of the batch reactor 400 (e.g., the drainage chamber 414 of FIG. 6A).

The operator can set a recirculation speed and an allowable difference between the fluid level in the first portion 413 and the fluid level in the drainage chamber 404. The operator can also manually start and stop recirculation by toggling a recirculation button in the graphical user interface. In some embodiments, the recirculation process may include opening valve 525 to allow digestate to flow from the second portion 415 to the first portion 413, starting the pump 514, and ramping up the speed of the pump 524 to a speed setpoint. When recirculation is complete, valve 525 is closed and the pump 524 is shutdown.

When recirculation is enabled, the logic controller 802 controls the flow control system to continuously cycle between periods of recirculation and non-recirculation. The duration of recirculation and non-recirculation periods can be set by the operator. If no duration is set by the user, the control system may use a default setting, such as eight ten-minute periods of recirculation per day.

In some embodiments, the logic controller 802 may control flow control mechanisms, e.g., the liquid valves 321a, 321b and the digestate receptacle pump 322, to simultaneously provide digestate to the batch reactor 400 and the digester 500. The logic controller 802 may vary the position of the liquid valves 321a, 321b to vary the flows of digestate to the batch reactor 400 and the digester 500.

The logic controller 802 may selectively operate the flow control mechanisms (e.g., the blowers 865, 875 or gas valves 852-859) in either a manual mode or an automatic mode. In the manual mode, an operator can selectively issue commands to operate the control devices through a user interface (e.g., a SCADA display). The operator commands may supersede processes that have not yet finished except for those operator commands that would cause irreversible damage to the control devices or other equipment. For example, in manual mode, an operator may turn on a pump to fill a tank that is already full, but cannot turn on the pump if a leak is detected or if a pump is in an over-temperature condition. In automatic mode, the logic controller 802 controls the control subsystems based on feedback from the sensors described herein.

When gas is trapped within a reactor, the pressure and composition of the gases are used by the logic controller 802 to control the transfer of a specified volume of gas to another reactor to modify the rate of reaction in each or both reactors.

With reference to FIG. 13, when the gas in the reactors achieves a specified pressure and composition, the logic controller 802 enables the transfer of specified volumes of that gas to down stream processing and/or to a gas storage unit 880 to prevent unfavorable conditions in the reactors. The logic controller 802 operates appropriate gas flow control mechanisms (e.g., the gas valves 852-859 and blowers 865, 870) to avoid the transfer of gas between two or more reactors that are not complimentary or supplemental to each other.

As described above, the flow control system, which includes the movement control system 1701 and the directional control system 1711, controls the flow of gas by actuating gas valves, blowers, or the combination of the two. In particular, the directional control system 1711 may control the following processes: opening gas valves (e.g., the gas valves 852-859 of FIG. 13) to facilitate the outflow of gas from a reactor, opening the gas valves to facilitate the inflow of gas from another reactor, closing the gas valves to restrict the outflow of gas from a reactor, and closing the gas valves to restrict the inflow of gas from another reactor. The movement control system 1701 may control the following processes: starting and stopping the blowers (e.g., the blowers 865, 870 of FIG. 1) and varying the speed of the blowers.

During operation, gas is exchanged between reactors having different pressures. The directional control panel 1712 actuates gas valves 1714 and the movement control panel 1705 actuates appropriate gas movement subsystems 1704 to transfer gas from a reactor having a first pressure to a reactor having a second pressure lower than the first pressure until the two reactors return to a point within a specified differential pressure range. The control algorithms executed by the logical controller 820 uses pressure data and/or gas composition data from the chromatograph 820 to prevent gases from exchanging between reactors until a setpoint gas composition and/or setpoint pressure are reached.

Referring again to FIG. 13, gas volume data may be calculated based on the gas flow data generated by the gas flow meters 823-829 or the gas pressure data generated by the gas pressure sensors 833-839 and 841. The gas volume data may be monitored during the exchange of gas between reactors to maintain the pressure and/or gas composition within each reactor within a desired setpoint range.

If an event occurs requiring gas evacuation for all low pressure and high pressure reactors and/or requiring a high pressure gas storage unit (e.g., the gas storage unit 880 of FIG. 880) to exchange gas with a low pressure reactor, the logic controller 802 controls the flow control system to cause gas to flow between reactors or among multiple reactors.

The logic controller 802 controls the gas flow control mechanisms based upon upstream and downstream measurement signals within the digestion system including pressure, temperature, and vacuum. The setpoints and setpoint ranges associated with these measurement signals are programmed into the logic controller 802 so that the gas flow control mechanisms (e.g., blowers) are controlled to start and stop at periods prior to or during: pressure swing changes between reactors, evacuation (e.g., reactor or flare), storage gas recirculation, and gas take off for heat and power generation.

Referring again to FIG. 13, when the logic controller 802 determines that (1) gas within a reactor has reached a predetermined gas composition based on information from the gas chromatograph 822, (2) a retention period has elapsed, and (3) the gas pressure as measured by the pressure sensors 843-849 has reached a pressure set point, the logic controller 802 includes PID control loops 803-809 that control the transfer of all or a portion of volatile material by actuating appropriate gas valves 852-859.

Figure 18C:
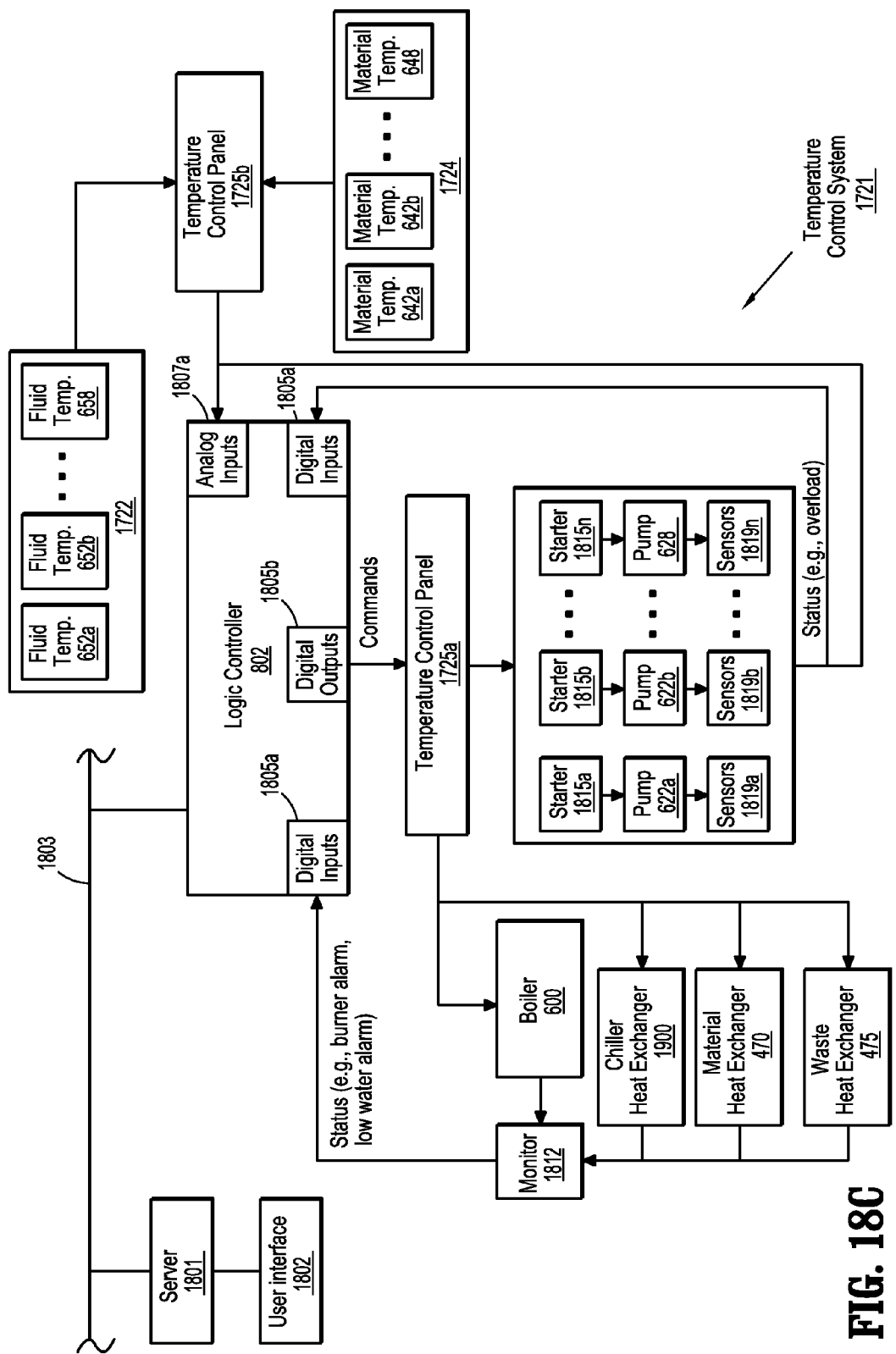
FIG. 18C is a schematic diagram of the temperature control system of FIG. 17.
Figure 18D:
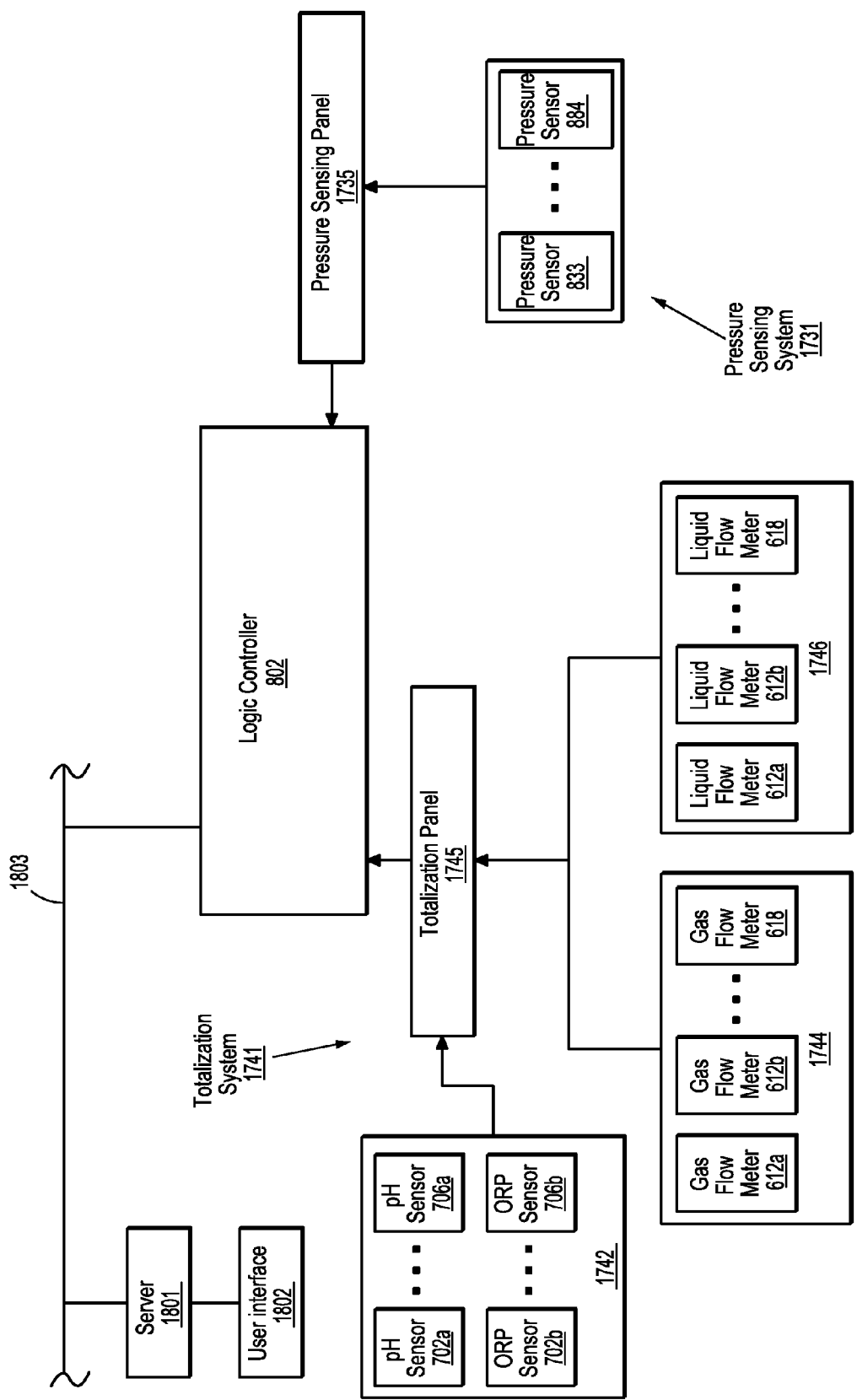
FIG. 18D is a schematic diagram of the totalization and pressure sensing systems of FIG. 17.

As illustrated in FIGS. 17 and 18D, the totalization system 1741 includes conductivity meters 1742, gas flow meters 1744, liquid flow meters 1746, and a totalization control panel 1745, which is coupled to each of the meters 1742, 1744, 1746. The logic controller 802 uses totalization data generated by the totalization system 1741 to determine the total energy potential of material in the digestion system 100. The logic controller 802 may control the flow control system, which includes the movement control system 1701 and the directional control system 1711, based on the determined total energy potential of material in the digestion system 100. The flow control system may control the amount of gas transferred between reactors, the amount of gas re-circulated within a reactor, the amount of gas converted to heat, the amount of gas converted to electricity, the amount of gas flared, or combinations thereof based on the determined total energy potential of material in the digestion system 100.

Figure 20A:
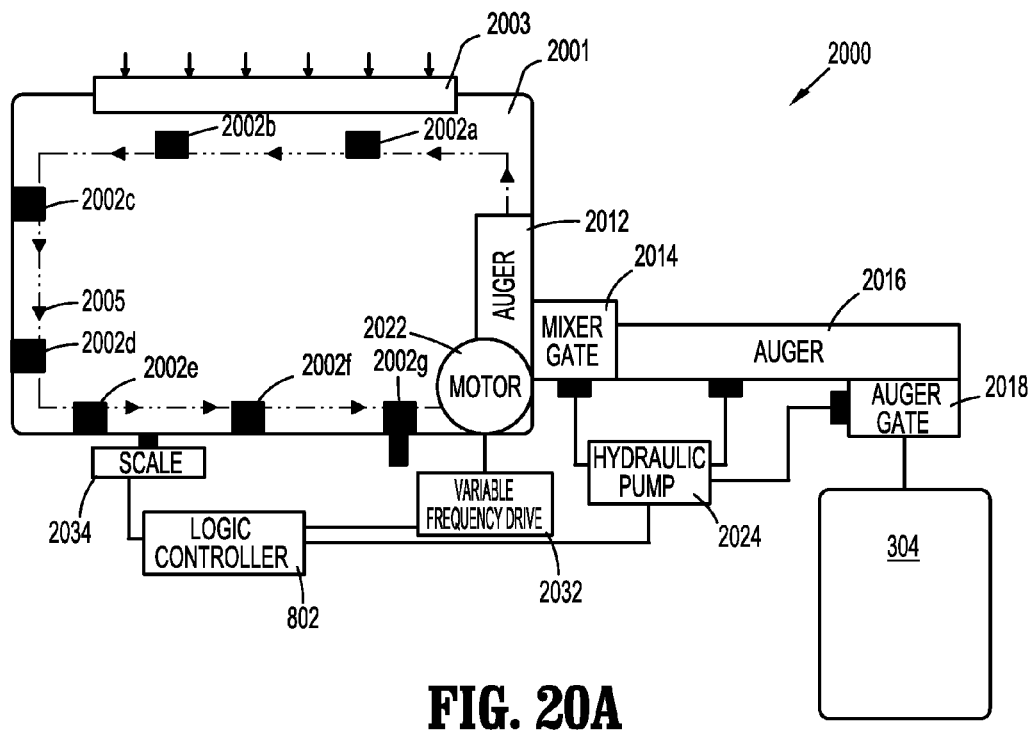
FIG. 20A is a side, cross-sectional view of a biomaterial processing system according to the present disclosure.
Figure 20B:
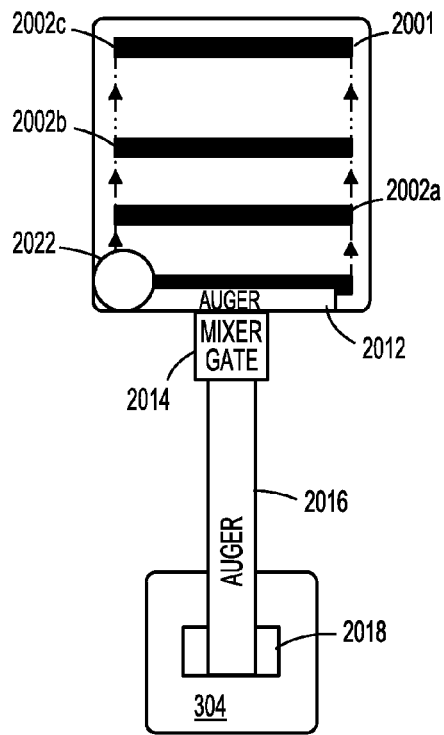
FIG. 20B is a plan, cross-sectional view of a biomaterial processing system according to the present disclosure.

The totalization system 1741 may also include a scale (e.g., the scale 2034 of the biomaterial processing system 2000 of FIGS. 20A and 20B) that provides weight information about the material in the digestion system 100. The logic controller 802 may also use the weight information to determine the total energy potential of the material in the digestion system 100.

As described above, the conductivity meters 1742 may be disposed in each of the reactors, in the fluid lines between reactors, or in the fluid line connected to the chromatograph 820. The conductivity meters 1742 measure how strongly digestate materials oppose the flow of electric current based on ORP described above.

The conductivity measurements are used to control various flow control mechanisms (e.g., valves) that enable the transfer of digestate between reactors, the flow control mechanisms that drive the movement of digestate, the gates that control the retention and movement of digestate material, the valves that select chemicals, and the chemical pumps (e.g., peristaltic pumps) that deliver selected chemicals to the digestate.

In general, during a retention time within a particular reactor, the conductivity meters, which include ORP and pH sensors, take measurements for a predetermined number of periods during: digestate recirculation within a single reactor, material recirculation between reactors, digestate transfer between reactors, and flushing a reactor with other materials to remove residuals.

The logic controller 802 determines whether a previous or current retention time is too short to achieve a desired ORP and/or pH range. If it is determined that the previous or current retention time is too short, the flow control mechanisms (e.g., hydraulic gates 416, 418, 420) are maintained in a closed state to retain biomaterials within a reactor.

As illustrated in FIG. 5, the logic controller 802 also controls the addition of chemicals by simultaneously adjusting the position of the chemical valves 702c, 704c, 706c and actuating one or more chemical pumps (e.g., peristaltic or positive displacement pump) 720b, 722b, 724b, 726b to modify (advance, slow down, or neutralize) a particular reaction to maintain the ORP and/or pH levels of the biomaterial within a desired range. The logic controller 802 controls the amount of chemicals that are added to the reactors by monitoring and controlling the speed of the chemical pumps 720b, 722b, 724b, 726b.

The logic controller 802 also controls material recirculation by operating valves and pumps, e.g., liquid valve 525 and material pump 465 of FIG. 5, based on the ORP and pH measurements. In embodiments, the speed of the material pump 465 and the material rate of turn over is monitored and controlled to achieve homogeneity within each reactor. The logic controller 802 may perform the chemical addition and material recirculation processes simultaneously or sequentially.

The logic controller 802 also controls the transfer of material by opening hydraulic gates 416, 418, 420 to a desired open position to achieve a desired amount of biomaterial transfer. The hydraulic gates 416, 418, 420 may be opened to a partially-open position by controlling the amount of oil that is delivered to the hydraulic gates via the manifold of a hydraulic pump. The logic controller 802 may also command the hydraulic gates 416, 418, 420 to open completely to achieve vigorous mixing via a surge and flush process. The material pumps 416, 418, 420 and chemical addition pumps 720b, 722b, 724b, 726b may be operated simultaneously or sequentially to obtain a desired amount of biomaterial at a desired conductivity level in any reactor.

After all processes governed by ORP and/or pH sensors are completed, subsequent ORP and/or pH measurements are taken to ensure quality. When a specific ORP and/or pH has been achieved, the logic controller 802 concludes that a cycle is complete.

In embodiments, the totalization system 1741 may further include a total organic carbon analyzer, the gas chromatograph 820 of FIG. 13, or both. The total organic carbon analyzer measures volatile organic carbon (POC), total organic carbon (TOC), total nitrogen (TN), or combinations thereof. The total organic carbon analyzer may be coupled in series with the chromatograph 820 of FIG. 13, i.e., in line with the gas flow to the chromatograph 820. The measurement data from the total organic carbon analyzer and/or the gas chromatograph 820 may be used in the same way as the measurement data from the ORP and/or pH sensors to provide feedback to control various processes of the digestion system Referring again to FIG. 17, the totalization system 1741 also includes liquid flow meters that measure the rate of material movement and confirm that specified volumes of material have been transferred to a reactor. Physical characteristics of all material types are determined by K-Factor analysis and are factored into the totalization system 1741 to accurately control the amount of biomaterial transferred between reactors, the amount of material re-circulated, and the amount of residual biomaterial retained within the digestion system.

When raw influent is available, the downstream processing in the clarifier 300 or the batch reactor 400 may require a specified volume of raw influent. For example, when the digestion system 100 is operated as a batch process and the batch reactor 400 has completed a biomaterial processing cycle or is nearing completion of a biomaterial processing cycle, the batch reactor 400 may specify a desired amount of digestate to be provided by the clarifier 300 to keep the batch reactor 400 full. In this case, the liquid flow meter 322 measures the amount of digestate that is transferred from the clarifier 300 to the batch reactor 400 to make sure that the batch reactor 400 is not under- or over-filled.

In a semi-continuous batch process, the liquid flow meter 322 may be used to control the flow of digestate that is provided to the batch reactor 400. In some embodiments, the logic controller 802 may speed up the production of digestate to meet the needs of the batch reactor 400 by heating the biomaterial in the clarifier (e.g., injecting steam into the biomaterial).

The logic controller 302 may factor in the carrying capacity (i.e., total volume versus a specified maximum volume) of a reactor, which is measured by a liquid flow meter 322, and the amount of time required to achieve proper mixing within the reactor to control the transfer of biomaterials.

When solids and liquid biomaterials are required in fractions and/or are completely uncoupled (i.e., the solids and liquid biomaterials are completely separated), the liquid flow meter governs the volume of liquid biomaterials that are transferred to another location. In embodiments, a specified volume of liquid biomaterials may be requested to flush a specified reactor to avoid cross-contamination and/or less-than desirable material accumulation. In this case, a liquid flow meter, e.g., liquid flow meter 322, is used to control the volume of downstream liquid biomaterials (effluent) that is provided to the specified reactor. As another example, when solids and liquid biomaterials are wasted as effluent, the liquid flow meter controls the volume of less-than desirable materials that are transferred from the final stage instead of being recycled back upstream for further processing, including flushing.

The totalization system 1741 also includes gas flow meters (e.g., the gas flow meters 823-829 of FIG. 13) that measure the rate of gas flow and confirm the transfer of specified gas volumes to desired reactors. As described above, the physical specification of all gas types (both volatile and non-volatile) are determined by a primary standard (i.e., calibration gases) using the gas chromatograph 820. The logic controller 802 uses the gas-type information and the gas flow meter data to accurately control the volume of gas transferred between reactors, the volume of gas re-circulated within a reactor, the volume of gas converted to heat (e.g., the volume of gas used as fuel for the boiler), the volume of gas converted to electricity, and the amount of gas flared.

As described above, the digestion control system 1700 may further include a temperature control system 1721 to regulate the temperatures of the materials within the digestion system. With reference to FIGS. 17 and 18C, the temperature control system 1721 includes the logic controller 802, which is connected to a network 1803, and a temperature control panel 1725a-b electrically coupled to the digital outputs 1805b of the logic controller 802. The temperature control system 1721 also includes multiple fluid temperature sensors 652a, 652b, . . . , 658 and multiple material temperature sensors 642a, 642b, . . . , 648, which are electrically coupled to the analog inputs 1807a of the logic controller 802 via the temperature control panel 1725b, which includes communication lines for carrying temperature measurement signals to the analog inputs 1807a of the logic controller 802.

Referring now to FIG. 4, the temperature control system 1721 also include a heat source 600 that supplies heated fluid to the primary or master fluid loop 601 and the plurality of secondary fluid loops 602a, 602b, 602c, 604a, 604b, 606a, 606b, 608. The temperature control system 1721 also includes a plurality of circulation pumps 622a, 622b, 622c, 624a, 624b, 626a, 626b, 628 fluidly coupled to the primary fluid loop 601 and the plurality of secondary fluid loops 602a, 602b, 602c, 604a, 604b, 606a, 606b, 608. The temperature control system 1721 also includes a plurality of starters 1815a-n for starting the circulation pumps 622a, 622b, 622c, 624a, 624b, 626a, 626b, 628 and a plurality of sensors 1819a-n for sensing the speed and status of the plurality of secondary fluid loops 602a, 602b, 602c, 604a, 604b, 606a, 606b, 608. Digital and analog sensor signals from the plurality of sensors 1819a-n are fed back to the digital inputs 1805a and analog inputs 1807a of the logic controller 802 so that the logic controller 802 can control the circulation pumps 622a, 622b, 622c, 624a, 624b, 626a, 626b, 628 via the temperature control panel 1725a based on the digital and analog sensor signals.

The heat source 600, e.g., a boiler, is fluidly coupled to the primary fluid loop 601. The temperature of the primary fluid loop 601 may be measured by the primary fluid loop temperature sensors 641, 651. The first primary fluid loop temperature sensor 641 is disposed at the heat source feed and the second primary fluid loop temperature sensor 651 is disposed at the heat source return. The temperature control system 1721 is coupled to a dedicated controller for the heat source 600 and controls the heat source 600 by sending an enable or disable signal to the heat source controller. An operator may also manually enable or disable the heat source 600 via the control interface 712.

The temperature control system 1721 also includes a chiller heat exchanger 1900, which conditions the gas produced by the digestion system 100 before the gas is supplied to the heat source 600 or the electrical generator 869. The chiller heat exchanger 1900 conditions the gas by, among other things, removing water from the gas. As shown in FIG. 14, the chiller heat exchanger 1900 may be fluidly coupled between the scrubber 832 and the gas blower 870.

Figure 19:
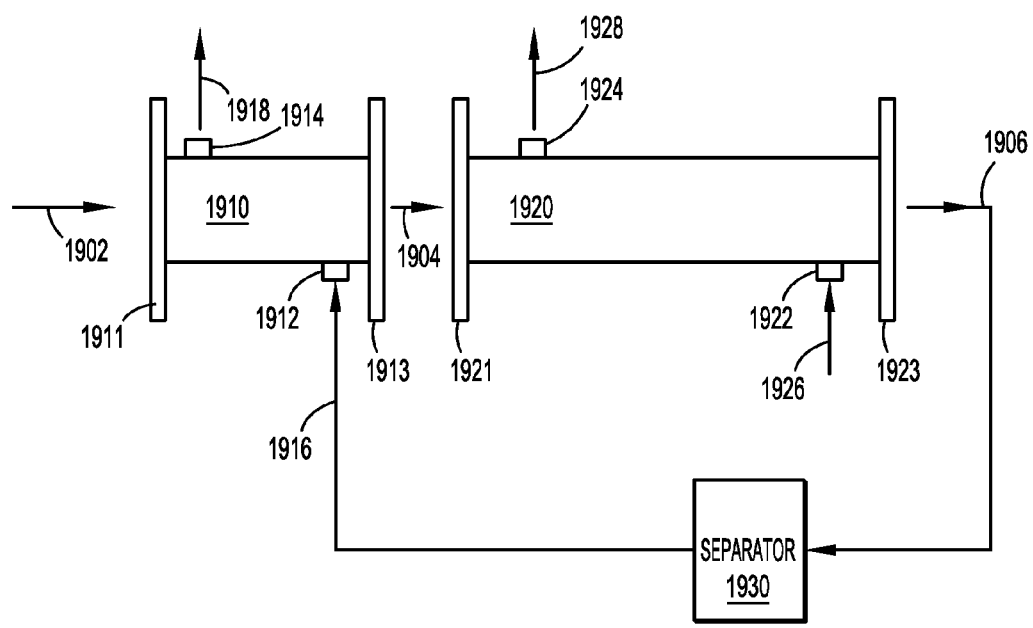
FIG. 19 is a schematic diagram of a chiller heat exchanger according to the present disclosure.

FIG. 19 illustrates a chiller heat exchanger 1900 according to embodiments of the present disclosure. The chiller heat exchanger 1900 includes a first heat exchanger 1910 and a second heat exchanger 1920. The first heat exchanger 1910 may be a gas-to-gas heat exchanger having first and second inlets 1911, 1912, and first and second outlets 1913, 1914. The second heat exchanger 1920 may be a gas-to-liquid heat exchanger having first and second inlets 1921, 1922, and first and second outlets 1923, 1924. The first inlet 1911 of the first heat exchanger 1910 is fluidly coupled to the output of the digestion system 100. The second heat exchanger 1920, in turn, is fluidly coupled in series with the first heat exchanger 1910. Specifically, the first outlet 1913 of the first heat exchanger 1910 is fluidly coupled to the inlet of the 1921 of the second heat exchanger 1920. Also, the second inlet 1912 of the first heat exchanger 1910 is fluidly coupled to the outlet 1923 of the second heat exchanger 1920 via a separator 1930, which is any mechanism that mechanically separates water or other liquid from the gas.

In this configuration, the first heat exchanger 1910 receives, at the first inlet 1911, gas 1902 produced by the digester 500, which may have been processed by the scrubbers 832 (as shown in FIG. 14), and also receives, at the second inlet 1912, gas 1906 that has passed through the second heat exchanger 1920. Then, the first heat exchanger 1920 enables heat transfer from the digester gas 1902 to the gas 1906 output from the second heat exchanger 1920. The second heat exchanger 1920 receives, at the inlet 1921, gas 1904 that has passed through the first heat exchanger 1910 and also receives, at the inlet 1922, cold liquid 1926, such as water from a chiller (not shown) or influent generated by a farm.

In some embodiments, the temperature control system 1721 may include a chiller or fluid cooler (not shown) configured to supply cold fluid to the second heat exchanger 1920 during periods when the outside air temperature yields less than optimal ambient influent temperatures, e.g., during the summer season.

The second chiller heat exchanger 1920 decreases the temperature of the gas from the digester 500 below its dew point temperature to allow entrained water to fall out of the gas and the first chiller heat exchanger 1910 increases the temperature of the gas 1906 output from the second chiller heat exchanger 1920 to a temperature that is within a temperature range that is appropriate for the electrical generator 869 and the heat source 600. In some embodiments, the chiller heat exchanger 1920 is fluidly coupled to other reactors of the digestion system. In some embodiments that include a stand-alone batch reactor 400, the chiller heat exchanger 1920 is fluidly coupled to the stand-alone batch reactor 400. A fluid pump may be coupled to the first inlet 1911 of the first chiller heat exchanger 1910 to push gas through the chiller heat exchanger. Additionally or alternatively, a blower may be coupled to the first outlet 1923 of the second chiller heat exchanger 1920 to pull gas through the chiller heat exchanger 1900.

Referring again to FIG. 1, in some embodiments, a material heat exchanger 470 is fluidly coupled between the batch reactor 400 and the digester 500 for cooling biomaterial that is transferred from the batch reactor 400 to the digester 500. The biomaterial needs to be cooled because of the difference in temperature between the biomaterial in the batch reactor 400 and the biomaterial in the digester 500. The material heat exchanger 470 may receive cold influent from the farm including influent slurry that has not yet flowed into the first receptacle 302 for the pasteurization process. The material heat exchanger 470 enables heat transfer from the biomaterials in the batch reactor 400 to the influent to decrease the temperature of the biomaterial from the batch reactor 400 and to increase the temperature of the influent, bringing the influent closer to mesophilic temperatures. Material pumps and valves are fluidly coupled to the material heat exchanger 470 to control the flow rate and pressure of biomaterial and influent flowing through the material heat exchanger 470 to achieve a desired material-to-material exposure time and to avoid clogging of the material heat exchanger 470. As a result, gas is conserved because less gas is needed by the heat source 600 to heat the influent, pasteurization time is reduced, and flow rates for influent processing are increased.

The temperature control system 1721 may also include a waste heat recovery system. The waste heat recovery system may include a waste heat exchanger 475 and waste heat exchanger temperature sensors (not shown) that sense the temperature of both the gas and liquid circulating through the waste heat exchanger 475. Cooling fluid from the electrical generator 869 is pumped through the waste heat exchanger 475 and the exhaust gas generated by the electrical generator 869 is pulled through the same waste heat exchanger 475. The influent output from the material heat exchanger 470 is also pumped through the waste heat exchanger 475 so that heat is transferred from the cooling fluid and the exhaust gas of the electrical generator 869 to the influent before it is added to the first biomaterial receptacle 302.

In embodiments, return water of the heat source 600 may also be pumped through the waste heat exchanger 475 to facilitate heat transfer from the cooling fluid and exhaust gas of the electrical generator 869 to the return water of the heat source 600 to recover the heat wasted by the electrical generator 869, which is generally inefficient at converting gas to electricity.

In embodiments, the temperature control system 1721 may include a cooling vessel (not shown) that is fluidly coupled between the batch reactor 400 and the digester 500 so that biomaterial can be pumped from the batch reactor 400 into the cooling vessel to be cooled by the ambient environment before being pumped into the digester 500. In embodiments, the temperature control system 1721 may include a liquid-to-liquid heat exchanger incorporated into the batch reactor 400. This liquid-to-liquid heat exchanger may regulate the temperature of digestate within the batch reactor 400 using materials from other reactors or receptacles.

With reference to FIG. 4, the heat source 600 maintains the digestate at an optimal temperature for microbes within all reactors to produce methane gas. The heat source 600 may be fueled by methane or other similar gases produced by the digestion system 100. Alternatively, the heat source 600 may be powered by electricity produced by the electrical generator 869 fueled by the gases produced by the digestion system 100. The heat source 600 may feed a primary fluid loop 601 and multiple secondary fluid loops 602a-c, 604a-b, 606a-b, 608 disposed in the reactors. The temperatures of the plurality of secondary heat loop may be controlled with mixing valves 612a-c, 614a-b, 616a-b, 618, e.g., three-way mixing valves, tied to the primary loop 601.

The temperature of all secondary loop heat exchangers 632a-c, 634a-b, 636a-b, 608a-d in contact with digestate may be limited so that it never exceeds a high temperature that could damage the digestate (e.g., 122° C.). For this reason, the secondary heat loop temperature may be controlled separately from the digestate temperature. Each reactor includes separate temperature sensors 642a-c, 644a-b, 646a-b, 648, 652a-c, 654a-b, 656a-b, 658 to measure the temperature of the digestate and the temperature of the fluid flowing through the secondary fluid loops disposed in each reactor. The temperature of the fluid flowing through the secondary fluid loops 602a-c, 604a-b, 606a-b, 608 are precisely controlled to maintain optimum microbial conditions.

The directional control system 1711 operates together with the temperature control system 1721 to control mixing valves 1712 (e.g., the mixing valves 612a-c, 614a-b, 616a-b, and 618 of FIG. 4) to meter the flow and amount of fluid flowing through the heat exchanger of each reactor (e.g., the heat exchangers 632a-c, 634a-b, and 636a-b of the respective reactors 302, 304, 306, 413, 415, 350, 360, 500 of FIG. 4). In embodiments, the logic controller 802 and the directional control system 1711 control mixing valves 614a-b and circulation pumps 624a-b based on a temperature setpoint for maintaining optimum microbial conditions within the batch reactor 400, the temperature of the biomaterial within the batch reactor 400 as measured by the temperature sensors 644a-b, and the temperature of the heat exchanger fluid as measured by temperature sensors 654a-b.

A high pressure or compressed fluid source (not shown) provides high pressure fluid to diaphragm valves (not shown) at air and fuel inlets to the heat source 600 to control the flow of air and fuel provided to the heat source 600 based on the conditions of the heat exchangers 632a-c, 634a-b, 636a-b, and 638. The modulation of the mixing valves 612a-c, 614a-b, 616a-b, and 618 and the circulation pumps 622a-c, 624a-b, 626a-b, and 628 at each heat exchanger 632a-c, 634a-b, 636a-b, and 638 are also controlled based on heat exchanger conditions.

When any biomaterial enters a reactor of the digestion system 100, the temperature sensors 642a-b, 644a-b, 646a-b, and 648 determine its temperature. Based on temperature setpoints programmed into the logic controller 802, differences in return water temperature and biomaterial temperature control the modulation of the valves 612a-c, 614a-b, 616a-b, and 618. In this case, the circulation pumps 622a-c, 624*a-b*, 626*a-b*, and 628 are initiated to mix the fluid in the primary fluid loop 601, which is taken directly from the heat source heat exchanger 631, with the fluid in the secondary fluid loops 602*a-c*, 604*a-b*, 606*a-b*, and 608, until temperature setpoints are achieved.

The logic controller 802 modulates the mixing valves 612*a-c*, 614*a-b*, 616*a-b*, and 618 and starts and stops the circulation pumps 622*a-c*, 624*a-b*, 626*a-b*, and 628 in series so that biomaterial can be brought to a predetermined temperature during a specified period of time without destroying the surfaces of the lines or pipes of the heat exchangers 632*a-c*, 634*a-b*, 636*a-b*, and 638. When the logic controller 802 determines that the temperature of the biomaterial falls within a predetermined temperature range, it stops the circulation pumps 622*a-c*, 624*a-b*, 626*a-b*, and 628. When the logic controller 802 senses heat losses, it starts another cycle of modulating the mixing valves 612*a-c*, 614*a-b*, 616*a-b*, and 618 and starting and stopping the secondary circulation pumps 622*a-c*, 624*a-b*, 626*a-b*, and 628 to reach and maintain the biomaterial at a predetermined temperature setpoint.

If the temperature control system 1721 detects one or more failure conditions, it may issue an alarm. For example, upon detecting a low water level in the heat source 600, the temperature control system 1721 may issue an alarm that causes the logic controller 802 to shut down all circulation pumps 621, 622*a-c*, 624*a-b*, 626*a-b*, 628. After a low water alarm has issued, the circulation pumps 621, 622*a-c*, 624*a-b*, 626*a-b*, 628 may not restart until the low water alarm has cleared and the operator has manually re-enabled the circulation pumps 621, 622*a-c*, 624*a-b*, 626*a-b*, 628 via the control interface 712. Thus, the primary circulation pump 621 may run constantly in an automatic mode unless the temperature control system 1721 issues a low water alarm. In some embodiments, the temperature control system 1721 may take no action in response to an alarm.

As described above, the logic controller 802 controls the temperature of the biomaterial or digestate by operating the circulator pumps 622*a-c*, 624*a-b*, 626*a-b*, 628. An operating temperature setpoint is associated with each fluid temperature sensor 651, 652*a-c*, 654*a-b*, 656*a-b*, 658. A low temperature setpoint and a high temperature setpoint may be configured as deviations from the operating temperature setpoint. For example, if a deviation of 0.5° C. is set for the low temperature setpoint then the low temperature set point is 36.5° C. If a deviation of 0.5° C. is set for the high temperature setpoint, then the high temperature setpoint is 37.5° C.

When the temperature of the biomaterial or digestate falls below the low temperature setpoint, the temperature control system 1721 starts a corresponding circulator pump 622*a-c*, 624*a-b*, 626*a-b*, 628. The circulator pump 622*a-c*, 624*a-b*, 626*a-b*, 628 runs until the temperature of the material reaches the high temperature setpoint, at which point the temperature control system 1721 shuts off the circulator pump 622*a-c*, 624*a-b*, 626*a-b*, 628. If the temperature of the biomaterial or digestate rises above the high temperature alarm setpoint, which is set higher than the high temperature setpoint (e.g., a deviation of 1 equals 38° C.), or falls below the low temperature alarm setpoint, which is set lower than the low temperature setpoint (e.g., deviation of 1 equals 36° C.), the temperature control system 1721 issues an alarm.

As shown in FIG. 4, the fluid flowing through the secondary fluid loops 602*a-c*, 604*a-b*, 606*a-b*, 608 may be controlled by three-way, motorized mixing valves 612*a-c*, 614*a-b*, 616*a-b*, 618. The mixing valves 612*a-c*, 614*a-b*, 616*a-b*, 618 may be controlled by two electrical signals—a first electrical signal to open the mixing valves 612*a-c*, 614*a-b*, 616*a-b*, 618 and a second electrical signal to close the mixing valves 612*a-c*, 614*a-b*, 616*a-b*, 618. After the circulator pumps 622*a-c*, 624*a-b*, 626*a-b*, 628 start to run, the mixing valves 612*a-c*, 614*a-b*, 616*a-b*, 618 are changed to the open position for a predetermined period. This prevents one or more of the mixing valves 612*a-c*, 614*a-b*, 616*a-b*, 618 from operating when the biomaterial is not heated by a corresponding circulator pump 622*a-c*, 624*a-b*, 626*a-b*, 628.

The temperature control system 1721 may further include gas temperature sensors (not shown). In embodiments, the gas temperature sensors may be disposed near the inlets and outlets of the blowers 865, 870 shown in FIG. 1. Gas temperature data generated by the gas temperature sensors may be fed back to the logic controller 802, which controls the blowers 865, 870 based on the gas temperature data.

The directional control system 1711 controls the extent to which the mixing valves 612*a-c*, 614*a-b*, 616*a-b*, 618 are opened and closed based on the direction and amplitude of the temperature error signal, i.e., the difference between a temperature measured by the temperature sensors 642*a-c*, 644*a-b*, 646*a-b*, 648, 652*a-c*, 654*a-b*, 656*a-b*, 658 and operating temperature setpoints.

For example, if the operating temperature setpoint is set to 42° C. and the temperature is at 42° C., then the logic controller 802 does not issue an open or close command to one or more of the mixing valves 612*a-c*, 614*a-b*, 616*a-b*, 618. If the measured temperature starts to drop slightly, the logic controller 802 may issue a command to open one or more of the mixing valves 612*a-c*, 614*a-b*, 616*a-b*, 618 for a short period. The logic controller 802 may pause for a time delay before sampling the temperature. If the temperature decreases further in the next sample, the logic controller 802 may issue a command to open one or more of the mixing valves 612*a-c*, 614*a-b*, 616*a-b*, 618 for a longer period.

Conversely, when the measured temperature of the material increases above the operating setpoint, the logic controller 802 may issue a command to close one or more of the mixing valves 612*a-c*, 614*a-b*, 616*a-b*, 618. The amount of time that the logic controller 802 opens or closes one or more of the mixing valves 612*a-c*, 614*a-b*, 616*a-b*, 618 depends on the low and high temperature setpoints and the difference between the measured temperature of the material and the operating temperature setpoint.

The control devices of the secondary fluid loops 602*a-c*, 604*a-b*, 606*a-b*, 608 may be manually disabled by the operator via the control interface 712. When the secondary fluid loop 602*a-c*, 604*a-b*, 606*a-b*, 608 is disabled, all circulator pumps 622*a-c*, 624*a-b*, 626*a-b*, 628 turn off and all mixing valves 612*a-c*, 614*a-b*, 616*a-b*, 618 are forced closed. Thus, an operator may disable the secondary heating loops 602*a-c*, 604*a-b*, 606*a-b*, 608, for example, to perform maintenance on the primary and/or secondary fluid loops 601, 602*a-c*, 604*a-b*, 606*a-b*, 608 or to quickly shut down one or more of the secondary fluid loops 602*a-c*, 604*a-b*, 606*a-b*, 608 in an emergency. The operator may also manually control one or more of the circulator pumps 622*a-c*, 624*a-b*, 626*a-b*, 628 via the control interface 712.

Referring again to FIG. 17, the temperature control system 1721 may also include a steam generator 1727. The steam generated by the steam generator 1727 may be injected into the first and/or second biomaterial receptacles 302, 304 to heat the biomaterial contained in the first and/or second biomaterial receptacles 302, 304. The steam generator 1727 is coupled to the heat source heat exchanger 1726, which provides a desired amount of heat to the steam generator 1727. The steam generator 1727 is also coupled to the energy logic 1752, which controls the amount of steam generated by the steam generator 1727 and injected into the first and/or second biomaterial receptacles 302, 304 based on the amount of material provided to the first and second biomaterial receptacles 302, 304.

In some embodiments, the energy logic 1752 may use the weight measurements from the scale 2034 of the second biomaterial processing system 2000 (see FIGS. 20A and 20B) and the material flow measurements from the flow meter 252 (see FIG. 1) to control the amount of steam injected into the first and/or second biomaterial receptacles 302, 304. In other embodiments, the energy logic 1752 may control the weight of low pressure steam that is injected into the first and/or second biomaterial receptacles 302, 304 within a predetermined time period based on the weight of the material added to the first and/or second biomaterial receptacles 302, 304.

With reference to FIGS. 17 and 18D, the digestion control system also includes a pressure sensing system 1731. As shown in FIG. 18D, the pressure sensing system 1731 includes a plurality of pressure sensors 841, 843-849, 881-885 that measure the pressure in each of the reactors and provide pressure sensing data to the logic controller 802 via the pressure sensing panel 1735. The logic controller 802 then translates the measured pressure into liquid volume data 1734 and gas volume data 1736 (e.g., percent volume within a reactor).

The flow control system, which includes the movement control system 1701 and the directional control system 1711, and the temperature control system 1721 use the liquid volume data 1734 and/or the gas volume data 1734 to control liquid and/or gas volumes (e.g., to limit liquid volumes and/or gas volumes), material temperature, material flow rate, material flow direction, retention time, and the number of recirculation cycles within the reactors of the digestion system 100. The pressure sensing system 1731 also includes a pressure sensor (not shown) for sensing the high pressure air volume 1732 of a high pressure fluid source (not shown) that supplies high pressure fluid to drive the valves and gates of the digestion system 100.

As described above, the movement control system 1701 and the directional control system 1711 uses the information generated by the pressure sensing system 1731, e.g., the liquid volume 1734, and the gas volume 1736, to control the flows of biomaterials and gases. The directional control system 1711 also controls the delivery of high pressure or compressed fluid or air for actuating valves and/or gates (e.g., the valves 312, 316, 321a-b, 522, 525-527, 702c, 704c, 706c of FIG. 5 and the gates 416, 418, 418 of FIG. 4) distributed throughout the digestion system 100. The valves may include valves for controlling the direction of biomaterial flows, valves for controlling the direction of gas flows, valves for controlling the direction of chromatograph sampling gas flows, valves for controlling the boiler air-to-fuel ratio, and valves for controlling differential pressure transmitter switches. The digestion system 100 may include an air conditioning unit (not shown) that conditions the air before it is delivered to the valves of the digestion system 100. The air conditioning unit may produce air having desired levels of humidity, pressure, and particulate matter.

The directional control system 1711 uses the pressure information from pressure sensors 843-849 distributed throughout the digestion system 100 to sense leaks. During normal operation, a differential pressure transmitter switch 884 coupled to the digester 500 opens the evacuation valve 894 and starts the flare burners 850 of FIG. 14 when the pressure within the digester 500 exceeds a predetermined differential pressure value. In some embodiments, the evacuation valves, e.g., the primary and secondary evacuation valves 1411, 1412 of FIG. 11, fail open, i.e., return to an open position when they are not otherwise actuated.

When limited power or a complete power failure is detected, the evacuation valve to the flares, e.g., the evacuation valve 894 to the flares 850 of FIG. 14, and the valves that control the flow of biomaterial and gas are opened.

Referring again to FIG. 17, the energy control system 1751 includes energy logic 1752, an automatic transfer switch 1754 coupled to the energy logic 1752, and electrical power converters 1756 (e.g., the electrical generator 869 of FIG. 1) coupled to the automatic transfer switch 1754. The energy logic 1752 calculates and monitors the total energy potential of material within the digestion system 100 and monitors and controls energy use and gas production by the digestion system 100. The energy logic 1752 may calculate total energy potential based on Gibbs free energy calculations.

The energy logic 1752 determines overall system efficiency by comparing the heating and/or electrical loads of the digestion system 100 to the production of gas by the digestion system 100. The energy logic 1752 may also determine the variance of the loads of the digestion system 100 and control gas production based on the variance of the loads of the digestion system 100. For example, the energy logic 1752 may send a command to the logic controller 802 to reduce gas production by the digestion system 100 when the power or heat loads of the digestion system 100 are low and the electrical grid coupled to the electrical generator 869 does not have sufficient capacity to accept any power generated by the electrical generator 869.

If the amount of gas stored within a gas storage unit 880 reaches a predetermined high level, the energy logic 1752 may evacuate gas from the gas storage unit 880 to the environment or to a flare (e.g., the flares 850 of FIG. 14). The energy logic 1752 may use gas flow rate measurements, total gas flow measurements, and gas composition analysis of the evacuated gas to control the production of gas within the digestion system.

If the amount of gas stored within the gas storage unit 880 reaches a predetermined low level, the energy logic 1752 may ignore scheduled flaring protocols and control the run time of the electrical power converters 1754 and the heat source 600 (e.g., boiler) accordingly.

If the evacuation system 890 operates with a gas having a specified composition, e.g., a high-BTU for longer than a specified period, the logic controller 802 may control the flow control system to reduce the amount of biomaterials loaded into the digestion system 100 based on the difference between the gas pressure within a gas storage unit 880 and the atmospheric pressure to avoid high-BTU gas evacuation from the gas storage unit 880, i.e., wasting. The evacuation system 890 may issue an alarm to an operator via the control interface 712 indicating that it is wasting high-BTU gas.

The power converters 1756 may include a primary electrical generator (not shown) and a secondary electrical generator (not shown). If an operational parameter of the primary electrical generator goes out of range, energy logic 1752 operates the automatic transfer switch 1754 to initiate controlled shut down of the primary electrical generator, start up the secondary electrical generator, and trip master circuit breakers to seamlessly switch from the primary electrical generator to secondary electrical generator without failure in the energy control system 1751.

The energy logic 1752 monitors the gas flow, the gas pressure data (which is driven by the blowers), and the gas composition (which is determined by the chromatograph 820 and chromatography software 822) to verify that gas production targets are reached for desired gases, e.g., methane and hydrogen. The energy logic 1752 also uses gas flow rates, gas pressure data, and gas composition data to control the electrical generator 869 to meet the electrical loads of the digestion system 100, and the heat source 600 to meet the heat loads of the digestion system 100.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A control system for a digestion system including a clarifier, a batch reactor, and a digester, the control system comprising:
    a flow control system comprising a first flow control mechanism configured to control the flow of a material through the digestion system and a second flow control mechanism configured to control the flow of at least one chemical agent to the material;
    at least one sensor configured to sense at least one property of the material selected from the group consisting of ORP, pH, temperature, pressure, composition, and combinations thereof; and
    a controller configured to control the flow control system based on the at least one property of the material,
    wherein the flow control system comprises a directional control system configured to simultaneously control the flow of material from the clarifier to the batch reactor and the flow of material from the clarifier to the digester.

2. The control system according to claim 1, wherein the flow control system comprises a movement control system configured to control the flow rate of material in the digestion system and a directional control system configured to control the flow direction of the material in the digestion system.

3. The control system according to claim 1, wherein the flow control system is configured to recirculate material through at least one portion of the digestion system.

4. The control system according to claim 3, wherein the flow control system is further configured to continuously cycle between periods of recirculation and non-recirculation.

5. The control system according to claim 1, further comprising a totalization system configured to sense the volume of a material in at least one portion of the digestion system,
    wherein the controller is further configured to control the flow control system based on the volume of the material in the at least one portion of the digestion system.

6. The control system according to claim 1, wherein the controller is configured to control the amount of gas produced by the digestion system to meet heat loads and electrical loads of the digestion system or external systems by controlling the flow control system.

7. The control system according to claim 1, wherein the flow control system is configured to control at least one of the amount of gas transferred between reactors of the digestion system, the amount of gas re-circulated within a reactor of the digestion system, the amount of gas converted to heat, the amount of gas converted to electricity, or the amount of gas flared.

8. A control system for a digestion system including a clarifier, a batch reactor, and a digester, the control system comprising:
    a flow control system comprising a first flow control mechanism configured to control the flow of a material through the digestion system and a second flow control mechanism configured to control the flow of at least one chemical agent to the material;
    at least one sensor configured to sense at least one property of the material selected from the group consisting of ORP, pH, temperature, pressure, composition, and combinations thereof; and
    a controller configured to control the flow control system based on the at least one property of the material,
    wherein the clarifier and the batch reactor each include a level sensor and the flow control system is configured to transfer material from the clarifier to the batch reactor based on material retention periods for the clarifier and the batch reactor and material levels measured by the level sensors.

9. The control system according to claim 8,
    wherein the digestion system further comprises an influent collection tank having a level sensor, and
    wherein the flow control system is configured to transfer biomaterial from the influent collection tank to the clarifier based on a material retention period for the clarifier and/or the batch reactor and material levels measured by the level sensors.

10. A control system for a digestion system, the control system comprising:
    a flow control system comprising a first flow control mechanism configured to control the flow of a material through the digestion system and a second flow control mechanism configured to control the flow of at least one chemical agent to the material;
    at least one sensor configured to sense at least one property of the material selected from the group consisting of ORP, pH, temperature, pressure, composition, and combinations thereof;
    a totalization system configured to sense the volume of a material in at least one portion of the digestion system; and
    a controller configured to control the flow control system based on the at least one property of the material and the volume of the material in the at least one portion of the digestion system, to determine a total energy potential of the material based on the sensed volume and composition of the material, and to control the flow control system based on the total energy potential of the material.

11. A method of controlling a digestion system, the method comprising:
    sensing at least one property of a material in the digestion system, the at least one property selected from the group consisting of ORP, pH, temperature, pressure, composition, and combinations thereof;
    controlling the flow of at least one chemical agent to the material;
    controlling the flow of the material through the digestion system based on the at least one property of the material,
    determining a total energy potential of the material based on the volume of the material and the composition of the material; and
    controlling the flow of the material through the digestion system based on the total energy potential of the material,
    wherein the digestion system is selected from the group consisting of a clarifier, a batch reactor, a digester, and combinations thereof.

12. The method according to claim 11, wherein controlling the flow of the material comprises controlling the flow rate of the material and the flow direction of the material.

13. The method according to claim 11, further comprising:
determining the volume of the material; and
controlling the flow of the material based on the volume of the material.

14. The method according to claim 11, wherein controlling the flow of the material comprises controlling the flow of gas from the digestion system to a gas storage vessel, a flare, or an evacuation vent based on at least one of the composition of the gas and the pressure of the gas within the digestion system.

15. The method according to claim 11, wherein controlling the flow of the material comprises controlling the amount of gas produced by the digestion system to meet heat loads and electrical loads of the digestion system or external systems.

16. The method according to claim 11, wherein controlling the flow of the at least one chemical agent comprises controlling the flow of the at least one chemical agent based on at least one property of the material selected from the group consisting of ORP, pH, and ORP and pH.

* * * * *